(12) United States Patent
Chao et al.

(10) Patent No.: US 7,314,886 B2
(45) Date of Patent: Jan. 1, 2008

(54) TETRAHYDROPYRANO-INDOLE DERIVATIVES

(75) Inventors: Qi Chao, San Diego, CA (US); Gary T. Elliott, San Diego, CA (US); Lorenzo Leoni, Lodrino (CH); Mimi K. Phillips, San Diego, CA (US)

(73) Assignee: Cephalon, Inc., Frazer, PA (US)

( * ) Notice: Subject to any disclaimer, the term of this patent is extended or adjusted under 35 U.S.C. 154(b) by 238 days.

(21) Appl. No.: 10/957,039

(22) Filed: Oct. 1, 2004

(65) Prior Publication Data

US 2006/0160876 A1 Jul. 20, 2006

Related U.S. Application Data

(60) Provisional application No. 60/556,599, filed on Mar. 26, 2004, provisional application No. 60/508,592, filed on Oct. 2, 2003.

(51) Int. Cl.
*A61K 31/407* (2006.01)
*C07D 491/052* (2006.01)

(52) U.S. Cl. .................. 514/411; 548/432
(58) Field of Classification Search ........... 548/432; 514/411
See application file for complete search history.

(56) References Cited

U.S. PATENT DOCUMENTS

| | | | |
|---|---|---|---|
| 3,590,028 A | 6/1971 | Arcamone et al. |
| 3,843,681 A | 10/1974 | Demerson et al. |
| 3,939,178 A | 2/1976 | Demerson et al. |
| 4,012,448 A | 3/1977 | Smith et al. |
| 4,041,169 A | 8/1977 | Demerson et al. |
| 4,056,537 A | 11/1977 | Demerson et al. |
| 4,070,371 A | 1/1978 | Demerson et al. |
| 4,179,503 A | 12/1979 | Asselin et al. |
| 4,686,213 A | 8/1987 | Ferdinandi et al. |
| 4,748,252 A | 5/1988 | Ferdinandi et al. |
| 5,420,289 A | 5/1995 | Musser et al. |
| 5,561,151 A | 10/1996 | Young et al. |
| 5,776,967 A | 7/1998 | Kreft et al. |
| 5,824,699 A | 10/1998 | Kreft et al. |
| 5,830,911 A | 11/1998 | Failli et al. |
| 5,955,504 A | 9/1999 | Wechter et al. |
| 5,972,986 A | 10/1999 | Seibert et al. |
| 6,025,353 A | 2/2000 | Masferrer et al. |
| 6,255,347 B1 | 7/2001 | Xiaotao et al. |
| 6,545,034 B1 | 4/2003 | Carson et al. |
| 6,552,055 B1 | 4/2003 | Spiegelman et al. |
| 6,573,292 B1 | 6/2003 | Nardella |
| 7,105,560 B1 | 9/2006 | Carson et al. |
| 7,105,561 B2 | 9/2006 | Carson et al. |
| 7,129,262 B2 | 10/2006 | Carson et al. |
| 7,151,100 B1 | 12/2006 | Carson et al. |
| 7,189,752 B2 | 3/2007 | Carson et al. |
| 7,211,599 B2 | 5/2007 | Carson et al. |
| 2002/0015943 A1 | 2/2002 | Bienz |
| 2002/0107280 A1 | 8/2002 | McLaren et al. |
| 2003/0064384 A1 | 4/2003 | Hung et al. |
| 2006/0293253 A1 | 12/2006 | Carson et al. |
| 2007/0111950 A1 | 5/2007 | Carsen et al. |

FOREIGN PATENT DOCUMENTS

| | | |
|---|---|---|
| CA | 1299577 | 4/1992 |
| GB | 1 436 893 | 5/1976 |
| WO | WO 02/12188 A2 | 2/2002 |
| WO | WO 02/088081 | 11/2002 |
| WO | WO 02/092635 | 11/2002 |

OTHER PUBLICATIONS

Kolluri et al. PNAS 2005, 102(7), 2525-2530.*
Brenna et al., "New Enzymatic and Chemical Approaches to Enantiopure Etodolac", *Tetrahedron* (1997), vol. 53, No. 52, pp. 17769-17780.
Demerson et al., "Chemistry and Antiinflammatory Activities of Prodolic-Acid and Related 1,3,4,9-Tetrahydropyrano[3,4-b]indole-1-alkanoic Acids", *Journal of Medicinal Chemistry* (1975), vol. 18, No. 2, pp. 189-191.
Amir et al., 2003, J. Biol. Chem., 278:30828-30834.
Araki et al., "Regulation of Cyclooxygenase-2 Expression by the Wnt and Ras Pathways", Cancer Research (2003), vol. 63, pp. 728-734.
Baek et al., 2001 Mol. Pharmacol. 59:901-908.
Blaker et al., 1999 Genes Chromosomes Cancer 25:399-402.
Briata et al., Mol. Cell., 12:1201-1211.
Carayol et al., 2002, Am. J. Respir Cell Mol Biol., 26:341-347.
Chan et al., 1999, J. Pharmacol Exp. Ther. 290:551-560.
Chung et al., "Regulation of leukemic cell adhesion, proliferation, and survival by 62 -catenin" 2002 Blood 100:982-990.
Dihlmann et al., "Reduction of β-catenin/T-Cell Transcription Factor Signaling by Aspirin and Indomethacin is Caused by an Increased Stabilization of Phosphorylated β-catenin", Molecular Cancer Therapeutics, (2003), vol. 2, pp. 509-516.
Dihlmann et al., Oncogene 20:645-653.
Eriksen et al., "NSAIDs and enantiomers of flurbiprofen target γ-secretase and lower Aβ42 in vivo", 2002 J. Clinical Invest. 112:440-449.
Fukuchi et al., 1998 Cancer Res. 58:3526-3528.
Garcia-Rostan et al., 1999 Cancer Res. 59:1811-1815.
He et al., "PPARδ is an APC-Regulated target of Nonsteriodal Anti-Inflammatory Drugs", 1999 Cell 99:335-345.
Hinz et al., 2002 J. Pharm. Exp. Ther. 300:367-375.
Iwao et al., Jpn. J. cancer Res., 90:205-209.
Korinek et al., "Constitutive Transcriptional Activation by a β-catenin-Tcf Complex in APC$^{-/-}$ Colon Carcinoma" 1997, Science, 275:1784-1787.

(Continued)

*Primary Examiner*—Rebecca Anderson
*Assistant Examiner*—Jason M Nolan

(57) ABSTRACT

Provided herein are indole derivatives, pharmaceutical compositions containing them, methods for their use, and methods for preparing these compounds.

29 Claims, 2 Drawing Sheets

OTHER PUBLICATIONS

Lehmann et al., 1997, J. Biol. Chem., 272:3406-3410.
Li et al., "β-Catenin Signaling", Cancer Biology and therapy (2002), vol. 1, No. 6, 621-625.
Lim et al., "Significance of E-cadherin/β-catenin complex and cyclin D1 in breast cancer", Oncology Reports (2002), vol. 9, 915-928.
Lin et al., 2000 Proc. Natl. Acad. Sci., 97:4262-4266.
Mardini et al., "Selective inhibitors of Cyclooxygenase-2: A growing class of anti-inflammatory drugs", Molecular Inventions (2001), vol. 1, No. 1, 30-38.
McEntee et al., 1999 Carcinogenesis 20:635-640.
Miyoshi et al., "β-catenin: a transforming actor on many stages", Breast Cancer Research (2003) vol. 5, no. 2, 63-68.
Muthukkauppah et al., 1982, J. Natl. Cancer Inst., 69:699-708.
Noda et al., 2002 J. Gastrointerol. 37(11):896-904.
Ohta et al., 2002 Int. J. Oncol. 21:37-42.
Okamura et al., 2003 Cancer Res. 63:728-734.
Park, Ben Ho et al., "Genetic disruption of PPARδ decreases the tumorigencity of human colon cancer cells", Proc. Natl. Acad. Sci., (2001), vol. 98, No. 5., pp. 2598-2603.
Polakis, "Wnt signaling and cancer", 2000 Genes and Development, 14:1837-1851.
Riendeau et al., 1997, Can. J. Physiol. Pharmacol., 75:1088-1095.
Romijn et al., 1988 Prostate 12:99-110.
Rubinfeld et al., 1997 Science 275:1790-1792.
Sakai et al., 2002, Int. J. Oncology 21:547-552.
Sauter et al., "Antisense Cyclin D1 Induces Apoptosis and Tumor Shrinkage in Human Squamous Carcinomas", Cancer Research (1999), vol. 59, 4876-4881.
Shan et al., J.Pharm. Sci., 86 (7), 765-767.
Shiff et al., "The Role of Cyclooxygenase Inhibition in the Antineoplastic Effects of Nonsteroidal Antiinflammatory Drugs (NSAIDs)", J. Exp. Med. (1999), vol. 190, No. 4, 445-450.
Shimada et al., 2002 Gut 50:658-664.
Swinney et al., 1997, J. Biol. Chem. 272:12393-12398.
Takayasu et al., 2001, Clin. Cancer Research, 7:901-908.
Tetsu et al., Nature 398:422-426.
Ueta et al., "β-catenin and cyclin D1 expression in human hepatocellular carcinoma" (2002) Oncology Reports 9:1197-1203.
Wakita et al., 2001, Cancer Res., 61:854-858.
Warner et al., 1999, Proc. Natl. Acad. Sci., 96:7563-7568.
Weggen et al., 2001 Nature 414:212-216.
Winter et al., (1962), Proc. Soc. Exp. Biol. Med. 111-544.
Wong et al., "β-catenin-a linchpin in Colorectal Carcinogensis?", American Journal of Pathology (2002), vol. 160, No. 2, 389-401.
Xu et al., 1994 Int. J. Cancer 59:383-387.
Zhang et al., "Malignant Transformation and Antineoplastic Actions of Nonsteroidal Antiinflammatory Drugs (NSAIDs) on Cyclooxygenase-null Embryo Fibroblasts", Journal of Experimental Medicine (1999), vol. 190, No. 4, 451-459.
Hedvat et al., *Cancer Cell* (2004), vol. 5, pp. 565-574.
Lu et al., *Proc. Natl. Acad. Sci.* (2004), vol. 101, No. 9, pp. 3118-3123.
U.S. Appl. No. 11/615,396, filed Dec. 22, 2006, Carson et al.

\* cited by examiner

SEQUENCE LISTING

```
<160> NUMBER OF SEQ ID NOS: 4

<210> SEQ ID NO 1
<211> LENGTH: 17
<212> TYPE: DNA
<213> ORGANISM: artificial sequence
<220> FEATURE:
<223> OTHER INFORMATION: primers

<400> SEQUENCE: 1
aatgaccccg accgatt                                                 17

<210> SEQ ID NO 2
<211> LENGTH: 19
<212> TYPE: DNA
<213> ORGANISM: artificial sequence
<220> FEATURE:
<223> OTHER INFORMATION: primer

<400> SEQUENCE: 2
gcacaagagg caacgaagg                                               19

<210> SEQ ID NO 3
<211> LENGTH: 20
<212> TYPE: DNA
<213> ORGANISM: artificial sequence
<220> FEATURE:
<223> OTHER INFORMATION: primer

<400> SEQUENCE: 3
```

```
-continued cgccgctaga ggtgaaattc                                              20

<210> SEQ ID NO 4
<211> LENGTH: 19
<212> TYPE: DNA
<213> ORGANISM: artificial sequence
<220> FEATURE:
<223> OTHER INFORMATION: primer

<400> SEQUENCE: 4
ttggcaaatg ctttcgctc                                               19
```

TETRAHYDROPYRANO-INDOLE DERIVATIVES

This application claims priority to U.S. Provisional Application No. 60/508,592, filed Oct. 2, 2003, and U.S. Provisional Application No. 60/556,599, filed Mar. 26, 2004, which are incorporated herein by reference in their entirety.

FIELD OF THE INVENTION

This invention relates to antineoplastic, anti-inflammatory and analgesic indole derivatives, pharmaceutical compositions containing them, methods for their use, and methods for preparing these compounds.

BACKGROUND OF THE INVENTION

Nonsteroidal anti-inflammatory drugs (NSAIDs) are commonly used for the treatment of inflammation, pain, and acute and chronic inflammatory disorders such as osteoarthritis and rheumatoid arthritis. These compounds are thought to work by inhibiting the enzyme cyclooxygenase (COX), which is also known as prostaglandin G/H synthase. COX catalyzes the conversion of arachidonic acid to prostaglandins.

Various forms of COX enzymes have been reported. They include a constitutive form known as COX-1, an inducible form known as COX-2 and the recently discovered COX-3, a variant of COX-1 that is inhibited by acetaminophen. COX-2 is inducible by mitogens, endotoxin, hormones, tumor promoters and growth factors. COX-1 is responsible for endogenous release of prostaglandins important for maintenance of gastrointestinal integrity and renal blood flow. Many of the side effects associated with NSAIDs are believed to be due to the inhibition of COX-1. Because of this, compounds that are selective for COX-2 have been developed and marketed. However, COX-2 inhibitors have been reported to cause dyspepsia, gastropathy and cardiovascular problems.

NSAIDs have also been used for cancer prevention and cancer treatment. The mechanism by which NSAIDs work in cancer treatment and cancer prevention may be related to COX overexpression. For example, some studies appear to indicate a link between COX expression and carcinogenesis. For example, cell lines that overexpress COX-2 are reported to be resistant to apoptosis, have increased invasiveness, and increased angiogenesis potential. Further, studies indicate that increased amounts of prostaglandins and COX-2 are commonly found in premalignant tissues and malignant tumors. Researchers have reported that COX-2 is up-regulated in several types of human cancers, including colon, pancreatic and breast.

Other studies report that the chemoprotective and antineoplastic properties of NSAIDs may occur in a COX-independent mechanism. For example, R-flurbiprofen is chemoprotective in the mouse model of intestinal polyposis and prostate cancer even though it does not have COX inhibitory activity. Similarly, sulindac sulfone, a metabolite of the NSAID sulindac, inhibits azoxy-methane-induced colon tumors in rats even though it does not have COX inhibitory activity. Further, NSAIDs can induce apoptosis in cancer cells that do not express COX-2 (Baek et al. 2001 *Mol. Pharmacol.* 59:901-908). The authors of these studies report that the chemoprotective and antineoplastic effects of NSAIDs occur via COX-dependent and COX-independent mechanisms.

β-catenin (also known as cadherin-associated protein) is a protooncogene in the downstream pathway of the wingless/frizzled (wnt/fzd) signaling pathway. Alterations in the pathways involved in regulating β-catenin are associated in the pathogenesis of many human cancers, including colorectal, desmoid (aggressive fibromatosis), endometrial, hepatocellular, leukemias, kidney, medulloblastoma, melanoma, ovarian, pancreatic, prostate, thyroid and uterine (Polakis, 2000 *Genes Dev.* 14:1837-1851; Chung et al. 2002 *Blood* 100: 982-990).

β-catenin is reported to exist in at least three forms: membrane-bound (adherens complex), cytosolic, and nuclear. The nuclear accumulation of β-catenin, in concert with TCF/LEF proteins, induces downstream genes, including many genes implicated in tumorigenesis, for example, cyclin D1, and c-myc. The literature also reports that β-catenin is involved in the gene regulation of the androgen receptor, providing evidence for a role for the Wnt/β-catenin-TCF pathway for normal and neoplastic prostate growth (Amir et al., 2003, *J. Biol. Chem.* 278:30828-30834). The literature also reports that β-catenin may up-regulate COX-2 (Okamura et al., 2003, *Cancer Res.* 63:728-34).

β-catenin levels are reported to be regulated posttranslationally by the Wnt/fzd signaling pathway. In the absence of a Wnt signal, any β-catenin not bound to adherins is marked for degradation by a complex of proteins bound to β-catenin that includes glycogen synthase kinase-3β (GSK-3β), adenomatous polyposis coli (APC) protein, and axin. This complex facilitates the phosphorylation of β-catenin by GSK-3β and subsequent rapid degradation of β-catenin through proteasome degradation. Binding of Wnts to their receptors results in disruption of the β-catenin complex and inhibition of β-catenin degradation. This results in the accumulation of β-catenin in the cytoplasm and nucleus where it interacts with TCF/LEF proteins to regulate gene expression. Mutations in APC, β-catenin, or axin have been reported to increase the nuclear accumulation of β-catenin in cancers of epithelial origin.

The accumulation of β-catenin in the cytoplasm and nucleus has been reported in tumors with or without β-catenin mutations. In colorectal cancers, APC is mutated in 80% of all cases. In cases without APC mutations, β-catenin mutations are found in 50% of the cases. Accumulation of β-catenin is reported to occur in a very high percentage of cases in hepatoblastomas even though β-catenin is mutated in only 34% of the samples (Blaker et al., 1999 *Genes Chromosomes Cancer* 25:399-402). In hepatocellular carcinomas, β-catenin accumulation results from β-catenin mutations or axin mutation, but rarely APC mutations. Forty-two percent of samples in anaplastic thyroid demonstrate nuclear accumulation of β-catenin. Further, this high accumulation has been reported to correlate with a decrease in survival rate (Garcia-Rostan et al. 1999 *Cancer Res.* 59:1811-5). Rubinfeld et al. reported abnormal β-catenin regulation in 30% of melanoma cell lines (1997 *Science* 275:1790-2). Uterine endometriuim is reported to be associated with β-catenin accumulation in both samples that contain β-catenin mutations and samples without β-catenin mutations (Fukuchi et al. 1998 *Cancer Res.* 58:3526-3528.) Iwao et al. report that 63% of bone and soft-tissue tumors lacking a specific β-catenin mutation still demonstrate β-catenin accumulation (1999 *Jpn. J. Cancer Res.* 90:205-209).

Lin et al. reported that immunohistochemical analysis of cyclin D1 and β-catenin in breast tumors indicated that of 53 samples positive for cyclin D1, 49 of those were also β-catenin positive with β-catenin observed in both the nucleus and cytoplasm (2000 *Proc. Natl. Acad. Sci. USA*

97:4262-4266). A relationship between β-catenin and cyclin D1 has been reported for colon cancer and hepatocellular carcinoma (Tetsue et al. 1999 *Nature* 398:422-426; Ueta et al. 2002 *Oncology Reports* 9:1197-1203). Cyclin D1 is reported to be involved in the pathogenesis of squamous cell carcinoma (Xu et al. 1994 *Int J. Cancer* 59:383-387).

NSAIDs have been reported to affect β-catenin activity. For example, both aspirin and indomethacin have been reported to inhibit transcription of the β-catenin/TCF target cyclin D1 (Dihlmann et al. 2001 *Oncogene* 20:645-53). Sulindac was reported to decrease β-catenin in intestinal tumors from Min/+mice (McEntee et al. 1999 *Carcinogenesis* 20:635-640). Noda et al., report that etodolac increases the expression and cytoplasmic accumulation of cytoplasmic E-cadherin in Caco2 cells, but had no quantitative change in β-catenin expression (2002 *J. Gastorenterol.* 37(11):896-904).

Peroxisome proliferators-activated receptors (PPARs) are nuclear hormone receptors that have been reported to be involved in many cellular processes, including lipid metabolism and disease-related processes. PPARs form dimers with retinoid-X receptor and mediate their effects after ligand binding through gene transcription.

Three isoforms of PPAR are known to date—α, γ, and δ. PPARα is highly expressed in liver and has been reported to stimulate lipid metabolism. PPARγ is highly expressed in adipose tissue and is reported to be involved in activating adipogeneisis. PPARγ is reported to be involved in insulin resistance and a number of neoplastic processes including colorectal cancer. Shimada et al. hypothesize that activation of PPARγ signaling may compensate for deregulated c-myc expression in cells with mutated APC (2002 *Gut* 50:658-664). Ohta et al. report that a PPARγ ligand can cause a shift in β-catenin from the nucleus to the cytoplasm and induction of differentiation in pancreatic cancer cells (2002 *Int J. Oncol.* 21:37-42). PPARδ is expressed in many tissues and organs with the highest expression are brain, colon, and skin. Investigators have implicated PPARδ in cholesterol efflux, colon cancer, embryo implantation, preadipocyte proliferation and epidermal maturation. Investigators report that PPARδ is a downstream target of β-catenin/TCF-4 transcription complex (He et al., 1999 *Cell* 99:335-345). Also, PPARδ mRNA is reported to be overexpressed in many colorectal cancers.

NSAIDs have been reported to activate PPAR receptors (Lehmann et al. 1997 *J Biol. Chem.* 272:3406-3410). Researchers also report that NSAIDs may inhibit PPARδ, which might contribute to the chemoprotective effects of NSAIDs in preventing colorectal cancers (He et al. 1999).

Epidemiological studies indicate that NSAIDs may reduce or prevent the occurrence of Alzheimer's disease. A connection between the COX pathway and Alzheimer's disease has been reported and is mainly based on epidemiological studies. Studies indicate that Cox-2 is up-regulated in areas of the brain related to memory (Hinz et al. 2002 *J. Pharm. Exp. Ther.* 300:367-375). Weggen et al. report that some NSAIDs may reduce the pathogenic amyloid β peptide, Aβ42, by as much as 80% (2001 *Nature* 414:212-216). This reduction has been reported to occur in a COX-independent mechanism (Eriksen et al. 2002 *J. Clinical Invest.* 112:440-449). Eriksen also report that flurbiprofen and its enantiomers lower Aβ42 by targeting the γ-secretase complex that produces Aβ from amyloid β protein precursor. U.S. Pat. No. 6,255,347 discloses the use of R-ibuprofen for the treatment or prevention of Alzheimer's disease.

Analogs of etodolac are known in the art see, for example, U.S. Pat. Nos. 5,830,911; 5,824,699; 5,776,967; 5,420,289; 4,748,252; 4,686,213; 4,070,371; 3,939,178; and 3,843,681.

The use of etodolac and enantiomers of etodolac to treat cancer is described in U.S. Pat. Nos. 6,573,292; 6,545,034; and 5,955,504.

The use of NSAIDs to treat inflammation, cancer, and angiogenesis have been reported in the art see, for example, U.S. Pat. Nos. 5,972,986; 6,025,353; 5,955,504; and 5,561,151.

SUMMARY OF THE INVENTION

Compounds of Formula I, pharmaceutical compositions comprising them, and methods of using them are provided herein:

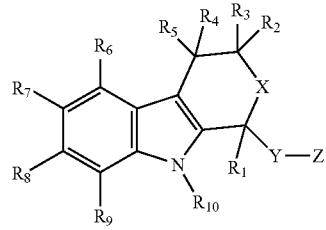

Formula I wherein:
(a) X is C, S or O;
(b) $R_1$ is hydrogen; halogen; —CN; —OH; —SH; —NO$_2$; or an unsubstituted or substituted moiety selected from alkyl, alkenyl, alkynyl, aryl, heteroaryl, heterocycloalkyl, and cycloalkyl, wherein the substituted groups are substituted with one, two or three suitable substituents each independently selected from the group consisting of: halogens, —CN, —NO$_2$, unsubstituted alkyl, unsubstituted alkenyl, unsubstituted heteroalkyl, unsubstituted haloalkyl, unsubstituted alkynyl, unsubstituted aryl, unsubstituted cycloalkyl, unsubstituted heterocycloalkyl, unsubstituted heteroaryl, and —(CH$_2$)$_z$CN where z is an integer from 0 to 6;
(c) $R_2$, $R_3$, $R_4$ and $R_5$ are each independently hydrogen; halogen; —CN; —OH; —SH; —NO$_2$; or an unsubstituted or substituted moiety selected from lower alkyl, lower alkynyl, lower alkenyl, alkoxy, haloalkyl, aryl, and heteroaryl;
(d) $R_6$, $R_7$, $R_8$ and $R_9$ are each independently hydrogen; halogen; —CN; —OH; —SH; —NO$_2$; or an unsubstituted or substituted moiety selected from alkyl, alkenyl, alkynyl, alkoxy, allyloxy, aryl, heteroaryl, cycloalkyl, and heterocycloalkyl, wherein at least one of $R_6$, $R_7$, $R_8$ and $R_9$ is an unsubstituted or substituted moiety selected from aryl, heteroaryl, cycloalkyl, heterocycloalkyl, alkenyl, and alkynyl;
(e) $R_{10}$ is hydrogen; or an unsubstituted or substituted moiety selected from lower alkyl, lower alkenyl, lower alkynyl, aryl; heteroaryl, heterocycloalkyl, and cycloalkyl;
(f) Y is an unsubstituted or substituted moiety selected from alkyl, alkenyl, and alkynyl; and
(g) Z is a moiety selected from —OH, —NH$_2$, —SH, —SO$_2$OH, —S(O)H, —OC(O)NH$_2$, —S(O)$_2$NH$_2$, —NHC(O)H, C(O)NH$_2$, unsubstituted or substituted with one, two or three suitable substituents each independently selected from the group consisting of alkyl, haloalkyl, heteroalkyl, aryl, heteroaryl, cycloalkyl, and heterocycloalkyl;

wherein $R_1$ and Y may cyclize to form an unsubstituted or substituted cycloalkyl group or an unsubstituted or substituted heterocycloalkyl group; or a pharmaceutically acceptable prodrug, pharmaceutically active metabolite, or pharmaceutically acceptable salt thereof.

In some embodiments, the substituted groups in $R_2$, $R_3$, $R_4$, $R_5$, $R_6$, $R_7$, $R_8$, $R_9$ and $R_{10}$ of Formula I are substituted with one, two or three suitable substituents each independently selected from the group consisting of: halogens, =O, =S, —CN, —NO$_2$, alkyl, alkenyl, heteroalkyl, haloalkyl, alkynyl, aryl, cycloalkyl, heterocycloalkyl, heteroaryl, —(CH$_2$)$_z$CN where z is an integer from 0 to 6, =NH, —NHOH, —OH, —C(O)H, —OC(O)H, —C(O)OH, —OC(O)OH, —OC(O)OC(O)H, —OOH, —C(NH)NH$_2$, —NHC(NH)NH$_2$, —C(S)NH$_2$, —NHC(S)NH$_2$, —NHC(O)NH$_2$, —S(O$_2$)H, —S(O)H, —NH$_2$, —C(O)NH$_2$, —OC(O)NH$_2$, —NHC(O)H, —NHC(O)OH, —C(O)NHC(O)H, —OS(O$_2$)H, —OS(O)H, —OSH, —SC(O)H, —S(O)C(O)OH, —SO$_2$C(O)OH, —NHSH, —NHS(O)H, —NHSO$_2$H, —C(O)SH, —C(O)S(O)H, —C(O)S(O$_2$)H, —C(S)H, —C(S)OH, —C(SO)OH, —C(SO$_2$)OH, —NHC(S)H, —OC(S)H, —OC(S)OH, —OC(SO$_2$)H, —S(O$_2$)NH$_2$, —S(O)NH$_2$, —SNH$_2$, —NHCS(O$_2$)H, —NHC(SO)H, —NHC(S)H, and —SH groups unsubstituted or substituted with one, two or three suitable substituents each independently selected from the group consisting of halogens, =O, —NO2, —CN, —OH, —SH, —(CH2)z-CN where z is an integer from 0 to 6, —OR$_c$, —NR$_c$OR$_c$, —NR$_c$R$_c$, —C(O)NR$_c$, —C(O)OR$_c$, —C(O)R$_c$, —NR$_c$C(O)NR$_c$R$_c$, —NR$_c$C(O)R$_c$, —OC(O)OR$_c$, —OC(O)NR$_c$R$_c$, —SRc, unsubstituted alkyls, unsubstituted alkenyls, unsubstituted alkynyls, unsubstituted heteroalkyls, unsubstituted haloalkyls, unsubstituted aryls, unsubstituted cycloalkyls, unsubstituted heterocycloalkyls, and unsubstituted heteroaryls, where $R_c$ is hydrogen, unsubstituted alkyl, unsubstituted alkenyl, unsubstituted alkynyl, unsubstituted aryl, unsubstituted cycloalkyl, unsubstituted heterocycloalkyl, or unsubstituted heteroaryl, or two or more $R_c$ groups together cyclize to form part of a heteroaryl or heterocycloalkyl group unsubstituted or substituted with an unsubstituted alkyl group.

In other embodiments, the substituted groups in $R_2$, $R_3$, $R_4$, $R_5$, $R_6$, $R_7$, $R_8$, $R_9$, and $R_{10}$ of Formula I are substituted with one, two or three suitable substituents each independently selected from the group consisting of: halogens, =O, =S, —CN, —NO$_2$, alkyl, alkenyl, heteroalkyl, haloalkyl, alkynyl, aryl, cycloalkyl, heterocycloalkyl, heteroaryl, —(CH$_2$)$_z$CN where z is an integer from 0 to 6, =NH, —OH, —C(O)H, —OC(O)H, —C(O)OH, —OC(O)OH, —C(NH)NH$_2$, —NHC(O)NH$_2$, —S(O)H, —NH$_2$, —C(O)NH$_2$, —OC(O)NH$_2$, —NHC(O)H, —NHC(O)OH, —C(S)H, and —SH groups unsubstituted or substituted with one, two or three suitable substituents each independently selected from the group consisting of halogens, =O, —NO2, —CN, —OH, —SH, —(CH2)z-CN where z is an integer from 0 to 6, unsubstituted alkyls, unsubstituted alkenyls, unsubstituted alkynyls, unsubstituted heteroalkyls, unsubstituted haloalkyls, unsubstituted aryls, unsubstituted cycloalkyls, unsubstituted heterocycloalkyls, and unsubstituted heteroaryls.

Compounds of Formula I, pharmaceutical compositions comprising them, and methods of using them are provided herein wherein X is S or O; $R_1$ is hydrogen; or an unsubstituted moiety selected from lower alkyl, lower alkenyl, lower alkynyl, aryl, heteroaryl, heterocycloalkyl, and cycloalkyl; $R_2$, $R_3$, $R_4$, and $R_5$ are each independently hydrogen; or an unsubstituted moiety selected from lower alkyl, lower alkynyl, lower alkenyl, alkoxy, haloalkyl, aryl, and heteroaryl; $R_6$, $R_7$, $R_8$, and $R_9$ are each independently hydrogen; or an unsubstituted or substituted moiety selected from alkyl, alkenyl, alkynyl, alkoxy, allyloxy, aryl, heteroaryl, cycloalkyl, and heterocycloalkyl, wherein at least one, but not more than two, of $R_6$, $R_7$, $R_8$, and $R_9$ is an unsubstituted or substituted moiety selected from aryl, heteroaryl, cycloalkyl, heterocycloalkyl, alkenyl, and alkynyl; and $R_{10}$ is hydrogen; or an unsubstituted moiety selected from lower alkyl, lower alkenyl, lower alkynyl, aryl, benzyl, heteroaryl, heterocycloalkyl, and cycloalkyl.

Compounds of Formula I, pharmaceutical compositions comprising them, and methods of using them are provided herein, wherein X is O; $R_1$ is an unsubstituted alkyl group or unsubstituted aryl group; $R_2$, $R_3$, $R_4$, and $R_5$ are each hydrogen; $R_7$ is an unsubstituted or substituted moiety selected from aryl, heteroaryl, cycloalkyl and heterocycloalkyl; and $R_{10}$ is hydrogen. In some embodiments, $R_9$ is an unsubstituted alkyl group. In other embodiments, Y is an unsubstituted alkyl group. In still other embodiments Z is hydroxyl. In still other embodiments, $R_7$ is an aryl or heteroaryl group unsubstituted or substituted with one, two or three suitable substituents each independently selected from the group consisting of: halogens, =O, =S, —CN, —NO$_2$, alkyl, alkenyl, heteroalkyl, haloalkyl, alkynyl, aryl, cycloalkyl, heterocycloalkyl, heteroaryl, —(CH$_2$)$_z$CN where z is an integer from 0 to 6, =NH, —OH, —C(O)H, —OC(O)H, —C(O)OH, —OC(O)OH, —C(NH)NH$_2$, —NHC(O)NH$_2$, —S(O)H, —NH$_2$, —C(O)NH$_2$, —OC(O)NH$_2$, —NHC(O)H, —NHC(O)OH, —C(S)H, and —SH groups unsubstituted or substituted with one, two or three suitable substituents each independently selected from the group consisting of halogens, =O, —NO$_2$, —CN, —OH, —SH, —(CH2)z-CN where z is an integer from 0 to 6, unsubstituted alkyls, unsubstituted alkenyls, unsubstituted alkynyls, unsubstituted heteroalkyls, unsubstituted haloalkyls, unsubstituted aryls, unsubstituted cycloalkyls, unsubstituted heterocycloalkyls, and unsubstituted heteroaryls.

Compounds of Formula I, pharmaceutical compositions comprising them, and methods of using them are provided herein where X is O; $R_1$ is an unsubstituted lower alkyl group or unsubstituted aryl group; $R_2$, $R_3$, $R_4$, and $R_5$ are each hydrogen; $R_9$ is an unsubstituted or substituted moiety selected from alkenyl, alkynyl, aryl, heteroaryl, cycloalkyl, and heterocycloalkyl; and $R_{10}$ is hydrogen. In some embodiments, $R_7$ is an unsubstituted lower alkyl group. In other embodiments, Y is an unsubstituted lower alkyl group. In further embodiments, Z is hydroxyl. In still other embodiments, $R_7$ is an aryl or heteroaryl group unsubstituted or substituted with one, two or three suitable substituents each independently selected from the group consisting of: halogens, =O, =S, —CN, —NO$_2$, alkyl, alkenyl, heteroalkyl, haloalkyl, alkynyl, aryl, cycloalkyl, heterocycloalkyl, heteroaryl, —(CH$_2$)$_z$CN where z is an integer from 0 to 6, =NH, —OH, —C(O)H, —OC(O)H, —C(O)OH, —OC(O)OH, —C(NH)NH$_2$, —NHC(O)NH$_2$, —S(O)H, —NH$_2$, —C(O)NH$_2$, —OC(O)NH$_2$, —NHC(O)H, —NHC(O)OH, —C(S)H, and —SH groups unsubstituted or substituted with one, two or three suitable substituents each independently selected from the group consisting of halogens, =O, —NO2, —CN, —OH, —SH, —(CH2)z-CN where z is an integer from 0 to 6, unsubstituted alkyls, unsubstituted alkenyls, unsubstituted alkynyls, unsubstituted heteroalkyls, unsubstituted haloalkyls, unsubstituted aryls, unsubstituted cycloalkyls, unsubstituted heterocycloalkyls, and unsubstituted heteroaryls.

Compounds of Formula I, pharmaceutical compositions comprising them, and methods of using them are provided herein where X is O; $R_1$ is an unsubstituted moiety selected from aryl, alkyl, and lower-alkoxy; $R_2$, $R_3$, $R_4$, and $R_5$ are each hydrogen; $R_6$ and $R_8$ are each hydrogen or halogen; $R_7$ is an unsubstituted or substituted moiety selected from aryl and heteroaryl; $R_9$ is selected from halogen; unsubstituted alkyl; and an unsubstituted or substituted moiety selected from aryl, heteroaryl, cycloalkyl, alkenyl, and alkynyl; and $R_{10}$ is hydrogen; wherein the substituted groups in $R_7$ and $R_9$ are substituted with one, two or three suitable substituents independently selected from the group consisting of: halogens, =O, =S, —CN, —NO$_2$, alkyl, alkenyl, heteroalkyl, haloalkyl, alkynyl, aryl, cycloalkyl, heterocycloalkyl, heteroaryl, —(CH$_2$)$_z$CN where z is an integer from 0 to 6, =NH, —OH, —C(O)H, —OC(O)H, —C(O)OH, —OC(O)OH, —C(NH)NH$_2$, —NHC(O)NH$_2$, —S(O)H, —NH$_2$, —C(O)NH$_2$, —OC(O)NH$_2$, —NHC(O)H, —NHC(O)OH, —C(S)H, and —SH groups unsubstituted or substituted with one, two or three suitable substituents each independently selected from the group consisting of halogens, =O, —NO2, —CN, —OH, —SH, —(CH2)z-CN where z is an integer from 0 to 6, unsubstituted alkyls, unsubstituted alkenyls, unsubstituted alkynyls, unsubstituted heteroalkyls, unsubstituted haloalkyls, unsubstituted aryls, unsubstituted cycloalkyls, unsubstituted heterocycloalkyls, and unsubstituted heteroaryls. In some embodiments, Y is an unsubstituted lower alkyl group. In other embodiments, Z is hydroxyl.

Also provided herein are compounds of Formula I, pharmaceutical compositions comprising one or more compounds of Formula I, and methods of using them wherein:

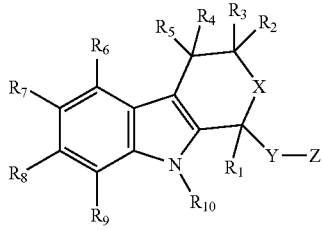

Formula I (a) X is C, S or O;

(b) $R_1$ is hydrogen; halogen; —CN; —OH; —SH; —NO$_2$; or an unsubstituted or substituted moiety selected from alkyl, alkenyl, alkynyl, aryl, heteroaryl, heterocycloalkyl, and cycloalkyl, wherein the substituted groups are substituted with one, two or three suitable substituents each independently selected from the group consisting of: halogens, —CN, —OH, —SH, —NO$_2$, unsubstituted alkyl, unsubstituted alkenyl, unsubstituted heteroalkyl, unsubstituted haloalkyl, unsubstituted alkynyl, unsubstituted aryl, unsubstituted cycloalkyl, unsubstituted heterocycloalkyl, unsubstituted heteroaryl, and —(CH$_2$)$_z$CN where z is an integer from 0 to 6;

(c) $R_2$, $R_3$, $R_4$ and $R_5$ are each independently hydrogen; halogen; —CN; —OH; —SH; —NO$_2$; or an unsubstituted or substituted moiety selected from lower alkyl, lower alkynyl, lower alkenyl, alkoxy, haloalkyl, aryl, and heteroaryl;

(d) $R_6$, $R_8$ and $R_9$ are each independently hydrogen; halogen; —CN; —OH; —SH; —NO$_2$; or an unsubstituted or substituted moiety selected from alkyl, alkenyl, alkynyl, alkoxy, allyloxy, aryl, heteroaryl, cycloalkyl, and heterocycloalkyl;

(e) $R_7$ is hydrogen; halogen; —CN; —OH; —SH; —NO$_2$; or an unsubstituted or substituted moiety selected from alkyl, alkenyl, and alkynyl.

(f) $R_{10}$ is hydrogen; or an unsubstituted or substituted moiety selected from lower alkyl, lower alkenyl, lower alkynyl, aryl; heteroaryl, heterocycloalkyl, and cycloalkyl;

(g) Y is an unsubstituted or substituted moiety selected from alkyl, alkenyl, and alkynyl; wherein the substituted moiety is substituted with one, two or three substitutents each independently selected from halogen; —CN; —OH; —SH; —NO$_2$; unsubstituted alkyls, unsubstituted alkenyls, unsubstituted alkynyls, unsubstituted heteroalkyls, unsubstituted haloalkyls, unsubstituted aryls, unsubstituted cycloalkyls, unsubstituted heterocycloalkyls, and unsubstituted heteroaryls; and (h) Z is a moiety selected from —OH, —NH$_2$, —SH, —OC(O)NH$_2$, —S(O)$_2$NH$_2$, —SO$_2$OH, —S(O)H, —NHC(O)H, C(O)NH$_2$, unsubstituted or substituted with one, two or three suitable substituents each independently selected from the group consisting of alkyl, haloalkyl, heteroalkyl, aryl, heteroaryl, cycloalkyl, and heterocycloalkyl;

wherein $R_1$ and Y may cyclize to form an unsubstituted or substituted cycloalkyl group or an unsubstituted or substituted heterocycloalkyl group; and at least one of $R_6$, $R_7$, $R_8$ and $R_9$ is not hydrogen; or a pharmaceutically acceptable prodrug, pharmaceutically active metabolite, or pharmaceutically acceptable salt thereof.

In some embodiments, the IC50 of the compound is greater than about 50 μM for at least one of COX-1 or COX-2. In other embodiments, the IC50 of the compound is greater than about 100 μM for at least one of COX-1 or COX-2. In yet other embodiments, the IC50 of the compound is greater than about 200 μM for at least one of COX-1 or COX-2.

In other embodiments, the IC50 of the compound is greater than about 50 μM for both COX-1 and COX-2. In other embodiments, the IC50 of the compound is greater than about 100 μM for both COX-1 and COX-2. In yet other embodiments, the IC50 of the compound is greater than about 200 μM for both COX-1 and COX-2.

Compounds of Formula I are described herein wherein: (i) at least one of $R_6$, $R_7$, $R_8$ and $R_9$ is not hydrogen; (ii) when $R_1$ is propyl, Y-Z is ethoxy and $R_9$ is fluorine, $R_6$ is not substituted with a —C(O)-heterocycloalkyl group; (iii) when Y-Z is propoxy and $R_9$ is ethyl, $R_1$ is not CN; (iv) when $R_1$ is ethyl and $R_9$ is ethyl, Y-Z is not unsubstituted or substituted methoxy or unsubstituted or substituted ethoxy; (v) when $R_1$ is methyl and $R_9$ is methyl, Y-Z is not methoxy or ethoxy; (vi) when Y-Z is ethoxy and $R_9$ is ethyl, $R_1$ is not ethoxy; and (vii) when Z is a substituted amide or a substituted amine; $R_6$ is not methyl or chloro; and $R_7$ is not hydroxy, alkoxy-phenyl or methoxy. In some embodiments, Z is unsubstituted hydroxyl.

Compounds of Formula I, pharmaceutical compositions comprising them, and methods of using them are provided herein wherein $R_1$ is hydrogen; or an unsubstituted moiety selected from lower alkyl, lower alkyl-hydroxy, lower alkenyl, lower alkenyl-hydroxy, lower alkynyl, lower alkynyl-hydroxy, aryl, heteroaryl, heterocycloalkyl, and cycloalkyl. In some embodiments, $R_1$ cyclizes with Y to from a substituted or unsubstitued cycloalkyl or heterocycloalkyl group.

Compounds of Formula I, pharmaceutical compositions comprising them, and methods of using them are provided herein wherein $R_2$, $R_3$, $R_4$ and $R_5$ are each independently hydrogen; or an unsubstituted moiety selected from lower alkyl, lower alkynyl, lower alkenyl, alkoxy, haloalkyl, aryl, and heteroaryl. In some embodiments, $R_2$, $R_3$, $R_4$ and $R_5$ are each independently hydrogen.

Compounds of Formula I, pharmaceutical compositions comprising them, and methods of using them are provided herein wherein $R_6$, $R_8$ and $R_9$ are each independently hydrogen; or an unsubstituted or substituted moiety selected from alkyl, alkenyl, alkynyl, alkoxy, allyloxy, aryl, heteroaryl, cycloalkyl, and heterocycloalkyl, wherein at least one of $R_6$, $R_8$ and $R_9$ is not hydrogen. In some embodiments, the substituted moieties are each independently selected from the group consisting of halogen, —CN, alkyl, alkoxy, —NH$_2$, —O-haloalkyl, —CH(O), haloalkyl, aryl, heteroaryl, heterocycloalkyl, alkenyl, alkynyl, —OH, —C(O)$_2$-alkyl, and —C(O)$_2$H.

Compounds of Formula I, pharmaceutical compositions comprising them, and methods of using them are provided herein wherein $R_7$ is hydrogen; halogen; or an unsubstituted or substituted moiety selected from alkyl and alkoxy, wherein the substituted moiety is substituted with one, two or three substituents independently selected from the group consisting of —OH, —SH, —C(O)$_2$-alkyl, —C(O)$_2$H, alkoxy, —O-haloalkyl, halogen, alkyl, haloalkyl, and NH$_2$. In some embodiments, $R_7$ is hydrogen; halogen; —CN; —OH; —SH; —NO$_2$; unsubstituted lower alkyl, unsubstituted lower alkenyl, unsubstituted lower alkynyl, lower alkyl-C(O)$_2$H, lower alkyl-C(O)$_2$-lower alkyl, or alkoxy.

Compounds of Formula I, pharmaceutical compositions comprising them, and methods of using them are provided herein wherein $R_6$ is hydrogen or halogen. Compounds of Formula I and methods of using them are provided herein wherein $R_8$ is hydrogen or halogen.

Compounds of Formula I, pharmaceutical compositions comprising them, and methods of using them are provided herein wherein $R_9$ is hydrogen; halogen; or an unsubstituted or substituted moiety selected from alkyl, aryl, heteroaryl, heterocycloalkyl, haloalkyl, alkynyl, alkenyl, haloalkyl, wherein the substituted moiety is substituted with one, two or three substitutents independently selected from the group consisting of alkyl, —C(O)H, —CN, halogen, alkoxy, aryl, and —C(O)$_2$H.

Compounds of Formula I, pharmaceutical compositions comprising them, and methods of using them are provided herein wherein $R_{10}$ is hydrogen, alkyl, or alkyl-aryl. In some embodiments, X is O. In other embodiments, Y is lower alkyl.

Compounds of Formula I, pharmaceutical compositions comprising them, and methods of using them are provided herein wherein Z is hydroxy. In some embodiments, Z is (C)(O)NH$_2$ unsubstituted or substituted with one or two alkyl groups. In other embodiments, Z is hydroxyl, unsubstituted or substituted lower alkoxy, amino, lower alkylamino, di(lower)alkylamino, arylamino, (aryl)lower alkylamino, di(aryl)lower alkylamino, di(aryl)amino, (heterocycle) amino, (heterocycle)lower alkylamino, di(heterocycle)lower alkylamino, and di(heterocycles)amino.

Compounds of Formula I, pharmaceutical compositions comprising them, and methods of using them are provided herein wherein:

(a) X is S or O;

(b) $R_1$ is hydrogen; or an unsubstituted moiety selected from lower alkyl, lower alkyl-hydroxy, lower alkenyl, lower alkenyl-hydroxy, lower alkynyl, lower alkynyl-hydroxy, aryl, heteroaryl, heterocycloalkyl, and cycloalkyl;

(c) $R_2$, $R_3$, $R_4$ and $R_5$ are each independently hydrogen; or an unsubstituted moiety selected from lower alkyl, lower alkynyl, lower alkenyl, alkoxy, haloalkyl, aryl, and heteroaryl;

(d) $R_6$, $R_8$ and $R_9$ are each independently hydrogen; or an unsubstituted or substituted moiety selected from alkyl, alkenyl, alkynyl, alkoxy, allyloxy, aryl, heteroaryl, cycloalkyl, and heterocycloalkyl, wherein the substituted moieties are each independently selected from the group consisting of halogen, CN, alkyl, alkoxy, NH$_2$, O-haloalkyl, CH(O), haloalkyl, aryl, heteroaryl, heterocycloalkyl, alkenyl, alkynyl, OH, C(O)$_2$-alkyl, and C(O)$_2$H;

(e) $R_7$ is hydrogen; halogen; —CN; —OH; —SH; —NO$_2$; unsubstituted lower alkyl, unsubstituted lower alkenyl, unsubstituted lower alkynyl, lower alkyl-C(O)$_2$H, lower alkyl-C(O)$_2$-lower alkyl, or lower alkoxy; and (f) $R_{10}$ is hydrogen; or an unsubstituted moiety selected from lower alkyl, lower alkenyl, lower alkynyl, aryl, benzyl, heteroaryl, heterocycloalkyl, and cycloalkyl.

Compounds of Formula I, pharmaceutical compositions comprising them, and methods of using them are provided herein wherein:

(a) X is O;

(b) $R_1$ is an unsubstituted alkyl group or unsubstituted aryl group;

(c) $R_2$, $R_3$, $R_4$ and $R_5$ are each hydrogen;

(d) $R_7$ is hydrogen, halogen, unsubstituted lower alkyl, lower alkyl-C(O)$_2$H, lower alkyl-C(O)$_2$-lower alkyl, or alkoxy;

(e) $R_9$ is hydrogen, halogen or an unsubstituted alkyl group;

(f) Y is an unsubstitued alkyl group;

(g) $R_{10}$ is hydrogen; and (h) Z is hydroxyl.

Compounds of Formula I, pharmaceutical compositions comprising them, and methods of using them are provided herein wherein at least one of $R_6$, $R_8$ and $R_9$ is an aryl group unsubstituted or substituted with one, two or three suitable substituents each independently selected from the group consisting of: halogens, =O, =S, —CN, —NO$_2$, alkyl, alkenyl, heteroalkyl, haloalkyl, alkynyl, aryl, cycloalkyl, heterocycloalkyl, heteroaryl, —(CH$_2$)$_z$CN where z is an integer from 0 to 6, =NH, —OH, —C(O)H, —OC(O)H, —C(O)OH, —OC(O)OH, —C(NH)NH$_2$, —NHC(O)NH$_2$, —S(O)H, —NH$_2$, —C(O)NH$_2$, —OC(O)NH$_2$, —NHC(O)H, —NHC(O)OH, —C(S)H, and —SH groups unsubstituted or substituted with one, two or three suitable substituents each independently selected from the group consisting of halogens, =O, —NO$_2$, —CN, —OH, —SH, —(CH2)z-CN where z is an integer from 0 to 6, unsubstituted alkyls, unsubstituted alkenyls, unsubstituted alkynyls, unsubstituted heteroalkyls, unsubstituted haloalkyls, unsubstituted aryls, unsubstituted cycloalkyls, unsubstituted heterocloalkyls, and unsubstituted heteroaryls. In some embodiments, at least one of $R_6$, $R_8$ and $R_9$ is a heteroaryl group unsubstituted or substituted with one, two or three suitable substituents each independently selected from the group consisting of: halogens, =O, =S, —CN, —NO$_2$, alkyl, alkenyl, heteroalkyl, haloalkyl, alkynyl, aryl, cycloalkyl, heterocycloalkyl, heteroaryl, —(CH$_2$)$_z$CN where z is an integer from 0 to 6, =NH, —OH, —C(O)H, —OC(O)H, —C(O)OH, —OC(O)OH, —C(NH)NH$_2$, —NHC(O)NH$_2$, —S(O)H, —NH$_2$, —C(O)NH$_2$, —OC(O)NH$_2$, —NHC(O)H, —NHC(O)OH, —C(S)H, and —SH groups unsubstituted or substituted with one, two or three suitable substituents each independently selected from the group consisting of halogens, =O, —NO$_2$, —CN, —OH, —SH, —(CH$_2$)z-CN where z is an integer from 0 to 6, unsubstituted alkyls, unsubstituted alkenyls, unsubstituted alkynyls, unsubstituted heteroalkyls, unsubstituted haloalkyls, unsubstituted aryls, unsubstituted cycloalkyls, unsubstituted heterocycloalkyls, and unsubstituted heteroaryls. In other embodiments, at least one of R$_6$, R and R$_9$ is a heterocycloalkyl group unsubstituted or substituted with one, two or three suitable substituents each independently selected from the group consisting of: halogens, =O, =S, —CN, —NO$_2$, alkyl, alkenyl, heteroalkyl, haloalkyl, alkynyl, aryl, cycloalkyl, heterocycloalkyl, heteroaryl, —(CH$_2$)$_z$CN where z is an integer from 0 to 6, =NH, —OH, —C(O)H, —OC(O)H, —C(O)OH, —OC(O)OH, —C(NH)NH$_2$, —NHC(O)NH$_2$, —S(O)H, —NH$_2$, —C(O)NH$_2$, —OC(O)NH$_2$, —NHC(O)H, —NHC(O)OH, —C(S)H, and —SH groups unsubstituted or substituted with one, two or three suitable substituents each independently selected from the group consisting of halogens, =O, —NO$_2$, —CN, —OH, —SH, —(CH$_2$)z-CN where z is an integer from 0 to 6, unsubstituted alkyls, unsubstituted alkenyls, unsubstituted alkynyls, unsubstituted heteroalkyls, unsubstituted haloalkyls, unsubstituted aryls, unsubstituted cycloalkyls, unsubstituted heterocycloalkyls, and unsubstituted heteroaryls.

Compounds of Formula I, pharmaceutical compositions comprising them, and methods of using them are provided herein wherein:

(a) X is O or S;

(b) R$_1$ is an unsubstituted lower alkyl group or unsubstituted aryl group;

(c) R$_2$, R$_3$, R$_4$ and R$_5$ are each hydrogen;

(d) R$_6$ is hydrogen or halogen;

(e) R$_7$ is hydrogen, halogen, unsubstituted lower alkyl, lower alkyl-C(O)$_2$H, lower alkyl-C(O)$_2$-lower alkyl, or alkoxy;

(f) R$_8$ is hydrogen or halogen;

(g) R$_9$ is hydrogen; or an unsubstituted or substituted moiety selected from alkenyl, alkynyl, aryl, heteroaryl, cycloalkyl, and heterocycloalkyl; and (h) R$_{10}$ is hydrogen. In some embodiments, Y is an unsubstituted lower alkyl group and Z is hydroxyl.

In some embodiments, R$_9$ is a branched alkyl group. In other embodiments, R$_7$ is not hydrogen. In still other embodiments, R$_7$ is a small chemical group, wherein small is defined as taking up less space than a phenyl group. In still other embodiments, Y-Z is an unsubstituted ethoxy group. In yet other embodiments, R$_1$ is an unsubstituted ethyl group. In yet other embodiments, Z is a moiety selected from —OH, —SH and —OC(O)NH$_2$.

Pharmaceutical compositions comprising a therapeutically effective amount of a compound of Formula I and a pharmaceutically acceptable carrier are provided herein.

Exemplary compounds within Formulas I are shown below:

| NO. | STRUCTURE |
|---|---|
| 1 | 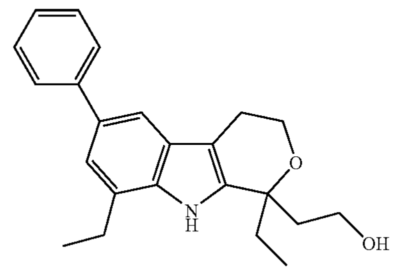 |
| 2 | 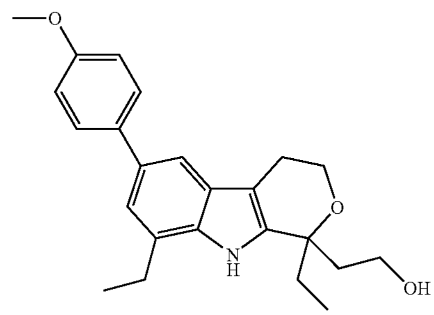 |
| 3 | 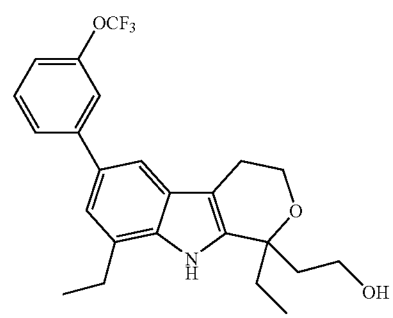 |
| 4 | 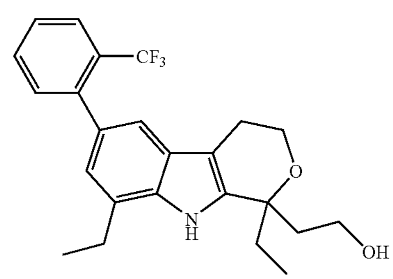 |
| 5 | 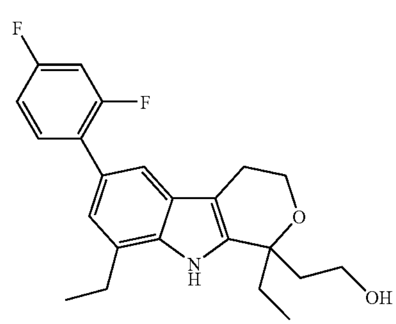 |

-continued

| NO. | STRUCTURE |
|---|---|
| 6 | (4-pyridyl-substituted tricyclic structure with ethyl and hydroxyethyl groups) |
| 7 | (4-fluorophenyl-substituted tricyclic structure) |
| 8 | (3-aminophenyl-substituted tricyclic structure) |
| 9 | (benzo[1,3]dioxol-5-yl-substituted tricyclic structure) |
| 10 | (3,4-difluorophenyl-substituted tricyclic structure) |

-continued

| NO. | STRUCTURE |
|---|---|
| 11 | (5-chlorothiophen-2-yl-substituted tricyclic structure) |
| 12 | (isopropyl and phenyl-substituted tricyclic structure) |
| 13 | (isopropyl and 3-cyanophenyl-substituted tricyclic structure) |
| 14 | (isopropyl and 2-methoxy-5-bromophenyl-substituted tricyclic structure) |
| 15 | (isopropyl and 2-fluorobiphenyl-substituted tricyclic structure) |

-continued

| NO. | STRUCTURE |
|---|---|
| 16 | 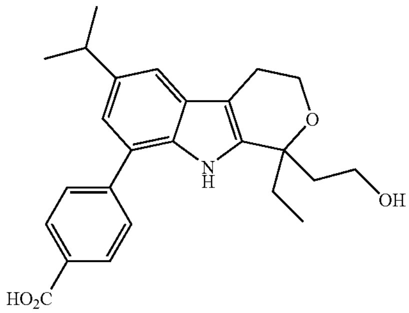 |
| 17 | 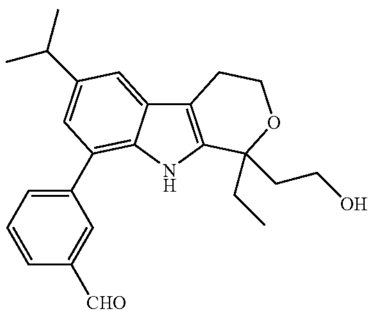 |
| 18 | 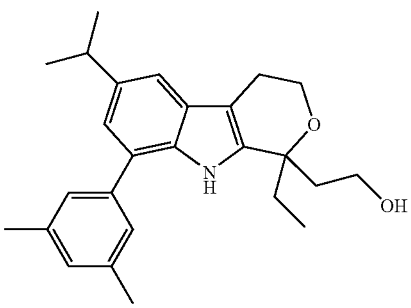 |
| 19 | 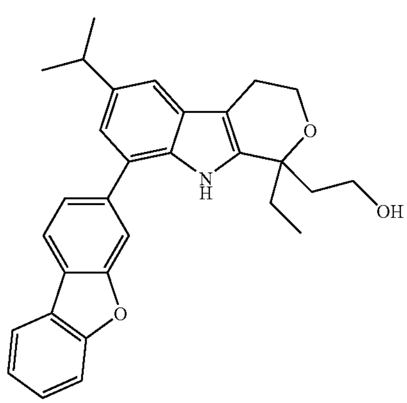 |

-continued

| NO. | STRUCTURE |
|---|---|
| 20 | 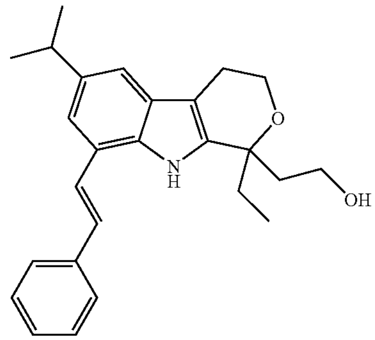 |
| 21 | 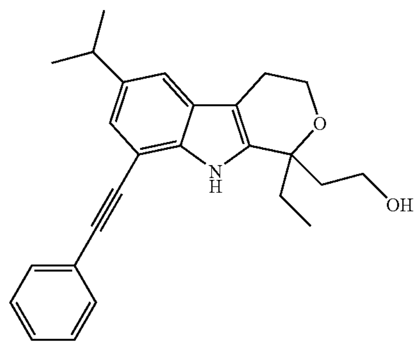 |
| 22 | 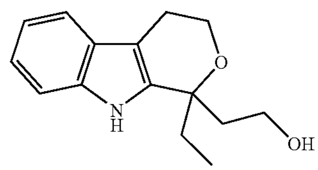 |
| 23 | 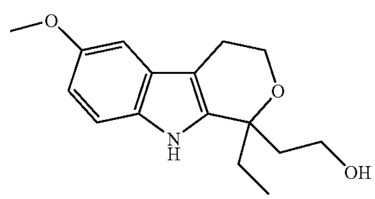 |
| 24 | 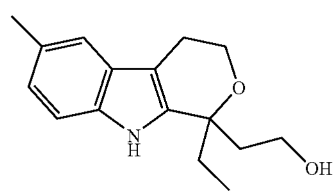 |
| 25 | 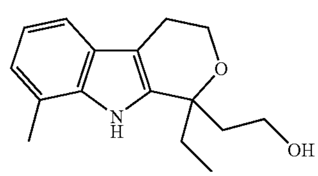 |

| NO. | STRUCTURE |
|---|---|
| 26 | (8-fluoro pyranoindole with 1-ethyl, 1-(2-hydroxyethyl)) |
| 27 | (8-chloro pyranoindole with 1-ethyl, 1-(2-hydroxyethyl)) |
| 28 | (8-bromo pyranoindole with 1-ethyl, 1-(2-hydroxyethyl)) |
| 29 | (8-ethyl pyranoindole with 1-methyl, 1-(2-hydroxyethyl)) |
| 30 | (8-ethyl pyranoindole with 1-propyl, 1-(2-hydroxyethyl)) |
| 31 | (8-ethyl pyranoindole with 1-isopropyl, 1-(2-hydroxyethyl)) |
| 32 | (8-ethyl pyranoindole with 1-phenyl, 1-(2-hydroxyethyl)) |
| 33 | (8-ethyl pyranoindole with 1-ethyl, 1-(N-methylcarbamoylmethyl)) |
| 34 | (8-ethyl pyranoindole spiro-cyclohexane with CH2OH) |
| 35 | (8-ethyl pyranoindole with 1-ethyl, 1-(2-hydroxyethyl), stereo) |
| 36 | (8-isopropyl pyranoindole with 1-ethyl, 1-(2-hydroxyethyl)) |
| 37 | (8-trifluoromethyl pyranoindole with 1-ethyl, 1-(2-hydroxyethyl)) |
| 38 | (5-chloro pyranoindole with 1-ethyl, 1-(2-hydroxyethyl)) |
| 39 | (5-fluoro pyranoindole with 1-ethyl, 1-(2-hydroxyethyl)) |
| 40 | (6-fluoro pyranoindole with 1-ethyl, 1-(2-hydroxyethyl)) |

-continued
| NO. | STRUCTURE |
|---|---|
| 41 | 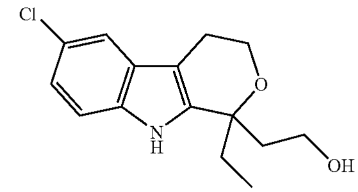 |
| 42 | 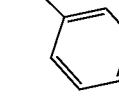 |
| 43 | 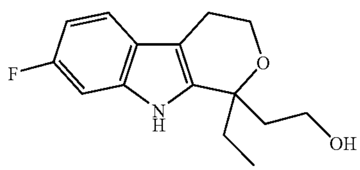 |
| 44 | 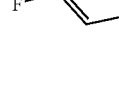 |
| 45 | 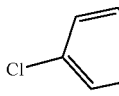 |
| 46 | 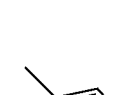 |
| 47 | 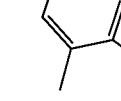 |
| 48 | 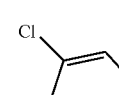 |
-continued
| NO. | STRUCTURE |
|---|---|
| 49 | 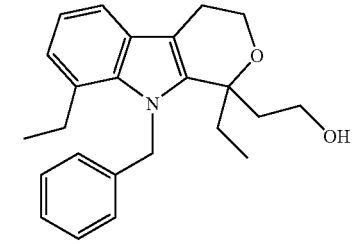 |
| 50 | 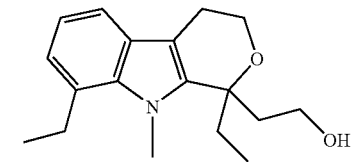 |
| 51 | 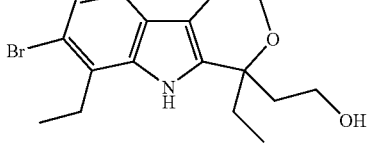 |
| 52 | 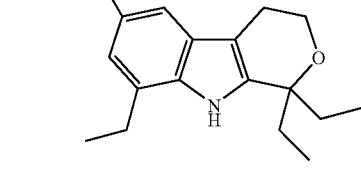 |
| 53 | 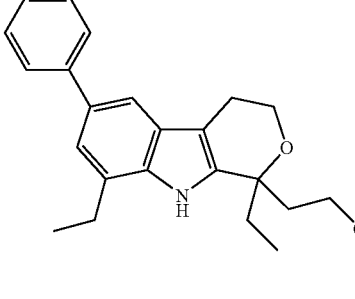 |
| 54 | 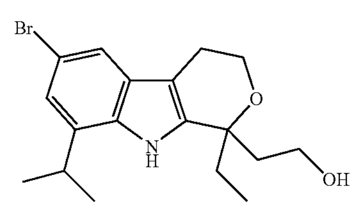 |

-continued

| NO. | STRUCTURE |
|-----|-----------|
| 55 | 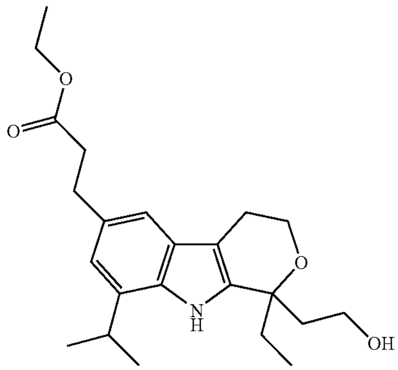 |
| 56 | 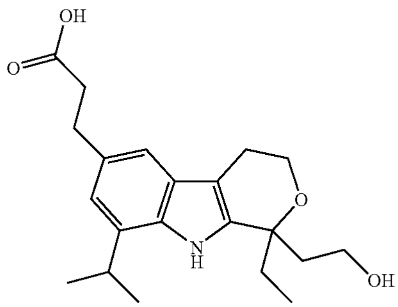 |
| 57 | | or pharmaceutically acceptable salts thereof.

Pharmaceutical compositions comprising a therapeutically effective amount of a prodrug, active metabolite, or pharmaceutically acceptable salt of a compound of Formula I, as well as pharmaceutically acceptable salts of such active metabolites, are also provided herein.

Methods of treating a neoplasia comprising administering to a subject in need thereof a therapeutically effective amount of a composition comprising a compound of Formula I are provided herein. In some embodiments, the neoplasia is a hematological cancer. In other embodiments, the neoplasia is selected from leukemias such as chronic lymphocytic leukemia, myelomas such as multiple myeloma, and lymphomas. In still other embodiments, the cancer is selected from brain cancer, bone cancer, basal cell carcinoma, adenocarcinoma, gastrointestinal cancer, lip cancer, mouth cancer, esophageal cancer, small bowel cancer, stomach cancer, colon cancer, liver cancer, bladder cancer, pancreas cancer, ovary cancer, cervical cancer, lung cancer, breast cancer, skin cancer, prostate cancer, and renal cell carcinoma.

Methods for treating cancer by administering a composition comprising a therapeutically effective amount of a composition of Formula I given in combination with another antineoplastic agent are provided herein. In some embodiments, the antineoplastic agent is an alkylating agent. In other embodiments, the alkylating agent is selected from the group consisting of bendamustine, chlorambucil, cyclophosphamide and melphalan. In still other embodiments, the antineoplastic agent is a glucocorticoid. In yet other embodiments, the glucocoritcoid is prednisone. In some embodiments, the glucocorticoid is given in combination with additional antineoplastic agents.

Methods for treating a disease mediated by β-catenin in a subject in need of such therapy wherein a therapeutically effective amount of a compound of Formula I is administered to the subject, are provided herein.

Methods for treating a disease mediated by Cyclin D1 in a subject in need of such therapy wherein a therapeutically effective amount of a compound of Formula I is administered to the subject, are also provided herein.

Methods for reducing or preventing the development of Alzheimer's disease comprising administering to a subject in thereof a therapeutically effective amount of a composition comprising a compound of Formula I are provided herein. In some embodiments, the method comprises administering to a mammal in need of such treatment a therapeutically effective amount of: (a) at least one compound, pharmaceutically acceptable salt, pharmaceutically acceptable prodrug, or pharmaceutically active metabolite of Formula I; and (b) at least one agent selected from the group consisting of estrogen, risperidone, a thiobenzodiazepine, ampakine, [N-(2,6-dimethylphenyl)-2-(2-oxo-1-pyrrolidinyl)acetamide, DM9384, a cholinesterase inhibitor, donepezil hydrochloride, rivastigmine tartrate, galantamine, NGF, and metrifonate.

Methods for treating a disease in a mammal treatable by administration of a COX-1 and/or COX-2 inhibitor comprising administering to the mammal a therapeutically effective amount of a compound of Formula I which inhibits one or both of COX-1 or COX-2 are provided herein. In some embodiments, the disease is an inflammatory disease.

Methods for treating a hyperplastic disease in a mammal comprising administration to the mammal a therapeutically effective amount of a compound of Formula I are provided herein.

Methods for inhibiting or delaying the onset of a neoplasia in a mammal in need of such treatment comprising administration to the mammal a therapeutically effective amount of a compound of Formula I are provided herein. In some embodiments, the neoplasia is selected from the group consisting of adenomatous polyps, gastrointestinal cancer, liver cancer, bladder cancer, cervical cancer, prostate cancer, lung cancer, breast cancer, and skin cancer.

Methods for treating, inhibiting or delaying the onset of uncontrolled or abnormal angiogenesis in a subject in need of such treatment, inhibition or delay, wherein the uncontrolled or abnormal angiogenesis is selected from the group consisting of metastasis, corneal graft rejection, ocular neovascularization, retinal neovascularization, diabetic retinopathy, retrolental fibroplasia, neovascular glaucoma, gastric ulcer, infantile hemaginomas, angiofibroma of the nasopharynx, avascular necrosis of bone, and endometriosis, and the method comprises treating the subject with a therapeutically effective amount of a compound of Formula I are provided herein.

Pharmaceutical compositions for the treatment of one or more conditions selected from the group consisting of arthritis, fever, common cold, dysmenorrhea, menstrual cramps, inflammatory bowel disease, Crohn's disease, emphysema, acute respiratory distress syndrome, asthma, bronchitis, chronic obstructive pulmonary disease, Alzheimer's disease, organ transplant toxicity, cachexia, allergic reactions, allergic contact hypersensitivity, cancer, tissue ulceration, peptic ulcers, gastritis, regional enteritis, ulcerative colitis, diverticulitis, recurrent gastrointestinal lesion, gastrointestinal bleeding, coagulation, anemia, synovitis, gout, ankylosing spondylitis, restenosis, periodontal disease, epidermolysis bullosa, osteoporosis, loosening of artificial joint implants, atherosclerosis, aortic aneurysm, periarteritis nodosa, congestive heart failure, myocardial infarction, stroke, cerebral ischemia, head trauma, spinal cord injury, neuralgia, neuro-degenerative disorders, autoimmune disorders, Huntington's disease, Parkinson's disease, migraine, depression, peripheral neuropathy, pain, gingivitis, cerebral amyloid angiopathy, nootropic or cognition enhancement, amyotrophic lateral sclerosis, multiple sclerosis, ocular angiogenesis, corneal injury, macular degeneration, conjunctivitis, abnormal wound healing, muscle or joint sprains or strains, tendonitis, skin disorders, myasthenia gravis, polymyositis, myositis, bursitis, bums, diabetes, tumor invasion, tumor growth, tumor metastasis, corneal scarring, scleritis, immunodeficiency diseases, sepsis, premature labor, hypoprothrombinemia, hemophilia, thyroiditis, sarcoidosis, Behcet's syndrome, hypersensitivity, schizophrenia, kidney disease, Rickettsial infections, Protozoan diseases, reproductive disorders, obesity, and septic shock in a mammal, comprising an effective amount of a compound of Formula I or a pharmaceutically acceptable salt thereof effective in such treatments and a pharmaceutically acceptable carrier are provided herein.

Methods of treating a neoplasia in a subject in need of treatment where the subject is treated with a composition comprising a compound of Formula I. Neoplasms that can be treated include, but are not limited to, hematological cancers, such as leukemias, myelomas and lymphomas, brain cancer, bone cancer, epithelial cell derived neoplasia (epithelial carcinoma) such as basal cell carcinoma, adenocarcinoma, gastrointestinal cancer such as lip cancer, mouth cancer, esophageal cancer, small bowel cancer, stomach cancer, colon cancer, liver cancer, bladder cancer, pancreas cancer, ovary cancer, cervical cancer, lung cancer, breast cancer, skin cancer such as squamous cell and basal cell cancers, prostate cancer, renal cell carcinoma, and other known cancers that effect epithelial cells throughout the body and cancers of the bone marrow.

Methods for treating one or more conditions selected from the group consisting of arthritis, fever, common cold, dysmenorrhea, menstrual cramps, inflammatory bowel disease, Crohn's disease, emphysema, acute respiratory distress syndrome, obesity, asthma, bronchitis, chronic obstructive pulmonary disease, Alzheimer's disease, organ transplant toxicity, cachexia, allergic reactions, allergic contact hypersensitivity, cancer, tissue ulceration, peptic ulcers, gastritis, regional enteritis, ulcerative colitis, diverticulitis, recurrent gastrointestinal lesion, gastrointestinal bleeding, coagulation, anemia, synovitis, gout, ankylosing spondylitis, restenosis, periodontal disease, epidermolysis bullosa, osteoporosis, loosening of artificial joint implants, atherosclerosis, aortic aneurysm, periarteritis nodosa, congestive heart failure, myocardial infarction, stroke, cerebral ischemia, head trauma, spinal cord injury, neuralgia, neuro-degenerative disorders, autoimmune disorders, Huntington's disease, Parkinson's disease, migraine, depression, peripheral neuropathy, pain, gingivitis, cerebral amyloid angiopathy, nootropic or cognition enhancement, amyotrophic lateral sclerosis, multiple sclerosis, ocular angiogenesis, corneal injury, macular degeneration, conjunctivitis, abnormal wound healing, muscle or joint sprains or strains, tendonitis, skin disorders, myasthenia gravis, polymyositis, myositis, bursitis, bums, diabetes, tumor invasion, tumor growth, tumor metastasis, corneal scarring, scleritis, immunodeficiency diseases, sepsis, premature labor, hypoprothrombinemia, hemophilia, thyroiditis, sarcoidosis, Behcet's syndrome, hypersensitivity, schizophrenia, kidney disease, Rickettsial infections, Protozoan diseases, reproductive disorders, and septic shock in a mammal, comprising administering to said mammal a therapeutically effective amount of a compound of Formula I or a pharmaceutically acceptable salt thereof effective in treating such a condition, are provided herein.

In some embodiments, methods for treating a hyperplastic disease in a mammal by administering to the mammal a therapeutically effective amount of a compound of Formula I.

In other embodiments, methods for treating, inhibiting, or delaying the onset of uncontrolled or abnormal angiogenesis in a subject in need of such treatment, inhibition, or delay by administering a therapeutically effective amount of a compound of Formula I, are provided. In one embodiment of this method, the uncontrolled or abnormal angiogenesis to be treated is selected from the group including, but not limited to, metastasis, corneal graft rejection, ocular neovascularization, retinal neovascularization, diabetic retinopathy, retrolental fibroplasia, neovascular glaucoma, gastric ulcer, infantile hemaginomas, angiofibroma of the nasopharynx, avascular necrosis of bone, and endometriosis.

In still other embodiments, methods for selecting a subject for treatment of a disease or condition mediated by β-catenin where the method involves obtaining a sample of the subject's tumor, determining if β-catenin is activated in the tumor, and treating the subject with an agent that modulates β-catenin activity. In one related method, β-catenin activation is determined with immunohistochemical methods.

In still other embodiments, methods for selecting a subject for treatment of a disease or condition mediated by Cyclin D1 where the method involves obtaining a sample of the subject's tumor, determining if Cyclin D1 is overexpressed in the tumor, and treating the subject with an agent that modulates Cyclin D1 activity. Preferred compounds for use in the method are compounds of Formula I. In one related method, Cyclin D1 overexpression is determined using quantitative PCR.

DETAILED DESCRIPTION OF THE INVENTION

Figure 1:
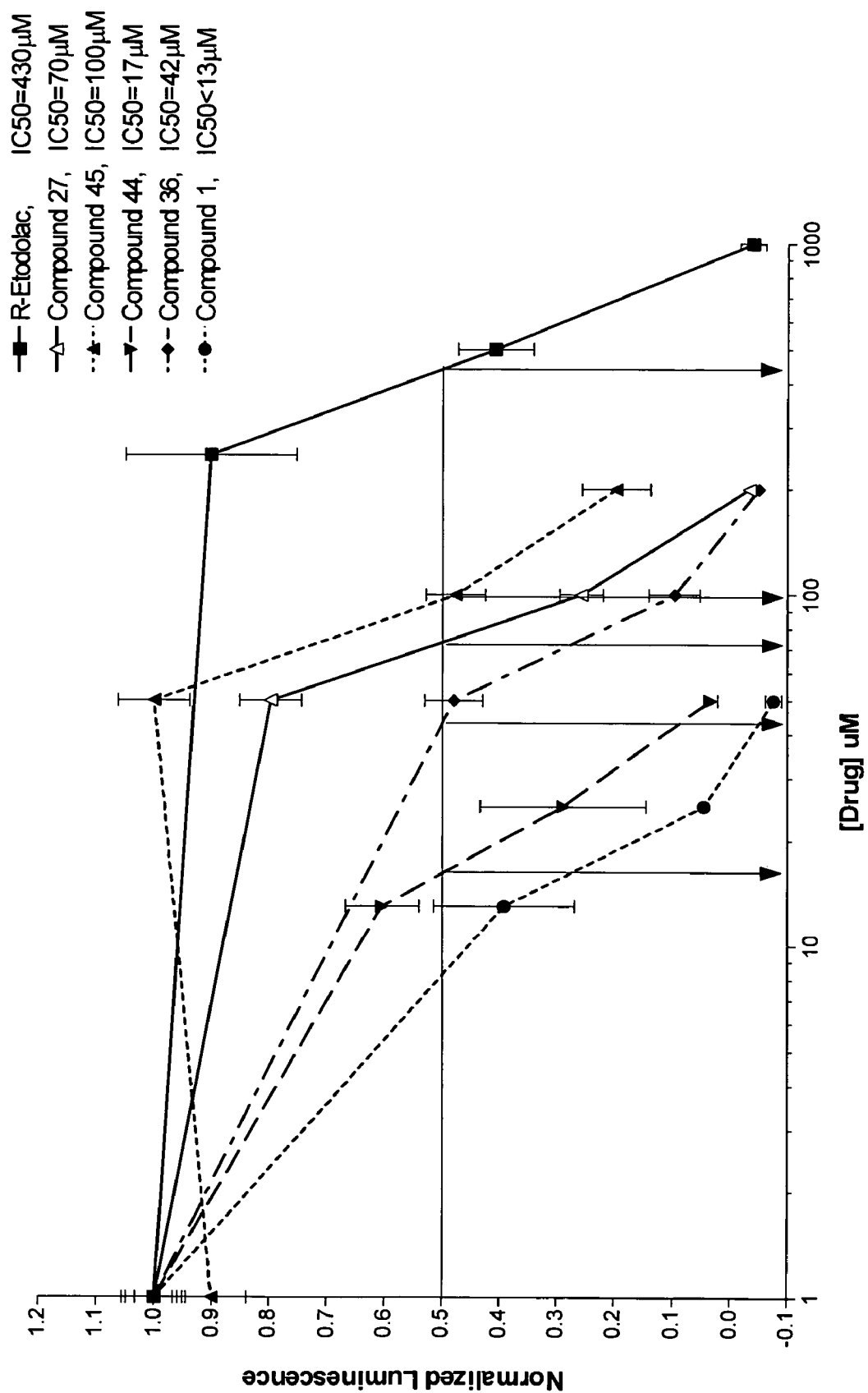
FIG. 1 shows inhibition of β-catenin:TOP flash by R-etodolac and compounds of the invention.

To more readily facilitate an understanding of the invention and its preferred embodiments, the meanings of terms used herein will become apparent from the context of this specification in view of common usage of various terms and the explicit definitions of other terms provided in the glossary below or in the ensuing description.

Glossary of Terms

As used herein, the terms "comprising," "including," and "such as" are used in their open, non-limiting sense.

As used herein and in the appended claims, the singular forms "a", "an", and "the" include plural reference unless the context clearly dictates otherwise.

In accordance with a convention used in the art,  is used in structural formulae herein to depict the bond that is the point of attachment of the moiety or substituent to the core or backbone structure.

In accordance with a convention used in the art, the symbol  represents a methyl group,  represents an ethyl group,

represents a cyclopentyl group, etc.

The term "alkyl" as used herein refers to a straight- or branched-chain alkyl group having one to twelve carbon atoms. Exemplary alkyl groups include methyl (Me), ethyl (Et), n-propyl, isopropyl, butyl, isobutyl, sec-butyl, tert-butyl (tBu), pentyl, isopentyl, tert-pentyl, hexyl, isohexyl, and the like. The term "lower alkyl" designates an alkyl having from 1 to 6 carbon atoms (a $C_{1-6}$-alkyl).

The term "heteroalkyl" as used herein refers to straight- and branched-chain alkyl groups having from one to twelve atoms containing one or more heteroatoms selected from S, O, and N. The term "lower heteroalkyl" designates a heteroalkyl having from 1 to 6 carbon atoms (a $C_{1-6}$-heteroalkyl).

The term "alkenyl" means an alkyl radical having one or more double bonds and two to twelve carbon atoms. Alkenyl groups containing three or more carbon atoms may be straight or branched. Alkenyl groups as used herein include either the cis or trans configurations. Illustrative alkenyl groups include prop-2-enyl, but-2-enyl, but-3-enyl, 2-methylprop-2-enyl, hex-2-enyl, and the like. The term "lower alkenyl" designates an alkyl having from 1 to 6 carbon atoms (a $C_{1-6}$-alkenyl).

The term "allyloxy" refers to an alkenyloxy group which is $CH_2=CHCH_2-O-$.

The term "alkynyl" means an alkyl radical having one or more triple bonds and two to twelve carbon atoms. Alkynyl groups containing three or more carbon atoms may be straight or branched. Alkynyl groups as used herein include either the cis or trans configurations. Illustrative alkynyl groups include prop-2-ynyl, but-2-ynyl, but-3-ynyl, 2-methylbut-2-ynyl, hex-2-ynyl, and the like. The term "lower alkynyl" designates an alkyl having from 1 to 6 carbon atoms (a $C_{1-6}$-alkynyl).

The term "aryl" (Ar) refers to a monocyclic, or fused or spiro polycyclic, aromatic carbocycle (ring structure having ring atoms that are all carbon) having from three to twelve ring atoms per ring. Illustrative examples of aryl groups include the following moieties:

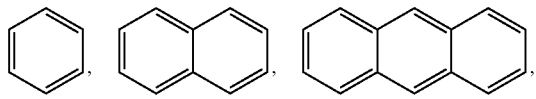

-continued

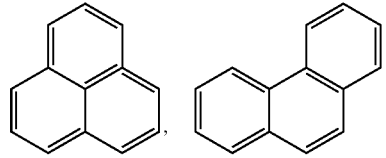

, and the like.

The term "heteroaryl" (heteroAr) refers to a monocyclic, or fused or Spiro polycyclic, aromatic heterocycle (ring structure having ring atoms selected from carbon atoms as well as nitrogen, oxygen, and sulfur heteroatoms) having from three to twelve ring atoms per ring. Illustrative examples of heteroaryl groups include the following moieties:

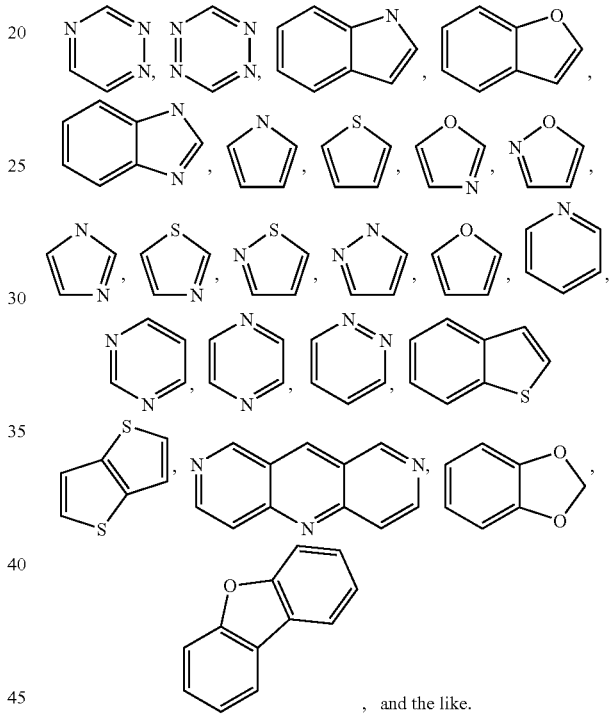

, and the like.

The term "cycloalkyl" refers to a saturated or partially saturated, monocyclic or fused or spiro polycyclic, carbocycle having from three to twelve ring atoms per ring. Illustrative examples of cycloalkyl groups include the following moieties:

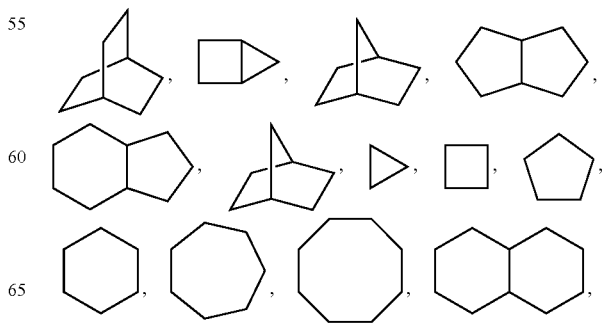

-continued

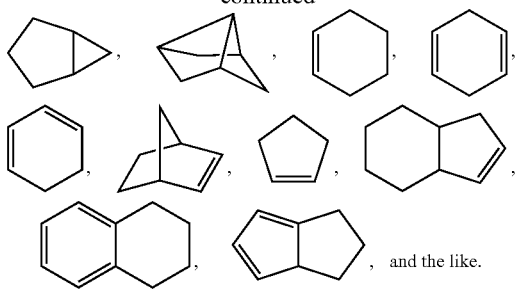

A "heterocycloalkyl" refers to a monocyclic, or fused or Spiro polycyclic, ring structure that is saturated or partially saturated and has from three to twelve ring atoms per ring selected from C atoms and N, O, and S heteroatoms. Illustrative examples of heterocycloalkyl groups include:

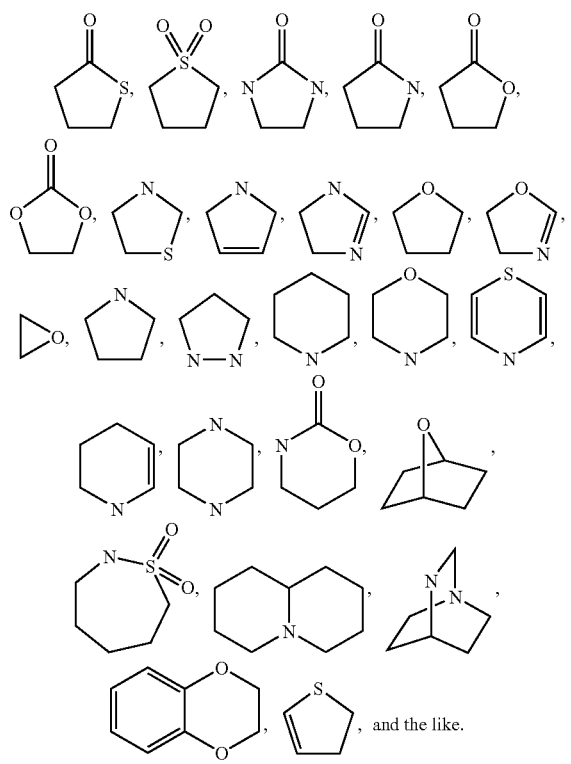

, and the like.

The term "alkoxy" refers to O-alkyl. Illustrative examples include methoxy, ethoxy, propoxy, and the like.

The term "halogen" represents chlorine, fluorine, bromine or iodine. The term "halo" represents chloro, fluoro, bromo or iodo.

Unless otherwise defined, the term "substituted" as used herein means at least one hydrogen atom is replaced with a suitable substituent.

The term "unsubstituted" means that the specified group bears no substituents.

The term "lower" when referring to a group such as an alkyl, alkenyl, alkynyl, alkoxy or other group refers to such a group having up to 6 carbon atoms.

As used herein "tumors" or "neoplasms" include growths of tissue cells wherein multiplication of cells is uncontrolled and progressive. Some such growths are benign, but others are termed malignant and can lead to death of the organism. Malignant neoplasms, or cancers are distinguished from benign growths in that in addition to exhibiting aggressive cellular proliferation can invade surrounding tissues and metastasize. Malignant neoplasms may be characterized by showing a greater loss of differentiation and organization relative to one another and surrounding tissues. "Hyperplasia" refers to the abnormal multiplication or increase in the number of normal cells in normal arrangement in a tissue.

The term "subject" for purposes of treatment includes any human or animal subject who has any one of the known diseases or conditions described herein, e.g., cancer, hyperplasia, inflammation, Alzheimer's, and abnormal angiogenesis. For methods of prevention, the subject is any human or animal subject, and preferably is a human subject who is at risk for the disease or conditions described herein, e.g., cancer. The subject may be at risk due to a genetic predisposition, and/or exposure to various agents, including chemicals and viral agents. Besides being useful for human treatment, the compounds described herein are also useful for veterinary treatment of mammals, including companion animals and farm animals, such as horses, dogs, cats, cows, sheep and pigs. Preferably, subject means a human.

As used herein "a disease mediated by β-catenin" means a disease that is associated with changes in β-catenin regulation such that the its levels, distribution and/or association with other proteins in the cytoplasm and nucleus differ from that found in normal cells. Changes in β-catenin levels, associations, and/or distribution, e.g., nuclear accumulation may result from mutations in β-catenin, APC, axin or other proteins involved in the trafficking of β-catenin. β-catenin accumulation, levels and/or distribution may also be affected by changes in the wnt/fzd signaling pathway. β-catenin accumulation in the nucleus may lead to the transcription of genes involved in tumorgenesis, such as cyclin D1 and c-myc.

As used herein "activated β-catenin" represents β-catenin that is not marked for degradation.

As used herein "a disease mediated by Cyclin D1" means a disease that is associated with changes in Cyclin D1 expression such that the its levels, distribution and/or association with other proteins in the cell differ from that found in normal cells.

As used herein "angiogenesis" is the development of new blood vessels into a tissue or organ. Under normal conditions, angiogenesis is observed in wound healing and embryonal development. Uncontrolled or abnormal angiogenesis is associated with neoplastic disease, tumor metastasis and other angiogenesis-related diseases. "A pharmaceutically acceptable salt" is intended to mean a salt that retains the biological effectiveness of the free acids and bases of the specified compound and that is not biologically or otherwise undesirable.

As used herein a "pharmaceutically acceptable prodrug" is a compound that may be converted under physiological conditions or by solvolysis to the specified compound or to a pharmaceutically acceptable salt of such compound.

The term "a pharmaceutically active metabolite" is intended to mean a pharmacologically active product produced through metabolism in the body of a specified compound or salt thereof.

An "effective amount" is intended to mean that amount of an agent that, when administered to a subject in need of such treatment, is sufficient to effect treatment for a disease and/or condition associated with β-catenin, COX, PPAR, Cyclin D and/or Aβ42. Thus, e.g., a therapeutically effective amount of a compound of the Formula I, salt, active metabolite or prodrug thereof is a quantity sufficient to modulate, regulate, or inhibit the activity of β-catenin, COX, PPAR, Cyclin D and/or Aβ42 such that a disease and/or condition which is mediated by that activity is reduced or alleviated.

The terms "treating", "treat" and "treatment" refer to any treatment of a COX, β-catenin, PPAR, or amyloid-β mediated disease and/or condition in a mammal, particularly a human, and include: (i) preventing the disease or condition from occurring in a subject which may be predisposed to the condition, for example subjects with accumulated Aβ peptides, such that the treatment constitutes prophylactic treatment for the pathologic condition; (ii) modulating or inhibiting the disease or condition, i.e., arresting its development; (iii) relieving the disease or condition, i.e., causing regression of the disease or condition; or (iv) relieving and/or alleviating disease or condition or the symptoms resulting from the disease or condition, e.g., relieving an inflammatory response without addressing the underlining disease or condition.

By "efficacious levels" is meant levels in which the effects of β-catenin, COX, PPAR, Cyclin D and/or Aβ42 activity or amounts are, at a minimum, regulated.

The phrase "conjunctive therapy" (or "combination therapy"), in defining use of a compound of the invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations for each agent.

Compounds

Applicants have discovered compounds, as represented by Formulas I, which possess COX inhibitory activity, β-catenin inhibitory activity, cyclin D1 activity, and/or are cytotoxic to cancer cell lines.

Provided herein are compounds represented by Formulas I:

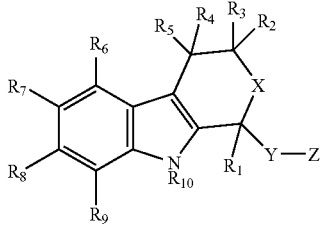

Formula I or a pharmaceutically acceptable prodrug, pharmaceutically active metabolite, or pharmaceutically acceptable salt thereof, wherein $R_1$-$R_{10}$, X, Y, Z and n are as defined herein.

The compounds of Formula I may exhibit the phenomenon of tautomerism. While Formulas I cannot expressly depict all possible tautomeric forms, it is to be understood that Formula I are intended to represent any tautomeric form of the depicted compound and are not to be limited merely to a specific compound form depicted by the formula drawings.

The compounds of Formula I may have one or more asymmetric centers depending upon the nature of the various substituents on the molecule. As a consequence of these asymmetric centers, the compounds of Formulas I may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. The compounds of the present invention can be used in a form that is at least 90% optically pure, that is, a form that contains at least 90% of a single isomer (80% enantiomeric excess ("e.e.") or diastereomeric excess ("d.e.")). In some cases, e.g., to reduce toxicity, the compounds can be used in a form that contains at least 95% (90% e.e. or d.e.), even more preferably at least 97.5% (95% e.e. or d.e.), and most preferably at least 99% (98% e.e. or d.e.) of a single isomer e.e. or d.e.

Additionally, Formula I are intended to cover solvated as well as unsolvated forms of the identified structures. For example, Formula I include compounds of the indicated structure in both hydrated and non-hydrated forms. Other examples of solvates include the structures in combination with isopropanol, ethanol, methanol, DMSO, ethyl acetate, acetic acid, or ethanolamine.

In addition to compounds of Formula I, the invention includes pharmaceutically acceptable prodrugs, pharmaceutically active metabolites, and pharmaceutically acceptable salts of such compounds and metabolites.

Prodrugs and active metabolites of a compound may be identified using routine techniques known in the art. See, e.g., Bertolini et al., *J. Med. Chem.*, 40, 2011-2016 (1997); Shan, et al., *J. Pharm. Sci.*, 86 (7), 765-767; Bagshawe, *Drug Dev. Res.*, 34, 220-230 (1995); Bodor, *Advances in Drug Res.*, 13, 224-331 (1984); Bundgaard, *Design of Prodrugs* (Elsevier Press 1985); Larsen, *Design and Application of Prodrugs*, Drug Design and Development (Krogsgaard-Larsen et al., eds., Harwood Academic Publishers, 1991); Dear et al., *J. Chromatogr. B*, 748, 281-293 (2000); Spraul et al., *J. Pharmaceutical & Biomedical Analysis*, 10, 601-605 (1992); and Prox et al., *Xenobiol.*, 3, 103-112 (1992).

A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, g-hydroxybutyrates, glycolates, tartrates, methane-sulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

Therapeutically effective amounts of the agents of the invention may be used to treat or prevent diseases and/or conditions mediated by modulation or regulation of β-catenin, COX, Aβ42, and PPAR.

The amount of a given agent that will correspond to such an amount will vary depending upon factors such as the particular compound, disease condition and its severity, the identity (e.g., weight) of the subject in need of treatment, but can nevertheless be routinely determined by one skilled in the art.

The active agents of the invention may be formulated into pharmaceutical compositions as described below. Pharmaceutical compositions of this invention comprise an effective modulating, regulating, or inhibiting amount of a compound of Formula I and an inert, pharmaceutically acceptable carrier or diluent. In one embodiment of the pharmaceutical compositions, efficacious levels of the inventive agents are provided so as to provide therapeutic benefits involving modulation of β-catenin, COX, PPAR, and/or Aβ42. These compositions are prepared in unit-dosage form appropriate for the mode of administration, e.g., parenteral or oral administration.

An inventive agent can be administered in conventional dosage form prepared by combining a therapeutically effective amount of an agent (e.g., a compound of Formula I) as an active ingredient with appropriate pharmaceutical carriers or diluents according to conventional procedures. These procedures may involve mixing, granulating and compressing or dissolving the ingredients as appropriate to the desired preparation.

The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent is dissolved in an aqueous solution of an organic or inorganic acid, such as 0.3M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, gylcerin and the like in concentrations ranging from 0-60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

It will be appreciated that the actual dosages of the agents used in the compositions of this invention will vary according to the particular complex being used, the particular composition formulated, the mode of administration and the particular site, host and disease and/or condition being treated. Optimal dosages for a given set of conditions can be ascertained by those skilled in the art using conventional dosage-determination tests in view of the experimental data for an agent. For oral administration, an exemplary daily dose generally employed is from about 0.001 to about 3000 mg/kg of body weight, with courses of treatment repeated at appropriate intervals. In some embodiments, the daily dose is from about 1 to 3000 mg/kg of body weight.

Typical daily doses in a pateint may be anywhere between about 500 mg to about 3000 mgs, given once or twice daily, e.g., 3000 mg can be given twice daily for a total dose of 6000 mg. In one embodiment, the dose is between about 1000 to about 3000 mgs. In another embodiment, the dose is between about 1500 to about 2800 mgs. In other embodiments, the dose is between about 2000 to about 3000 mgs.

Plasma concentrations in the subjects may be between about 100 µM to about 1000 µM. In some embodiments, the plasma concentration may be between about 200 µM to about 800 µM. In other embodiments, the concentration is about 300 µM to about 600 µM. In still other embodiments the plasma concentration may be between about 400 to about 800 µM. Administration of prodrugs is typically dosed at weight levels, which are chemically equivalent to the weight levels of the fully active form.

The compositions of the invention may be manufactured using techniques generally known for preparing pharmaceutical compositions, e.g., by conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations, which can be used pharmaceutically.

Proper formulation is dependent upon the route of administration chosen. For injection, the agents of the invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations, which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents, which increase the solubility of the compounds to allow for the preparation of highly concentrated solutions.

Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

An exemplary pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

The administration of the present invention may be for either prevention or treatment purposes. When used for the treatment and/or prevention of neoplasia, or Alzheimer's, or for the treatment of diseases treatable by inhibiting COX, the methods and compositions described herein may be used alone or in conjunction with additional therapies known to those skilled in the art. Alternatively, the methods and compositions described herein may be used as conjunctive therapy. By way of example, the compounds described herein may be administered alone or in conjunction with other antineoplastic agents, glucocorticoids or other growth inhibiting agents or other drugs or nutrients.

There are large numbers of antineoplastic agents available in commercial use, in clinical evaluation and in pre-clinical development, which could be selected for treatment of neoplasia by combination drug chemotherapy. Such antineoplastic agents fall into several major categories, namely, antibiotic-type agents, alkylating agents, antimetabolite agents, hormonal agents, including glucocorticoids such as prednisone and dexamethasone, immunological agents, interferon-type agents and a category of miscellaneous agents. Alternatively, other anti-neoplastic agents, such as metallomatrix proteases (MMP), SOD mimics or alphav beta$_3$ inhibitors may be used.

One family of antineoplastic agents which may be used in combination with the compounds of the inventions consists of antimetabolite-type antineoplastic agents. Suitable antimetabolite antineoplastic agents may be selected from the group consisting of alanosine, AG2037 (Pfizer), 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-18801 1, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT and uricytin.

A second family of antineoplastic agents which may be used in combination with the compounds of the invention consists of alkylating-type antineoplastic agents. Suitable alkylating-type antineoplastic agents may be selected from the group consisting of Shionogi 254-S, aldo-phosphamide analogues, altretamine, anaxirone, Boehringer Mannheim BBR-2207, bendamustine, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, melphalan, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromustine, Tanabe Seiyaku TA-077, tauromustine, temozolomide, teroxirone, tetraplatin and trimelamol.

Another family of antineoplastic agents which may be used in combination with the compounds of the invention consists of antibiotic-type antineoplastic agents. Suitable antibiotic-type antineoplastic agents may be selected from the group consisting of Taiho 4181-A, aclarubicin, actinomycin D, actinoplanone, alanosine, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-1 02, Kyowa Hakko DC-79, Kyowa Hakko DC-88A, Kyowa Hakko DC89-Al, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-Al, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SR$_1$ International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with the compounds of the invention include a miscellaneous family of antineoplastic agents selected from the group consisting of alpha-carotene, alpha-difluoromethyl-arginine, acitretin, arsenic trioxide, Avastin® (bevacizumab), Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-ll, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, elliprabin, elliptinium acetate, epothionesTsumura EPMTC, erbitux, ergotamine, erlotnib, etoposide, etretinate, fenretinide, Fujisawa FR-57704, gallium nitrate, genkwadaphnin, Glivec ® (imatnib), Chugai GLA-43, Glaxo GR-63178, gefitinib, grifolan NMF-5N, hexadecylphosphocholine, Green Cross HO-221, homoharringtonine, hydroxyurea, BTG ICRF-187, indanocine, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, mefloquine, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, Rituxan® (and other anti CD20 antibodies, e.g. Bexxar®, Zevalin®), SmithKline SK&F-104864, statins (Lipitor® etc.), Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Thalidomide, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534, zometa.

Examples of radioprotective agents which may be used in the combination chemotherapy of this invention are AD-5, adchnon, amifostine analogues, detox, dimesna, 1-102, MM-159, N-acylated-dehydroalanines, TGF-Genentech, tiprotimod, amifostine, WR-151327, FUT-187, ketoprofen transdermal, nabumetone, superoxide dismutase (Chiron) and superoxide dismutase Enzon.

Methods for preparation of the antineoplastic agents described above may be found in the literature. Methods for preparation of doxorubicin, for example, are described in U.S. Pat. Nos. 3,590,028 and 4,012,448. Methods for preparing metallomatrix protease inhibitors are described in EP 780386. Methods for preparing SOD mimics are described in EP 524,101. Methods for preparing $\alpha_v \beta_3$ inhibitors are described in WO97/08174.

Additionally, the compounds of Formula I may be administered either alone or in combination with other compounds effective for treating Alzheimer's or dementia. For example, the compounds of the invention may be administered in combination with other agents used to treat amyloid-β-mediated diseases or conditions, such as estrogen, risperidone, a thiobenzodiazepine, ampakine, [N-(2,6-dimethylphenyl)-2-(2-oxo-1-pyrrolidinyl)acetamide, DM9384, a cholinesterase inhibitor, donepezil hydrochloride, rivastigmine tartrate, galantamine, NGF, and metrifonate.

COX Inhibitors

The compounds of Formula I described herein or pharmaceutically acceptable salts may possess COX-inhibiting activity and possess anti-inflammatory, antipyretic, analgesic, antithrombotic, and anti-cancer activities. The compounds of Formula I and pharmaceutically acceptable salt thereof, therefore, are useful for treating and/or preventing COX-mediated diseases, inflammatory conditions, pain, fever, rheumatic fever, collagen diseases, autoimmune diseases, various immunological diseases, thrombosis, cancer and neurodegenerative diseases in human beings or animals by using administered systemically or topically. More particularly, the compounds and pharmaceutically acceptable salts thereof are useful for treating and/or preventing inflammation and acute or chronic joint and muscle pain [e.g. rheumatoid arthritis, rheumatoid spondylitis, osteoarthritis, gouty arthritis, juvenile arthritis, etc.], inflammatory skin condition [e.g. sunburn, burns, eczema, dermatitis, etc.], inflammatory eye condition [e.g. conjunctivitis, etc.], lung disorder in which inflammation is involved [e.g. asthma, bronchitis, pigeon fancier's disease, farmer's lung, etc.], conditions of the gastrointestinal tract associated with inflammation [e.g. aphthous ulcer, Crohn's disease, atopic gastritis, gastritis varialoforme, ulcerative colitis, coeliac disease, regional ileitis, irritable bowel syndrome, etc.], gingivitis, inflammation, pain and tumescence after operation or injury, pyrexia, pain and other conditions associated with inflammation, particularly those in which lipoxygenase and cyclooxygenase products are a factor, systemic lupus erythematosus, scleroderma, polymyositis, tendonitis, bursitis, periarteritisnodose, rheumatic fever, Sjogren's syndrome, Behcet disease, thyroiditis, type I diabetes, nephrotic syndrome, aplastic anemia, myasthenia gravis, uveitis contact dermatitis, psoriasis, Kawasaki disease, sarcoidosis, Hodgkin's disease, Alzheimer's disease, Parkinson's disease, symptoms associated with influenza and other viral infections, common cold, low back and neck pain, dysmenorrheal, headache, toothache, sprains and strains, myositis, neuralgia, synovitis, arthritis including rheumatoid arthritis, degenerative joint disease or osteoarthritis, gout, ankylosing spondylitis, bursitis, injuries following surgical and dental procedures, bone loss, or the like. Additionally, the compounds disclosed herein or a salt thereof is expected to be useful as therapeutical and/or preventive agents for cardiovascular or cerebrovascular, diseases, the diseases caused by hyperglycemia and hyperlipemia.

The anti-inflammatory activity of the compounds of this invention may be assayed by measuring the ability of the compound to inhibit COX-1 and COX-2. Techniques for measuring COX inhibition is described herein and in the literature, for example, see U.S. patent application Ser. Ser. No. 2002/0107280; Winter et al. 1962 *Proc. Soc. Exp. Biol. Med.* 111:544 both incorporated herein by reference.

In still other embodiments preferred compounds of Formula 1 are those compound with no or little COX activity.

Cancer

Neoplasms treatable by the present invention include solid tumors, i.e., carcinomas and sarcomas. Carcinomas include malignant neoplasms derived from epithelial cells which infiltrate surrounding tissues and give rise to metastases. Adenocarcinomas are carcinomas derived from glandular tissue, or from tissues that form recognizable glandular structures. Another broad category of cancers includes sarcomas, which are tumors whose cells are embedded in a fibrillar or homogeneous substance, like embryonic connective tissue. The invention also enables treatments of cancer of the myeloid or lymphoid systems, including leukemias, such as CLL, myelomas, such as multiple myeloma, lymphomas, and other cancers that typically are not present as a tumor mass, but are distributed in the vascular or lymphoreticular systems.

Cancers that may be treated using the compounds described herein include, without limitation, brain cancer, bone cancer, epithelial cell derived neoplasia (epithelial carcinoma) such as basal cell carcinoma, adenocarcinoma, gastrointestinal cancer such as lip cancer, mouth cancer, esophageal cancer, small bowel cancer, stomach cancer, colon cancer, liver cancer, bladder cancer, pancreas cancer, ovary cancer, cervical cancer, lung cancer, breast cancer, skin cancer such as squamous cell and basal cell cancers, prostate cancer, renal cell carcinoma, and other known cancers that effect epithelial cells throughout the body.

The activity of compounds of Formula I against various cancers can be tested using assays known in the art, e.g., MTT assay to cancer cell lines in vitro and animal tumor models—see, for example, Romijn et al., 1988 *Prostate* 12:99-110.

Cancers amenable to treatment with the compounds of the invention include those mentioned above and those mediated by β-catenin. Exemplary cancers would include those having mutations in APC, the wnt/fzd signaling pathway, axin and/or β-catenin resulting in β-catenin deregulation and a subsequent increase in free β-catenin in the cytoplasm and nucleus.

The identification of cancers mediated by β-catenin can be determined using a variety of techniques known in the art. For example, the expression of wnt and/or fzd RNA can be measured in cancer cells and compared to normal cells as described in International Publications Nos. WO 02/092635 and WO 02/088081 (both incorporated herein by reference in their entireties). Cancers that overexpress wnt and/or fzd would be expected to have deregulated β-catenin.

Deregulation of β-catenin can also be shown by analyzing the subcellular localization of β-catenin, e.g., cytoplasmic, nuclear and/or plasma membrane in cancer cells as compared to normal cells of the same type. Such characterization can be done using techniques know in the art including immunohistochemistry, confocal microscopy, and immunoblot analysis.

Samples for β-catenin analysis can be obtained using standard procedures know to those of skill in the art and include generally known biopsy methods including fine-needle aspiration, surgical biopsy, and core-needle biopsy. Samples for analysis can also be fixed and embedded in such materials as paraffin.

For a review of immunological and immunoassay procedures in general, see Stites et al. (eds.) (1991) *Basic and Clinical Immunology* (7th ed.). Inmnunoassays to detect β-catenin can be performed in any of several configurations, which are reviewed extensively in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B. V., Amsterdam; and Harlow and Lane *Antibodies, A Laboratory Manual, supra*, each of which is incorporated herein by reference. See also Chan (ed.) (1987) *Immunoassay: A Practical Guide* Academic Press, Orlando, Fla.; Price et al. (eds.) (1997) *Principles and Practice of Immunoassay* ($2^{nd}$ ed), Groves Dictionaries, Inc.; Boenisch (ed.) (2001) *Handbook Immunochemical Staining Methods* DAKO Corp. Carpinteria, Calif., USA; and Ngo (ed.). (1988) *Non-isotopic Immunoassays* Plenum Press, N.Y.; all incorporated herein by reference.

In general, immunoassay design considerations include preparation of antibodies (e.g., monoclonal or polyclonal) having sufficiently high-binding specificity for their antigen so the specifically bound antibody-antigen complex can be distinguished reliably from nonspecific interactions. Polyclonal and monoclonal antibodies that detect β-catenin are known in the art and are commercially available, e.g., Upstate Cell Signaling Solutions, Charlottesville, Va.—catalogue nos. 06-734; 05-601; and 05-482.

Western blot analysis can be used to quantitate the amount of β-catenin protein in a sample. Electrophoresis is carried out, e.g., on a tissue sample suspected of containing the protein. Following electrophoresis to separate the proteins, and transfer of the proteins to a suitable solid support such as a nitrocellulose filter, the solid support is incubated with an antibody reactive with the denatured protein. This antibody may be labeled, or alternatively may be it may be detected by subsequent incubation with a second labeled antibody that binds the primary antibody.

A preferred method for identifying cancers that have deregulated β-catenin is immunohistochemistry (IHC). Immunohistochemistry allows for the evaluation of microanatomical detail and heterogeneity in tissues and tumors. Immunohistochemistry is advantageous over other methods of analyses because it is the only method that can directly localize proteins to individual cell types and specific cell locations, e.g., plasma membrane, cytoplasm, and/or nucleus. Differences among gene expression of normal and tumor tissue can be detected while simultaneously noting the changes in cell number and composition. In contrast, techniques,-such as Western blotting require the use of cell extracts; therefore, a possibility exists of contamination of different cell types. For IHC, a primary β-catenin antibody that recognizes β-catenin protein is introduced to a biological specimen. After incubation with the primary antibody, a wash can be performed to remove unbound antibody. Then, a secondary antibody, directed against the primary antibody and labeled with an enzyme, can be incubated with the biological specimen. During incubation, the secondary antibody will bind to the primary.antibody. Alternatively, the second antibody may lack a label, but it may, in turn, be bound by a labeled third antibody specific to antibodies of the species from which the second antibody is derived.

The primary antibody can be labeled with an enzyme thus eliminating the need for a second antibody. Alternatively, the labeled β-catenin antibody can be labeled with biotin rather than an enzyme. Then, in an additional step, enzyme-labeled avidin or streptavidin is introduced to the sample and allowed to bind to the biotinylated antibody.

For immunohistochemistry, the tissue sample may be fresh or frozen or may be embedded, for example, in paraffin or other waxes, nitrocellulose, carbowax (also known as water soluble polyethylene glycol (see, Gao ed. (1993) "Polyethylene Glycol as an Embedment for Microscopy and Histochemistry," CRC Press, Inc. Boca Raton, Fla.), plastic, including resins such as acrylic and epoxy resins, or OCT embedded frozen blocks. Preferably, the samples are embedded in paraffin or other waxes, nictrocellulose, carbowax, or plastic. The samples can be fixed with a preservative, such as formalin, for example.

Samples for immunohistochemistry can be obtained from surgical biopsies, fine-needle biopsies, fine-needle aspiration biopsies, core-needle biopsies, effusions from body cavities, such as the abdominal cavity, the pleural cavities and the pericardial cavity, and cells collected from other bodily fluids, such as blood and urine and the like. Methods of obtaining such samples are known in the art. For example, an effuision sample can be collected by puncturing the chest wall or abdominal wall with a needle and evacuating the fluid. Samples from fine-needle aspirations, effusions or other bodily fluids can be spun onto slides using conventional centrifugation or Cytospin® (Shandon, Runcom, U.K.) or smeared onto an appropriate slide for staining and/or fixation. Cell blocks can also be prepared from such samples by concentrating the cells contained therein. For example, cells can be concentrated, e.g., by centrifugation. After concentration, the cells can be fixed in a suitable fixing agent, such as formalin or alcohol and then embedded into paraffin or other suitable material as done for tissue in surgical pathology. Concentrated cells can also be processed for ThinPrep® preparation using, for example, a Cytyc Thin Prep processor (Cytyc Corp Boxborough, Mass.).

Yet another technique for detecting β-catenin is Flow Cytometry (FACS). The theory of Flow Cytometry is discussed in Ormerod (ed) *Flow Cytometry: A Practical Approach* (IRL Press, Oxford. 1994); Shapiro, *Practical Flow Cytometry*. 3rd Edition; (Alan R Liss, Inc.). Givan, *Flow Cytometry. First Principles* (Wiley-Liss, New York, 1992.); Robinson (ed.) *Handbook of Flow Cytometry Methods*. (Wiley-Liss, New York, 1993) FACs provides the means of scanning individual cells for the presence of deregulated β-catenin.

Antibodies reactive with a particular protein can also be measured by a variety of immunoassay methods, as discussed herein. For reviews of immunological and immunoassay procedures applicable to the measurement of antibodies by immunoassay techniques, see, e.g., Stites and Terr (eds.) *Basic and Clinical Immunology* (7th ed.) supra; Maggio (ed.) *Enzyme Immunoassay, supra*; and Harlow and Lane *Antibodies, A Laboratory Manual, supra*.

Techniques for determining β-catenin localization in cells using immunoassays are known in the art, for example, see Wakita et al. 2001 *Cancer Res.* 61:854-858; Carayol et al. 2002 *Am J. Respir Cell Mol Biol.* 26:341-347; Lim et al 2002 *Oncology Reports* 9:915-928; and Sakai et al. 2002 Int. *J. Oncology* 21:547-552; all incorporated herein by reference.

Other Conditions and Diseases

Other conditions and disease processes amenable to treatment with the compounds described herein include, e.g., benign prostatic hyperplasia, familial adenomatosis polyposis, neuro-fibromatosis, atherosclerosis, pulmonary fibrosis, fibrosis which occurs with radiation therapy, arthritis, psoriasis, glomerulonephritis, restenosis following angioplasty or vascular surgery, hypertrophic scar formation, inflammatory bowel disease, transplantation rejection, endotoxic shock, and fungal infections; and defective apoptosis-associated conditions, such as cancers (including, but not limited to, those types mentioned herein above), viral infections (including, but not limited to, HIV, human papilloma virus, herpesvirus, poxvirus, Epstein-Barr virus, Sindbis virus and adenovirus), prevention of AIDS development in HIV-infected individuals, autoimmune diseases (including, but not limited to, systemic lupus erythematosus, rheumatoid arthritis, psoriasis, autoimmune mediated glomerulonephritis, inflammatory bowel disease and autoimmune diabetes mellitus), neurodegenerative disorders (including, but not limited to, Alzheimer's disease, amyotrophic lateral sclerosis, retinitis pigmentosa, Parkinson's disease, AIDS-related dementia, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including, but not limited to, chronic anemia and aplastic anemia), degenerative diseases of the musculoskeletal system (including, but not limited to, osteoporosis and arthritis), aspirin-sensitive rhinosinusitis, cystic fibrosis, multiple sclerosis, schizophrenia, kidney diseases, abnormal angiogenesis, and cancer pain.

Compounds that inhibit uncontrolled or abnormal angiogenesis are useful for treatment of neoplasia, including metastasis; ophthalmological conditions such as corneal graft rejection, ocular neovascularization, retinal neovascularization including neovascularization following injury or infection, diabetic retinopathy, retrolental fibroplasia and neovascular glaucoma; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis.

Preparation of Compounds of the Invention

Compounds of the present invention may be synthesized using standard synthetic 5 techniques known to those of skill in the art or using methods known in the art in combination with methods described herein. See, e.g., March, ADVANCED ORGANIC CHEMISTRY 4$^{th}$ Ed., (Wiley 1992); Carey and Sundberg, ADVANCED ORGANIC CHEMISTRY 3$^{rd}$ Ed., Vols. A and B (Plenum 1992), and Green and Wuts, PROTECTIVE GROUPS IN ORGANIC SYNTHESIS 2$^{nd}$ Ed. (Wiley 1991). General methods for the preparation of compound as disclosed herein may be 10 derived from known reactions in the field, and the reactions may be modified by the use of appropriate reagents and conditions, as would be recognized by the skilled person, for the introduction of the various moieties found in the formulae as provided herein.

Selected examples of covalent linkages and precursor functional groups which yield them are given in the Table entitled "Examples of Covalent Linkages and Precursors Thereof." 15 Precursor functional groups are shown as electrophilic groups and nucleophilic groups. The functional group on the organic substance may be attached directly, or attached via any useful spacer or linker as defined below.

Examples of Covalent Linkages and Precursors Thereof

| Covalent Linkage Product | Electrophile | Nucleophile |
| --- | --- | --- |
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |

| Covalent Linkage Product | Electrophile | Nucleophile |
|---|---|---|
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| Hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |
| Amidines | imido esters | amines/anilines |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Phosphite esters | phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |

In general, carbon electrophiles are susceptible to attack by complementary nucleophiles, including carbon nucleophiles, wherein an attacking nucleophile brings an electron pair to the carbon electrophile in order to form a new bond between the nucleophile and the carbon electrophile.

Suitable carbon nucleophiles include, but are not limited to alkyl, alkenyl, aryl and alkynyl Grignard, organolithium, organozinc, alkyl-, alkenyl, aryl- and alkynyl-tin reagents (organostannanes), alkyl-, alkenyl, aryl- and alkynyl-borane reagents (organoboranes and organoboronates); these carbon nucleophiles have the advantage of being kinetically stable in water or polar organic solvents. Other carbon nucleophiles include phosphorus ylids, enol and enolate reagents; these carbon nucleophiles have the advantage of being relatively easy to generate from precursors well known to those skilled in the art of synthetic organic chemistry. Carbon nucleophiles, when used in conjunction with carbon electrophiles, engender new carbon-carbon bonds between the carbon nucleophile and carbon electrophile.

Non-carbon nucleophiles suitable for coupling to carbon electrophiles include but are not limited to primary and secondary amines, thiols, thiolates, and thioethers, alcohols, alkoxides, azides, semicarbazides, and the like. These non-carbon nucleophiles, when used in conjunction with carbon electrophiles, typically generate heteroatom linkages (C—X—C), wherein X is a hetereoatom, e.g., oxygen or nitrogen.

The term "protecting group" refers to chemical moieties that block some or all reactive moieties and prevent such groups from participating in chemical reactions until the protective group is removed. It is preferred that each protective group be removable by a different means. Protective groups that are cleaved under totally disparate reaction conditions fulfill the requirement of differential removal. Protective groups can be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester derivatives as exemplified herein, or they may be blocked with oxidatively-removable protective groups such as 2,4-dimethoxybenzyl, while co-existing amino groups may be blocked with fluoride labile silyl carbamates.

Allyl blocking groups are useful in then presence of acid- and base-protecting groups since the former are stable and can be subsequently removed by metal or pi-acid catalysts. For example, an allyl-blocked carboxylic acid can be deprotected with a Pd$_0$-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

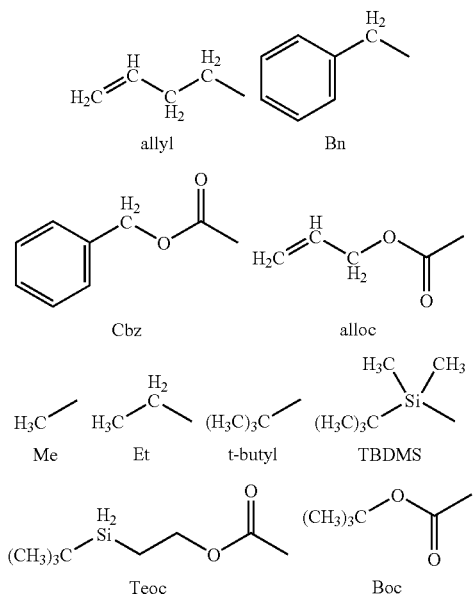

-continued

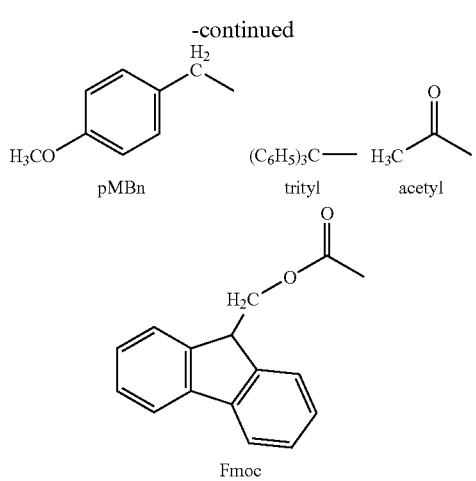

Other protecting groups are described in Greene and Wuts, Protective Groups in Organic Synthesis, 3rd Ed., John Wiley & Sons, New York, N.Y., 1999, which is incorporated herein by reference in its entirety.

In various embodiments, the compounds of the present invention can be prepared according to the following reaction schemes and examples, or modifications thereof. Starting materials can be purchased or made from procedures known in the art or as illustrated. In these reactions, one skilled in the art can make use of variations that are not described in greater detail. Other methods for preparing compounds of the invention will be readily apparent to the person of ordinary skill in the art in light of the following reaction schemes and examples. For example, the synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or generally known in the art will be recognized as having applicability for preparing other compounds of the invention. Unless otherwise indicated, the variables are as defined above.

The abbreviations employed throughout the application have the following meaning unless otherwise indicated: EtOH: ethyl alcohol; $NH_2OH \cdot HCl$: hydroxylamine; $CCl_3CH(OH)_2$: chloral hydrate; $H_2SO_4$: sulfuric acid; $LiBH_4$: lithium borohydride; ClCOCOCl: oxalyl chloride; HCl: Hydrochloric acid; NaOH: sodium hydroxide; $BF_3 \cdot Et_2O$: boron trifluoride etherate; $CH_2Cl_2$: dichloromethane; [R]: partial reduction.

General Scheme 1A shows the preparation of pyranoindol-1-yl alcohols from starting material 1.

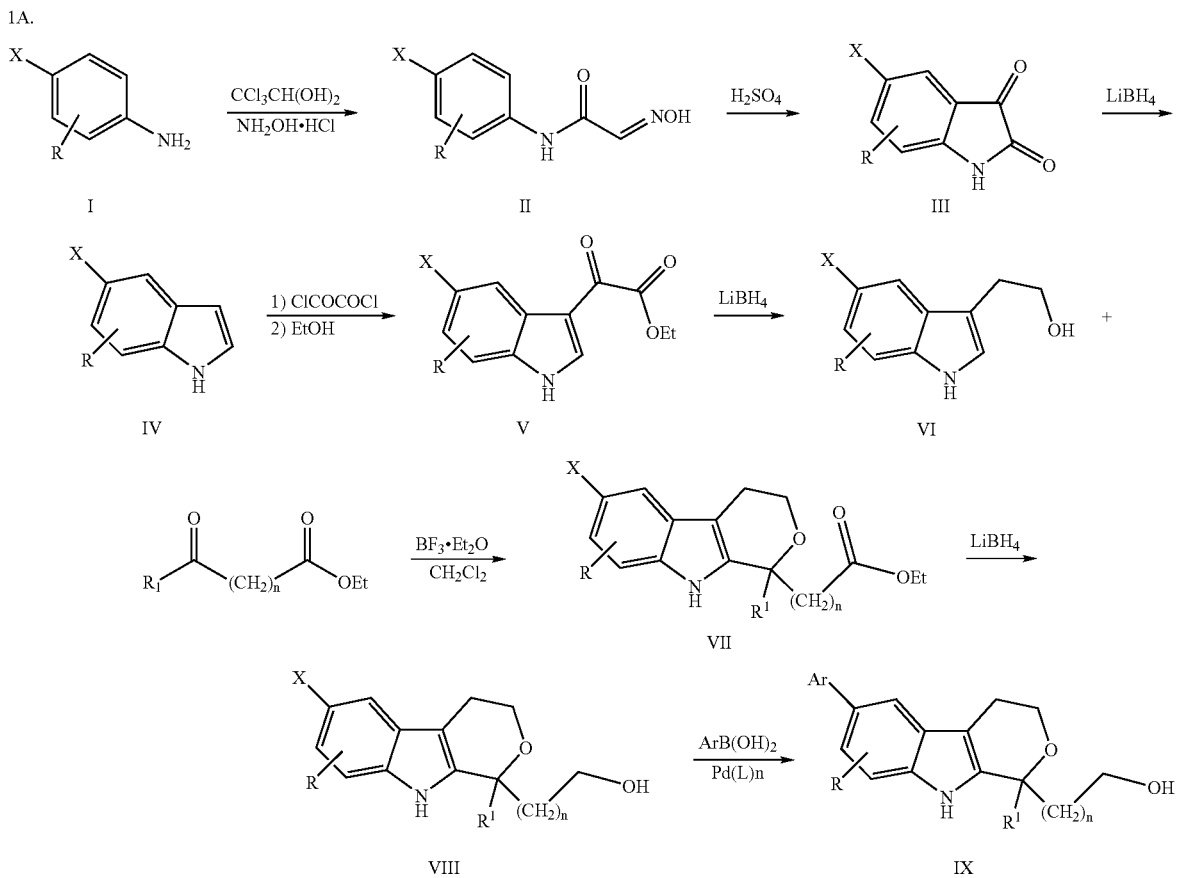

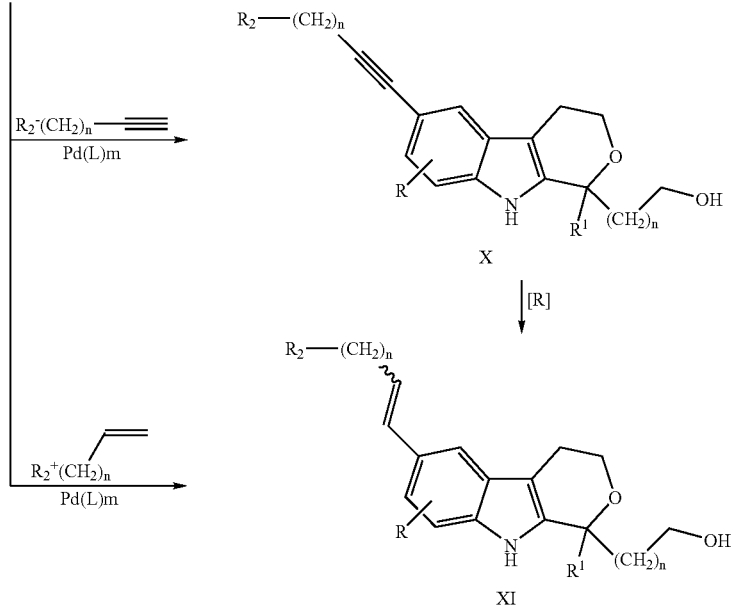

In General Scheme 1, 1,3,4,9-tetrahydro-pyrano[3,4-b] indole of this invention may be prepared by techniques well known to those skilled in the art of organic synthesis. The substituted tryptophols (VI) may be prepared by the appropriate segment of the pathway illustrated in General Scheme 1A, starting with an aniline (I), an isatin (III), or an indole (IV). The suitable starting materials are commercially available anilines with the desired R or may be readily prepared. The aniline may be converted into a corresponding isatin (III) by treatment of aniline with chloral hydrate and hydroxylamine, followed by heating with sulfuric acid. The indole (IV) may be obtained by reduction of isatin with lithium borohydride or other reducing agents. The tryptophol (VI) may be prepared by acylation at 3-position of indole (IV) with a suitable reagent, e.g., oxalyl chloride, followed by reduction of glyoxylate (V) with lithium borohydride. The substituted tryptopholes (VI) may be condensed with an appropriate ketone or aldehyde, in the presence of an acid catalyst, to provide 1,3,4,9-tetradydro-pyrano[3,4-b]indole (VII). After the ester (VII) is reduced by an appropriate reducing reagent, e.g., lithium borohydride, the title compounds (IX) may be prepared from (VIII) by displacement of the halogen with an appropriately activated Ar moiety. For example, in the presence of an appropriate Pd(L)m catalyst, Ar-boronic acids may be coupled via a Suzuki reaction to give the title compounds (IX). Compounds (X) and (XI) may be prepared, via Heck reaction, from suitable alkyne and alkene precursors in the presence of an appropriate Pd(L)m catalyst. The cis isomer of (XI) may also be prepared by partial reduction of (X) by hydrogenation over palladium on activated carbon that has been treated with quinoline.

General Scheme 1B shows the preparation of pyranoindol-1-yl alkylsulfonamides from starting material 6.

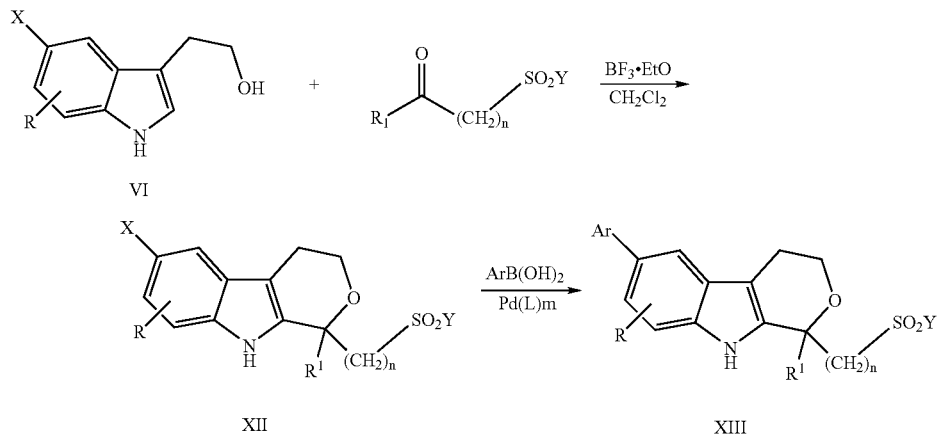

-continued

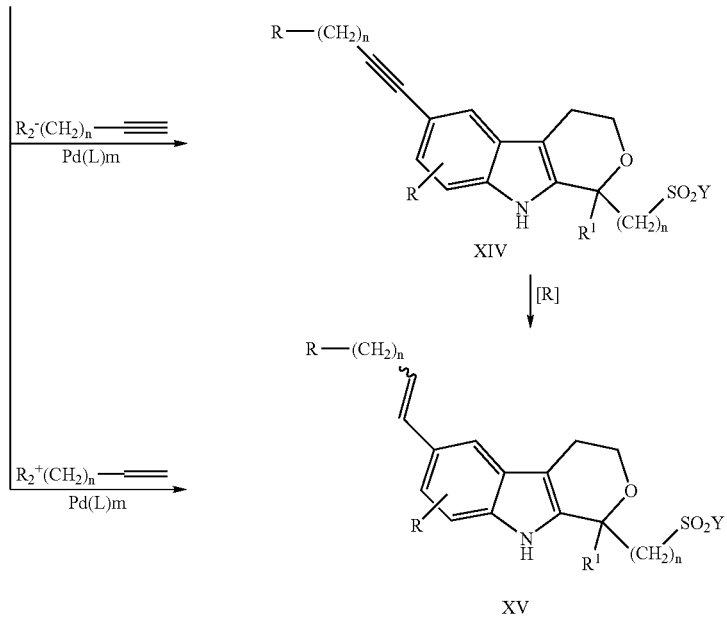

Y=H, OH, NH$_2$, NHR, NRR, R
X=Br, I
R=unsubstituted or substituted alkyl, aryl, alkenyl, or alkynyl
Ar=unsubstituted or substituted aryl
R$_1$=hydrogen, lower alkyl, lower alkenyl, lower alkynyl, lower alkoxy, lower cycloalkyl, phenyl, benzyl and 2-thienyl
n=0 to 6

Scheme 1B illustrates syntheses of the title compounds (XIII), (XIV), or (XV) wherein —(CH$_2$)$_n$SO$_2$Y is substituted at 1-position of 1,3,4,9-tetradydro-pyrano[3,4-b]indole. The compounds (XIII) may be prepared by condensation of tryptophols (VI) with an appropriate ketone or aldehyde bearing —SO$_2$Y in the presence of a suitable acid, followed by coupling reactions, which may be via Suzuki reaction with a suitable activated Ar moiety in the presence of an appropriate Pd(L)m catalyst. Analogously, compounds (XIV) and (XV) may be prepared, via Heck reaction, from suitable alkyne and alkene in the presence of an appropriate Pd(L)m catalyst.

General Scheme 2 illustrates the additional embodiment wherein R$_{10}$ is lower alkyl, lower alkenyl, lower alkynyl, or aryl. The nitrogen of compound (VII) may be alkylated with an appropriate alkyl halide in the presence of a suitable base. After the ester is reduced to the alcohol (XVII) by a suitable reducing reagent, e.g., lithium borohydride, the title compounds (XVIII), (XIX), or (XX) may be prepared by coupling reactions, e.g., Suzuki reaction or Heck reaction.

General Scheme 2

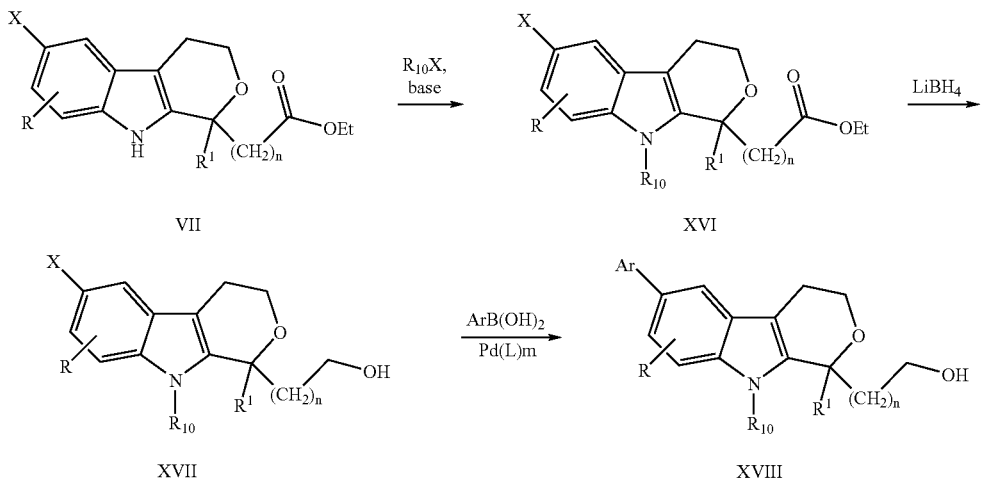

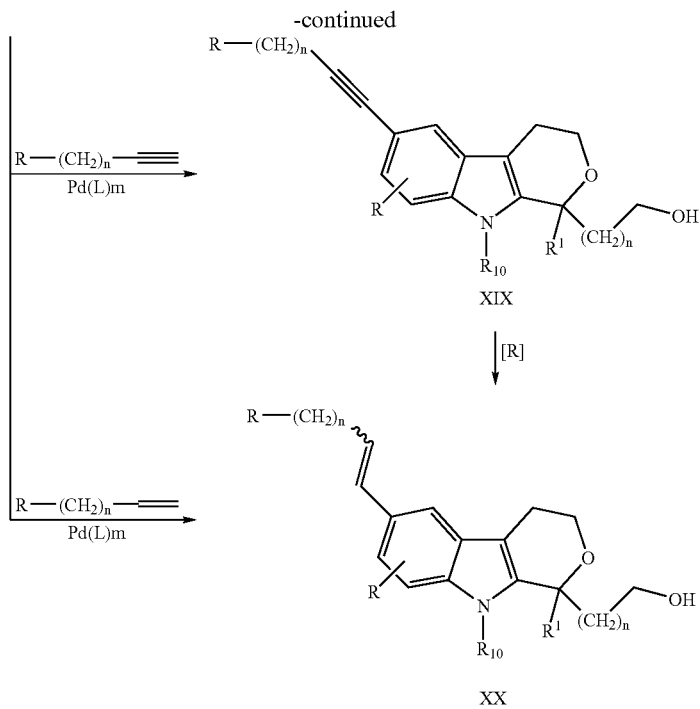
$R_{10}$=lower alkyl, lower alkenyl, lower alkynyl, benzyl, or aryl
X=Br, I
General Scheme 3 illustrates the synthesis of compounds where $R_7$ is substituted, $R_9$ is an isopropyl group, $R_1$ is ethyl, and Y-Z is ethylalcohol.
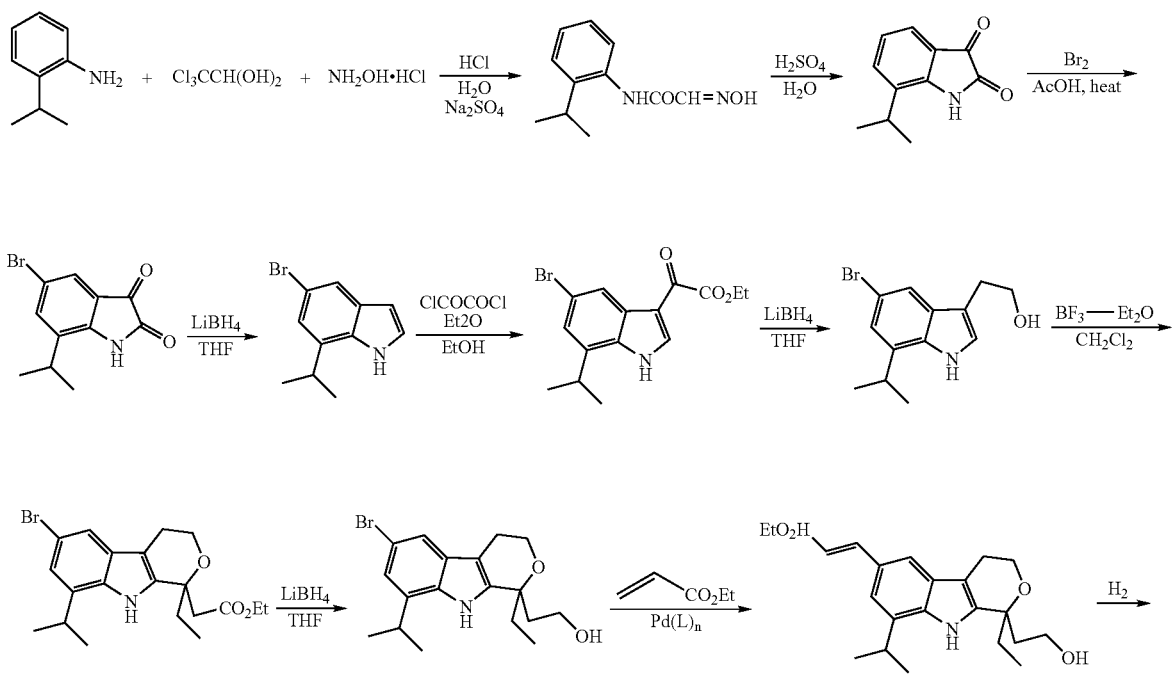

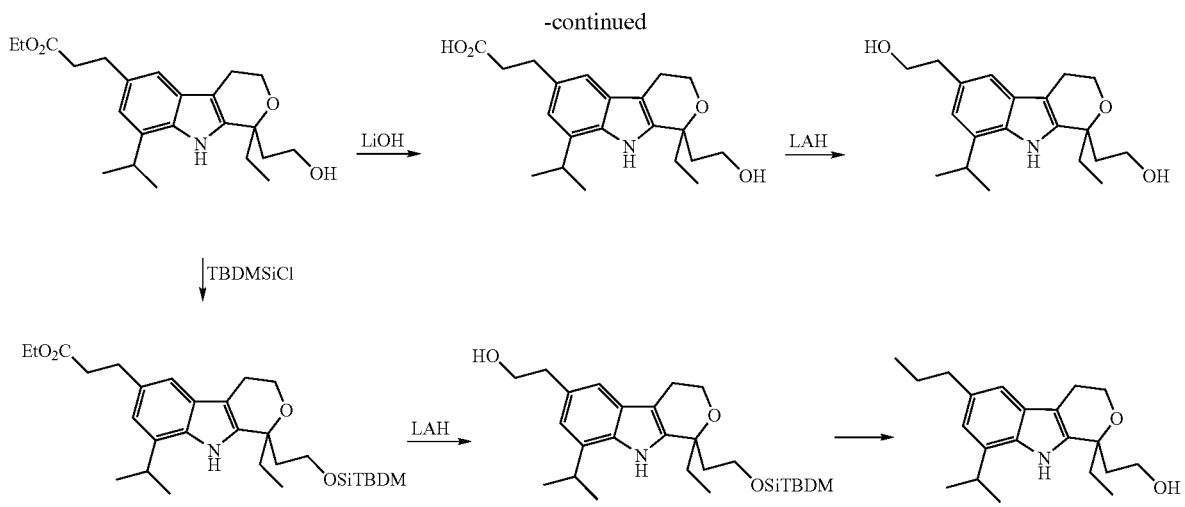

General Scheme 4 illustrates the synthesis of of pyranoindol-1-yl alcohols.

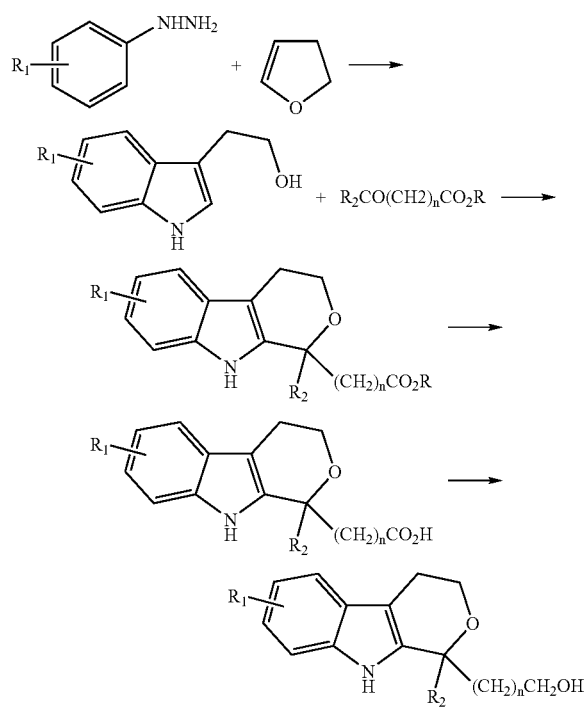

EXAMPLES

Example 1

Synthesis of Compounds

COMPOUND 1: 2-(1,8-DIETHYL-6-PHENYL-1,3,4,9-TETRAHYDRO-PYRANO[3,4-B]INDOL-1-YL)-ETHANOL

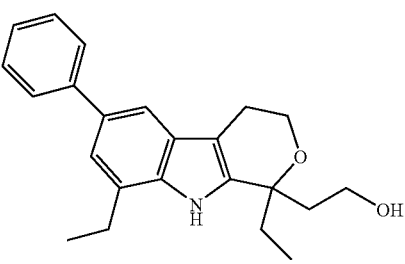

1.A. Synthesis of N-(4-Bromo-2-ethyl-phenyl)-2-hydroximino-acetoamide

To a suspension of 4-bromo-2-ethylaniline (50.0 g, 250 mmol) in water (1000 mL) was added concentrated hydrochloric acid (25 mL), sodium sulfate (220 g), and hydroxylamine hydrochloride (56.25 g), followed by addition of chloral hydrate (44.0 g). The reaction mixture was heated to 90° C. using an oil bath for 1 hour. After cooling down to room temperature, it was extracted with ethyl acetate. Extract was dried over magnesium sulfate and concentrated under reduced pressure to give the title compound (31.1 g, 46% yield). $^1$H NMR (DMSO-$d_6$) δ 12.24 (s, 1H), 9.56 (s, 1H), 7.68 (s, 1H), 7.41 (m, 3H), 2.58 (q, 2H), 1.11 (t, 3H).

1.B. Synthesis of 5-Bromo-7-ethyl-1H-indole-2,3-dione

To a solution of sulfuric acid (100 mL) and water (10 mL) at 80° C. (oil bath) was added N-(4-bromo-2-ethyl-phenyl)-2-hydroximino-acetoamide (61.0 g, 225 mmol) in small portions over 20 minutes. The reaction mixture was heated at 80° C. (oil bath) for 15 minutes. After cooling to room temperature, ice-water (500 mL) was added and the mixture was extracted with ethyl acetate. Extracts were washed with saturated sodium bicarbonate solution, dried over magnesium sulfate, and concentrated under reduced pressure to give the title compound (42.3 g, 74% yield). $^1$H NMR (DMSO-$d_6$) δ 8.87 (s, 1H), 7.75 (d, 1H), 7.71 (d, 1H), 2.75 (q, 2H), 1.44 (t, 3H).

1.C. Synthesis of (5-Bromo-7-ethyl-1H-indol-3-yl)-oxo-acetic acid ethyl ester

To a solution of 5-bromo-7-ethyl-1H-indole-2,3-dione (36.0 g, 144 mmol) in tetrahydrofuran (120 mL) at room temperature was dropped a 2.0 M solution of lithium borohydride in tetrahydrofuran. The reaction mixture was stirred at 90° C. (oil bath) for 5 hours. After cooling down to room temperature, it was quenched with 5% hydrochloric acid solution until the excess lithium borohydride was destroyed. To the mixture was added saturated sodium bicarbonate solution (300 mL) and extracted with ethyl acetate. Extracts were dried over magnesium sulfate and concentrated under reduced pressure to give the crude product of 5-bromo-7-ethyl-1H-indole, which went to next reaction without further purification.

To a solution of 5-bromo-7-ethyl-1H-indole in ethyl ether (400 mL) at room temperature under nitrogen was added a 2.0 M solution of oxalyl chloride in dichloromethane. After the reaction mixture was stirred at room temperature for 6 hours, the solvents were removed under reduce pressure. To the residue was added ethyl alcohol (400 mL) and stirred at room temperature overnight. After ethyl alcohol was removed under reduce pressure, to the residue was added saturated sodium bicarbonate solution (300 mL) and extracted with ethyl acetate. Extract was dried over magnesium sulfate and concentrated under reduced pressure. The crude product was purified-by column chromatography (silica gel, 30-50% ethyl acetate/hexane) to give the title compound (14.5 g, 31% yield). ES-MS (m/z) 324 [M+1]$^+$, 322 [M−1]$^-$.

1.D. Synthesis of (6-Bromo-1,8-diethyl-1,3,4,9-tetrahydro-pyrano[3,4-b]indol-1-yl)-acetic acid ethyl ester To a solution of (5-bromo-7-ethyl-1H-indol-3-yl)-oxo-acetic acid ethyl ester (1.55 g, 4.8 mmol) in tetrahydrofuran at room temperature under nitrogen was dropped a 2.0 M solution of lithium borohydride in tetrahydrofuran. The reaction mixture was heated at 90° C. oil bath for 5 hours. After cooling to room temperature, it was quenched with 5% hydrochloric acid solution until the excess lithium borohydride was destroyed. To the mixture was added saturated sodium bicarbonate solution and extracted with ethyl acetate. Extracts were dried over magnesium sulfate and concentrated under reduced pressure to give the crude product of 2-(5-bromo-7-ethyl-1H-indol-3-yl)-ethanol, which went to the next reaction without further purification.

To a solution of 2-(5-bromo-7-ethyl-1H-indol-3-yl)-ethanol in dichloromethane at room temperature under nitrogen was added boron trifluoride diethyl etherate (0.809 g, 5.7 mmol), followed by ethyl propionylacetate (1.038 g, 7.2 mmol). The reaction mixture was stirred at room temperature for 5 hours. It was quenched with saturated sodium bicarbonate solution and extracted with dichloromethane. The extract was dried over magnesium sulfate and concentrated under reduced pressure. The crude product was purified by column chromatography (silica gel, 15-20% ethyl acetate/hexane) to give the title compound (0.994 g, 53% yield). ES-MS (m/z) 394 [M+1]$^+$, 392 [M−1]$^-$.

1.E. Synthesis of 2-(6-Bromo-1,8-diethyl-1,3,4,9-tetrahydro-pyrano[3,4-b]indol-1-yl)-ethanol To a solution of (6-bromo-1,8-diethyl-1,3,4,9-tetrahydropyrano[3,4-b]indol-1-yl)-acetic acid ethyl ester (5.2 g, 13.2 mmol) in tetrahydrofuran at room temperature under nitrogen was dropped a 2.0 M solution of lithium borohydride in tetrahydrofuran. The reaction mixture was heated at 90° C. (oil bath) for 5 hours. After cooling to room temperature, it was quenched with 5% hydrochloric acid solution until the excess lithium borohydride was destroyed. Water was added and the mixture extracted with ethyl acetate. Extracts were dried over magnesium sulfate and concentrated under reduced pressure. The crude product was purified by column chromatography (silica gel, 50% ethyl acetate/hexane) to give the title compound (3.80 g, 82% yield). 1H NMR (CDCl3) δ8.07 (s, 1H), 7.64 (d, 1H), 7.26 (d, 1H), 4.17 (m, 2H), 3.86 (m, 2H), 2.94 (m, 3H), 2.87 (dt, 1H), 2.76 (t, br, 1H), 2.36 (m, 1H), 2.24 (m, 1H), 2.13 (m, 2H), 1.49 (t, 3H), 1.08 (t, 3H). ES-MS (m/z) 352 [M+1]$^+$, 350 [M−1]$^-$.

1.F. Synthesis of 2-(1,8-Diethyl-6-phenyl-1,3,4,9-tetrahydro-pyrano[3,4-b]indol-1-yl)-ethanol To a solution of 2-(6-bromo-1,8-diethyl-1,3,4,9-tetrahydro-pyrano[3,4-b]indol-1-yl)-ethanol (3.8 g, 10.8 mmol) in ethylene glycol dimethyl ether (50 mL) was added potassium phosphate (6.37 g, 30 mmol), phenylboronic acid (1.83 g, 15 mmol), and [1,1'-bis(diphenylphosphino)ferrocene]dichloropalladium (II) complex with dichloromethane. The reaction mixture was heated at 90° C. (oil bath) overnight. It was quenched with water and extracted with ethyl acetate. Extracts were dried over magnesium sulfate and concentrated under reduced pressure. The crude product was purified by column chromatography (silica gel, 50% ethyl acetate/hexane, followed by Sephadex LH-20, 50% chloroform/hexane) to give the title compound (0.75 g, 20% yield). $^1$H NMR (CDCl$_3$) δ 7.77 (s, 1H), 7.66 (d, 1H), 7.63 (m, 1H), 7.56 (d, 1H), 7.44 (m, 3H), 7.32 (m, 1H), 4.06 (m, 2H), 3.72 (m, 3H), 2.91 (m, 3H), 2.81 (dt, 1H), 2.65 (dd, 1H), 2.20 (m, 1H), 2.07 (m, 2H), 1.40 (t, 3H), 0.95 (t, 3H). ES-MS (m/z) 348 [M−1]$^-$.

COMPOUND 2: 2-[1,8-DIETHYL-6-(4-METHOXY-PHENYL)-1,3,4,9-TETRAHYDRO-PYRANO[3,4-B]INDOL-1-YL]-ETHANOL

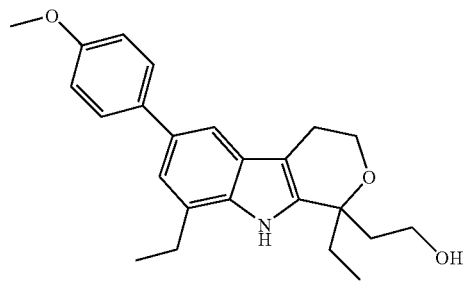

The title compound is prepared in a-manner analogous to Example 1, except using 4-methoxyphenylboronic acid in step 1.F.

COMPOUND 3: 2-[1,8-DIETHYL-6-(3-TRIFLUOROMETHOXY-PHENYL)-1,3,4,9-TETRAHYDRO-PYRANO[3,4-B]INDOL-1-YL]-ETHANOL

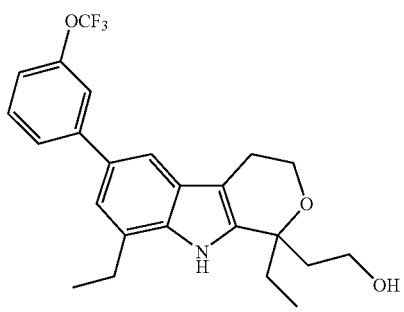

The title compound is prepared in a manner analogous to Example 1, except using 3-trifluoromethoxyphenylboronic acid in step 1.F.

COMPOUND 4: 2-[1,8-DIETHYL-6-(2-TRIFLUOROM-ETHYL-PHENYL)-1,3,4,9-TETRAHYDRO-PYRANO[3,4-B]INDOL-1-YL]-ETHANOL

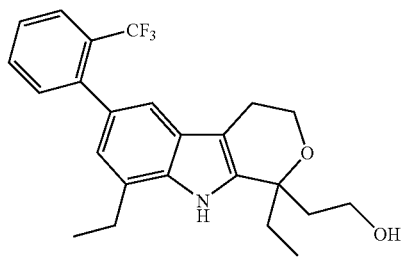

The title compound is prepared as described in Example 1, except using 2-trifluoromethylphenylboronic acid in step 1.F.

COMPOUND 5: 2-[6-(2,4-DIFLUORO-PHENYL)-1,8-DIETHYL-1,3,4,9-TETRAHYDRO-PYRANO[3,4-B]INDOL-1-YL]-ETHANL

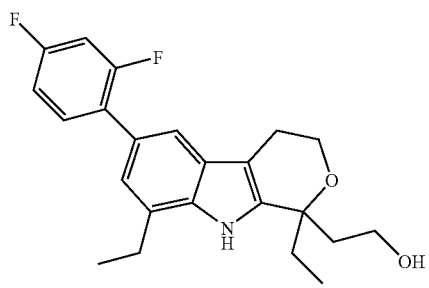

The title compound is prepared in a manner analogous to Example 1, except using 2,4-difluorophenylboronic acid in step 1.F.

COMPOUND 6: 2-(1,8-DIETHYL-6-PYRIDIN-4-YL-1,3,4,9-TETRAHYDRO-PYRANO[3,4-B]INDOL-1-YL)-ETHANOL

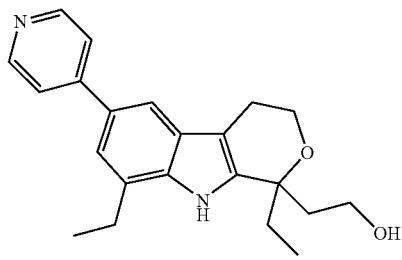

The title compound is prepared in a manner analogous to Example 1, except using pyridine-4-boronic acid in step 1.F.

COMPOUND 8: 2-[6-(3-AMINO-PHENYL)-1,8-DIETHYL-1,3,4,9-TEAHYDRO-PYRANO[3,4-B]INDOL-1-YL]-ETHANOL

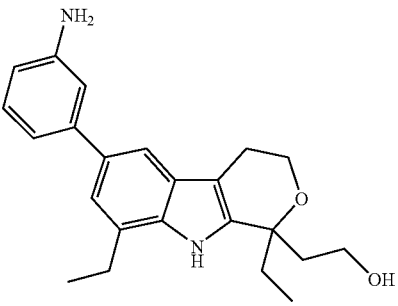

The title compound is prepared in a manner analogous to Example 1, except using 3-aminophenylboronic acid in step 1.F.

COMPOUND 10: 2-[6-(3,4-DIFLUORO-PHENYL)-1,8-DIETHYL-1,3,4,9-TETRAHYDRO-PYRANO[3,4-B]INDOL-1-YL]-ETHANOL

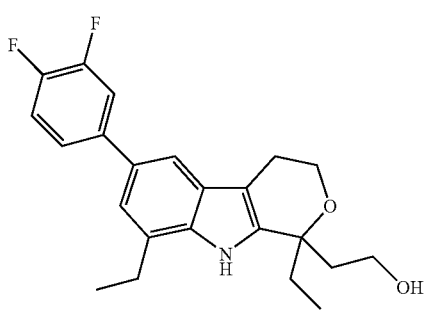

The title compound is prepared in a manner analogous to Example 1, except using 3,4-difluorophenylboronic acid in step 1.F.

COMPOUND 11: 2-[6-(5-CHLORO-THIOPHEN-2-YL)-1,8-DIETHYL-1,3,4,9-TETRAHYDRO-PYRANO[3,4-B]INDOL-1-YL]-ETHANOL

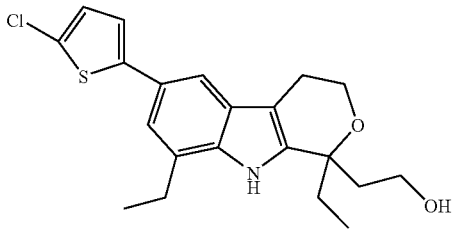

The title compound is prepared in a manner analogous to Example 1, except using 5-chloro-2-thiopheneboronic acid in step 1.F.

COMPOUND 12: 2-(1-ETHYL-6-ISOPROPYL-8-PHENYL-1,3,4,9-TETRAHYDRO-PYRANO[3,4-B]INDOL-1-YL)-ETHANOL

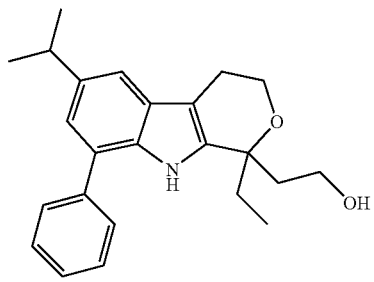

12.A. Synthesis of N-(2-Bromo-4-isopropyl-phenyl)-2-hydroximino-acetoamide

The title compound is prepared in a manner analogous to Example 1, except using 2-bromo 4-aminoaniline in step 1.A.

12.B. Synthesis of 7-Bromo-5-isopropyl-1H-indole-2,3-dione

The title compound is prepared in a manner analogous to Example 1, except using N-(2-bromo-4-isopropyl-phenyl)-2-hydroximino-acetoamide in step 1.B.

12.C. Synthesis of (7-Bromo-5-isopropyl-1H-indol-3-yl)-oxo-acetic acid ethyl ester The title compound is prepared in a manner analogous to Example 1, except using 7-bromo-5-isopropyl-1H-indole-2,3-dione in step 1.C.

12.D. Synthesis of (8-Bromo-1-ethyl-6-isopropyl-1,3,4,9-tetrahydro-pyrano[3,4-b]indol-1-yl)-acetic acid ethyl ester The title compound is prepared in a manner analogous to Example 1, except using (7-bromo-5-isopropyl-1H-indol-3-yl)-oxo-acetic acid ethyl ester in step 1.D.

12.E. Synthesis of 2-(8-Bromo-1-ethyl-6-isopropyl-1,3,4,9-tetrahydro-pyrano[3,4-b]indol-1-yl)-ethanol The title compound is prepared in a manner analogous to Example 1, except using (8-bromo-1-ethyl-6-isopropyl-1,3,4,9-tetrahydro-pyrano[3,4-b]indol-1-yl)-acetic acid ethyl ester in step 1.E.

12.F Synthesis of 2-(1-Ethyl-6-isopropyl-8-phenyl-1,3,4,9-tetrahydro-pyrano[3,4-b]indol-1-yl)-ethanol The title compound is prepared in a manner analogous to Example 1, except using 2-(8-bromo-1-ethyl-6-isopropyl-1,3,4,9-tetrahydro-pyrano[3,4-b]indol-1-yl)-ethanol in step 1.F.

COMPOUND 13: 2-[8-(3-CYANO-PHENYL)-1-ETHYL-6-ISOPROPYL-1,3,4,9-TETRAHYDRO-PYRANO[3,4-B]INDOL-1-YL]-ETHANOL

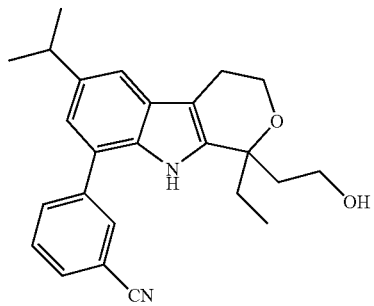

The title compound is prepared in a manner analogous to Example 1, except using 2-(8-bromo-1-ethyl-6-isopropyl-1,3,4,9-tetrahydro-pyrano[3,4-b]indol-1-yl)-ethanol and 3-cyanophenylboronic acid in step 1.F.

COMPOUND 14: 2-[8-(5-BROMO-2-METHOXY-PHENYL)-1-ETHYL-6-ISOPROPYL-1,3,4,9-TETRAHYDRO-PYRANO[3,4-B]INDOL-1-YL]-ETHANOL

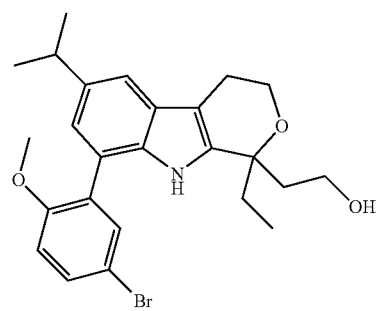

The title compound is prepared in a manner analogous to Example 1, except using 2-(8-bromo-1-ethyl-6-isopropyl-1,3,4,9-tetrahydro-pyrano[3,4-b]indol-1-yl)-ethanol and 2-bromo-3-methoxyphenylboronic acid in step 1.F.

COMPOUND 15: 2-[1-ETHYL-8-(2-FLUORO-BIPHENYL-4-YL)-6-ISOPROPYL-1,3,4,9-TETRAHYDRO-PYRANO[3,4-B]INDOL-1-YL]-ETHANOL

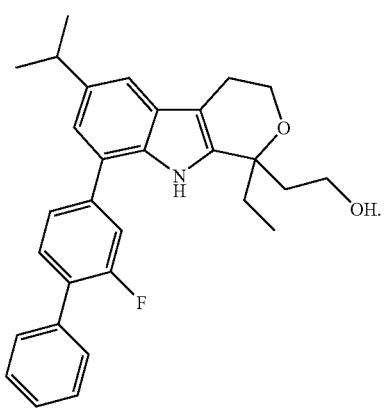

The title compound is prepared in a manner analogous to Example 1, except using 2-(8-bromo-1-ethyl-6-isopropyl-1,3,4,9-tetrahydro-pyrano[3,4-b]indol-1-yl)-ethanol and 2-fluorobiphenyl-4-boronic acid in step 1.F.

COMPOUND 16: 4-[1-ETHYL-1-(2-HYDROXY-ETHYL)-6-ISOPROPYL-1,3,4,9-TETRAHYDRO-PYRANO[3,4-B]INDOL-8-YL]-BENZOIC ACID

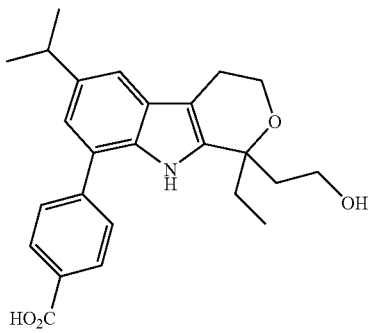

The title compound is prepared in a manner analogous to Example 1, except using 2-(8-bromo-1-ethyl-6-isopropyl-1,3,4,9-tetrahydro-pyrano[3,4-b]indol-1-yl)-ethanol and 4-carboxylphenylboronic acid in step 1 F.

COMPOUND 17: 3-[1-ETHYL-1-(2-HYDROXY-ETHYL)-6-ISOPROPYL-1,3,4,9-TETRAHYDRO-PYRANO[3,4-B]INDOL-8-YL]-BENZALDEHYDE

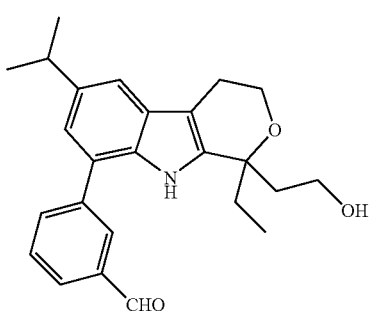

The title compound is prepared in a manner analogous to Example 1, except using 2-(8-bromo-1-ethyl-6-isopropyl-1,3,4,9-tetrahydro-pyrano[3,4-b]indol-1-yl)-ethanol and 3-formylphenylboronic acid in step 1.F.

COMPOUND 18: 2-[8-(3,5-DIMETHYL-PHENYL)-1-ETHYL-6-ISOPROPYL-1,3,4,9-TETRAHYDRO-PYRANO[3,4-B]INDOL-1-YL]-ETHANOL

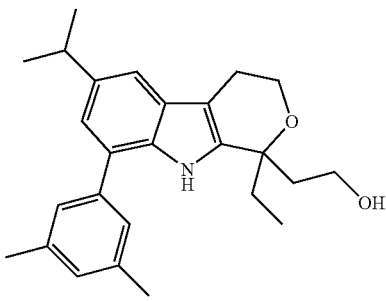

The title compound is prepared in a manner analogous to Example 1, except using 2-(8-bromo-1-ethyl-6-isopropyl-1,3,4,9-tetrahydro-pyrano[3,4-b]indol-1-yl)-ethanol and 3,5-dimethylphenylboronic acid in step 1.F.

COMPOUND 19: 2-(8-DIBENZOFURAN-3-YL-1-ETHYL-6-ISOPROPYL-1,3,4,9-TETRAHYDRO-PYRANO[3,4-B]INDOL-1-YL)-ETHANOL

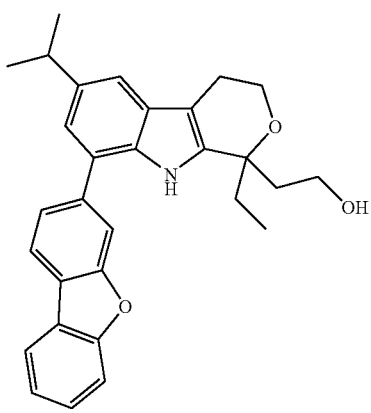

The title compound is prepared in a manner analogous to Example 1, except using 2-(8-bromo-1-ethyl-6-isopropyl-1,3,4,9-tetrahydro-pyrano[3,4-b]indol-1-yl)-ethanol and 4-dibenzofuranboronic acid in step 1.F.

COMPOUND 20: 2-(1-ETHYL-6-ISOPROPYL-8-STYRYL-1,3,4,9-TETRAHYDRO-PYRANO[3,4-B]IN-DOL-1-YL)-ETHANOL

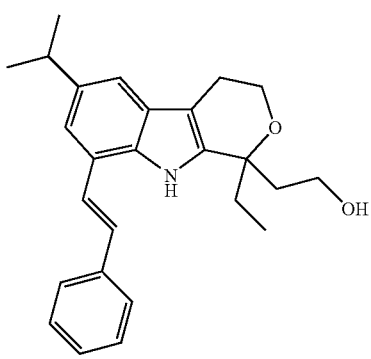

20.A. Synthesis of 2-(1-Ethyl-6-isopropyl-8-styryl-1,3,4,9-tetrahydro-pyrano[3,4-b]indol-1-yl)-ethanol The title compound is prepared according to the following procedure. To solution of 2-(8-bromo-1-ethyl-6-isopropyl-1,3,4,9-tetrahydro-pyrano[3,4-b]indol-1-yl)-ethanol (1.0 mmol) dried acetonitril (10 mL) at under nitrogen is added triethylamine (1.5 mL), tri-o-tolylphosphine (0.4 mmol), styrene (2.0 mmol), and tri(debenzylideneacetone)dipalladiumn (0) (0.1 mmol). The reaction mixture is heated at 90° C. (oil bath) overnight. It is quenched with water and extracted with ethyl acetate. Extracts are dried over magnesium sulfate and concentrated under reduced pressure. The chromatography (silica gel) gives the title-compound.

COMPOUND 21: 2-(1-ETHYL-6-ISOPROPYL-8-PHE-NYLETHYNYL-1,3,4,9-TETRAHYDRO-PYRANO[3,4-B]INDOL-1-YL)-ETHANOL

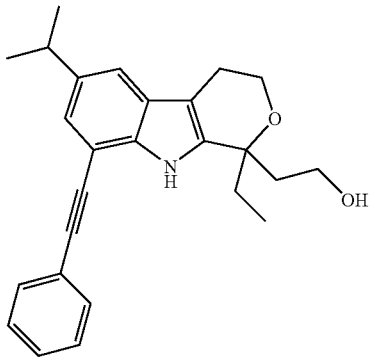

The title compound is prepared in a manner analogous to Example 20.A, except using phenylacetylene.

COMPOUND 22: (1-ETHYL-1,3,4,9-TETRAHYDRO-PYRANO[3,4-B]INDOL-1-YL)-ETHANOL

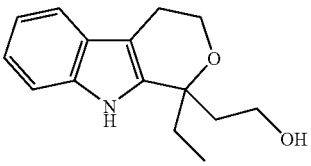

The title compound is prepared in a manner analogous to the procedure outlined below:

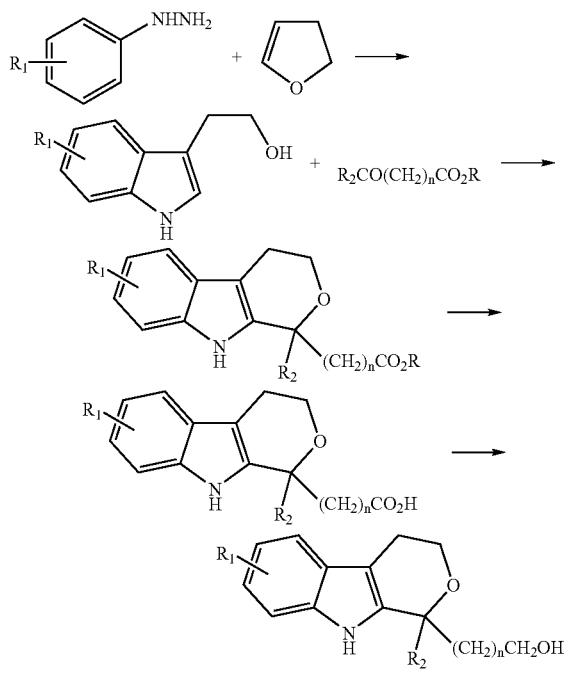

22.A. Synthesis of (1-Ethyl-1,3,4,9-tetrahydro-pyrano[3,4-b]indol-1-yl)-acetic acid ethyl ester A mixture of tryptophol (1.612 g, 10 mmol), ethyl propionylacetate (1.730 g, 12 mmol), and p-toluenesulfonic acid monohydrate (0.20 g) in benzene (70 mL) was heated to reflux for 5 hours. It was quenched with ethyl acetate and washed with saturated sodium bicarbonate. The organic layer was dried over magnesium sulfate, evaporated to dryness. Flash chromatography on silica gel provided 1.943 g (68%) of the title compound as a solid. mp<80° C. $^1$H NMR (300 MHz, CDCl$_3$) δ 9.06 (br, 1H), 7.50 (d, 1H), 7.36 (d, 1H), 7.14 (t, 1H), 7.12 (t, 1H), 4.18 (q, 2H), 4.03 (m, 1H), 3.94 (m, 1H), 2.99 (d, 1H), 2.88 (d, 1H), 2.78 (m, 2H), 2.14 (m, 1H), 2.01 (m, 1H), 1.25 (t, 3H), 0.82 (t, 3H); ESI (+) MS m/e=288 (MH$^+$), ESI (−) MS m/e=286 (MH$^−$).

22.B. Synthesis of (1-Ethyl-1,3,4,9-tetrahydro-pyrano[3,4-b]indol-1-yl)-acetic acid To a solution of (1-ethyl-1,3,4,9-tetrahydro-pyrano[3,4-b]indol-1-yl)-acetic acid ethyl ester (2.50 g, 8.7 mmol) in 1,4-dioxane was added a solution of lithium hydroxide monohydrate (1.50 g, 35.7 mmol) in water (5 mL). The mixture was stirred at room temperature overnight. It was neutralized with 5% HCl solution and extracted with ethyl acetate. The extracts were washed with brine, dried over magnesium sulfate, and evaporated to dryness. Flash chromatography on silica gel provided 0.954 g (42%) of the title compound as a solid. mp. 135-136° C. $^1$H NMR (500 MHz, CDCl$_3$) δ 10.0 (br, 1H), 8.55 (br, 1H), 7.51 (d, 1H), 7.34 (d, 1H), 7.18 (t, 1H), 7.12 (t, 1H), 4.12 (m, 1H), 4.06 (m, 1H), 3.01 (d, 1H), 2.99 (d, 1H), 2.85 (m, 2H), 2.10 (m, 1H), 2.03 (m, 1H), 0.86 (t, 3H); ESI (+) MS m/e=260 (MH$^+$), ESI (−) MS m/e=258 (MH$^−$).

22. C. Synthesis of (1-Ethyl-1,3,4,9-tetrahydro-pyrano[3,4-b]indol-1-yl)-ethanol To solution of (1-ethyl-1,3,4,9-tetrahydro-pyrano[3,4-b] indol-1-yl)-acetic acid (0.52 g, 2.0 mmol) in tetrahydrofuran (10 mL) was added lithium aluminum hydride (0.114 g, 3.0 mmol) in several small portions. The mixture was stirred at room temperature for 6 hours. It was quenched with ethyl acetate carefully and washed with water. The organic layer was dried over magnesium sulfate and evaporated to dryness. Flash chromatography on silica gel provided 0.389 g (79%) of the title compound as an oil. $^1$H NMR (500 MHz, CDCl$_3$) δ 7.82 (br, 1H), 7.52 (d, 1H), 7.34 (d, 1H), 7.18 (td, 1H), 7.13 (td, 1H), 4.07 (m, 1H), 4.01 (m, 1H), 3.70 (m, 1H), 3.64 (m, 1H), 2.89 (m, 1H), 2.77 (dt, 1H), 2.71 (br, 1H), 2.20 (m, 1H), 2.05 (m, 1H), 2.00 (m, 1H), 1.90 (m, 1H), 0.94 (t, 3H); ESI (+) MS m/e=246 (MH$^+$), ESI (−) MS m/e=244 (MH$^−$).

COMPOUND 23: 2-(1-ETHYL-6-METHOXY-1,3,4,9-TETRAHYDRO-PYRANO[3,4-B]INDOL-1-YL)-ETHANOL

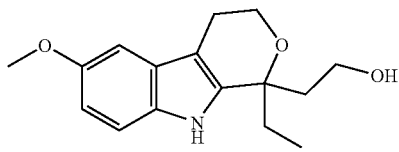

23.A. Synthesis of (1-Ethyl-6-methoxy-1,3,4,9-tetrahydro-pyrano[3,4-b]indol-1-yl)-acetic acid ethyl ester The title compound was synthesized in a manner analogous to step 22, using 5-methoxytryptophol as the 3-indolethanol component in step 22.A. $^1$H NMR (300 MHz, CDCl$_3$) δ 8.93 (br, 1H), 7.25 (d, 1H), 6.95 (d, 1H), 6.90 (dd, 1H), 4.17 (q, 2H), 4.03 (m, 1H), 3.94 (m, 1H), 3.86 (s, 3H), 2.99 (d, 1H), 2.90 (d, 1H), 2.74 (m, 2H), 2.12 (m, 1H), 2.00 (m, 1H), 1.27 (t, 3H), 0.82 (t, 3H); ESI (+) MS m/e=318 (MH⁺), ESI (−) MS m/e=316 (MH⁻).

23.B. Synthesis of (1-Ethyl-6-methoxy-1,3,4,9-tetrahydro-pyrano[3,4-b]indol-1-yl)-acetic acid The title compound was synthesized in a manner analogous to step 22, using (1-ethyl-6-methoxy-1,3,4,9-tetrahydro-pyrano[3,4-b]indol-1-yl)-acetic acid ethyl ester as the ester component in step 22.B., afforded the title compound as a solid. mp. 169° C. ¹H NMR (300 MHz, CDCl₃) δ 8.38 (br, 1H), 7.22 (d, 1H), 6.94 (d, 1H), 6.84 (dd, 1H), 4.08 (m, 2H), 3.85 (s, 3H), 2.97 (m, 2H), 2.81 (m, 2H), 2.02 (m, 2H), 0.85 (t, 3H); ESI (+) MS m/e=290 (MH⁺), ESI (−) MS m/e=288 (MH⁻).

23. C. Synthesis of 2-(1-Ethyl-6-methoxy-1,3,4,9-tetrahydro-pyrano[3,4-b]indol-1-yl)-ethanol The title compound was synthesized in a manner analogous to step 22, using (1-ethyl-6-methoxy-1,3,4,9-tetrahydro-pyrano[3,4-b]indol-1-yl)-acetic acid as the carboxylic acid component in step 22.C., afforded the title compound as a solid. ¹H NMR (500 MHz, CDCl₃) δ 7.71 (br, 1H), 7.22 (d, 1H), 6.97 (d, 1H), 6.83 (dd, 1H), 4.08 (m, 1H), 4.00 (m, 1H), 3.86 (s, 3H), 3.69 (m, 1H), 3.64 (m, 1H), 2.85 (m, 1H), 2.73 (dt, 1H), 2.19 (m, 1H), 2.05 (br, 1H), 2.03 (m, 1H), 1.98 (m, 1H), 1.89 (m, 1H), 0.93 (t, 3H); ESI (+) MS m/e=276 (MH⁺), ESI (−) MS m/e=274 (MH⁻).

COMPOUND 24: 2-(1-ETHYL-6-METHYL-1,3,4,9-TETRAHYDRO-PYRANO[3,4-B]INDOL-1-YL)-ETHANOL

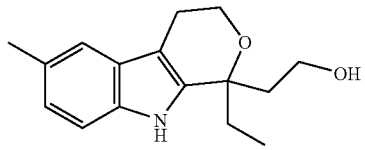

24.A. Synthesis of 2-(5-Methyl-1H-indol-3-yl)-ethanol

To a suspension of 4-methylphenylhydrazine hydrochloride (2.50 g, 15.7 mmol) in 1,4-dioxane (25 mL) and water (1.5 mL) was dropped neat 2,3-dihydrofuran (1.66 g, 23.6 mmol). After the addition, the mixture was heated at 95° C. for 4 hours. After cooling to room temperature, it was poured into ethyl ether, dried over magnesium sulfate, evaporated to dryness. Flash chromatography on silica gel provided 0.485 g (18%) of the title compound as a solid. ¹H NMR (500 MHz, CDCl₃) δ 7.95 (br, 1H), 7.41 (s, 1H), 7.27 (d, 1H), 7.05 (m, 2H), 3.90 (dd, 2H), 3.01 (t, 2H), 2.46 (s, 3H), 1.50 (t, br, 1H).

24.B. Synthesis of (1-Ethyl-6-methyl-1,3,4,9-tetrahydro-pyrano[3,4-b]indol-1-yl)-acetic acid ethyl ester To a solution of 2-(5-methyl-1H-indol-3-yl)-ethanol (0.48 g, 2.7 mmol) in dichloromethane (10 mL) was added boron trifluoride diethyl etherate (0.468 g, 3.3 mmol), followed by ethyl propionylacetate (0.649 g, 4.5 mmol). The mixture was stirred at room temperature for 5 hours. It was quenched with saturated sodium bicarbonate solution and extracted with dichloromethane. The organic layer was dried over magnesium sulfate and evaporated to dryness. Flash chromatography on silica gel provided 0.421 g (52%) of the title compound as an oil. ¹H NMR (500 MHz, CDCl₃) δ 8.90 (br, 1H), 7.28 (s, 1H), 7.24 (d, 1H), 6.99 (d, 1H), 4.16 (m, 2H), 4.03 (m, 1H), 3.94 (m, 1H), 2.98 (d, 1H), 2.88 (d, 1H), 2.80 (m, 1H), 2.73 (m, 1H), 2.44 (s, 3H), 2.12 (m, 1H), 1.98 (m, 1H), 1.25 (t, 3H), 0.80 (t, 3H); ESI (−) MS m/e=300 (MH⁻).

24. C. Synthesis of (1-Ethyl-6-methyl-1,3,4,9-tetrahydro-pyrano[3,4-b]indol-1-yl)-acetic acid The title compound was synthesized in a manner analogous to step 22.B., using (1-ethyl-6-methyl-1,3,4,9-tetrahydro-pyrano[3,4-b]indol-1-yl)-acetic acid ethyl ester as the ester component afforded the title compound as a solid. mp. 158-159 ° C. ¹H NMR (500 MHz, CDCl₃) δ 9.70 (br, 1H), 8.33 (br, 1H), 7.29 (s, 1H), 7.22 (d, 1H), 7.00 (d, 1H), 4.10 (m, 1H), 4.05 (m, 1H), 2.99 (d, 1H), 2.98 (d, 1H), 2.81 (q, 2H), 2.44 (s, 3H), 2.07 (m, 1H), 2.01 (m, 1H), 0.85 (t, 3H); ESI (+) MS m/e=274 (MH⁺), ESI (−) MS m/e=272 (MH⁻).

24.D. Synthesis of 2-(1-Ethyl-6-methyl-1,3,4,9-tetrahydro-pyrano[3,4-b]indol-1-yl)-ethanol The title compound was synthesized in a manner analogous to step 22.C., using (1-ethyl-6-methyl-1,3,4,9-tetrahydro-pyrano[3,4-b]indol-1-yl)-acetic acid as the carboxylic acid component afforded the title compound as a solid. mp. 114-115° C. ¹H NMR (500 MHz, CDCl₃) δ 7.70 (br, 1H), 7.30 (s, 1H), 7.21 (d, 1H), 7.00 (dd, 1H), 4.06 (m, 1H), 3.97 (m, 1H), 3.67 (m, 1H), 3.62 (m, 1H), 2.84 (m, 1H), 2.73 (m, 1H), 2.71 (br, 1H), 2.45 (s, 3H), 2.17 (m, 1H), 2.04 (m, 1H), 1.96 (m, 1H), 1.86 (m, 1H), 0.92 (t, 3H); ESI (+) MS m/e=260 (MH⁺), ES (−) MS m/e=258 (MH⁻).

COMPOUND 25: 2-(1-ETHYL-8-METHYL-1,3,4,9-TETRAHYDRO-PYRANO[3,4-B]INDOL-1-YL)-ETHANOL

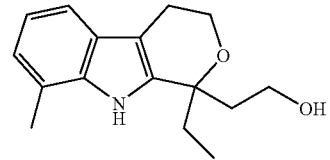

25.A. Synthesis of 2-(7-Methyl-1H-indol-3-yl)-ethanol

Following the procedure of example 24.A. except using 2-methylphenylhydrazine hydrochloride as the hydrazine component afforded the title compound as a solid. ¹H NMR (500 MHz, CDCl₃) δ 7.97 (br, 1H), 7.49 (d, 1H), 7.11 (d, 1H), 7.07 (t, 1H), 7.03 (d, 1H), 3.91 (t, 2H and br, 1H), 3.04 (t, 2H), 2.49 (s, 3H).

25.B. Synthesis of (1-Ethyl-8-methyl-1,3,4,9-tetrahydro-pyrano[3,4-b]indol-1-yl)-acetic acid ethyl ester Following the procedure of example 23.B. except using 2-(7-methyl-1H-indol-3-yl)-ethanol as the 3-indolethanol component afforded the title compound as solid. mp. 77-78 ° C. ¹H NMR (500 MHz, CDCl₃) δ 9.04 (br, 1H), 7.36 (d, 1H), 7.02 (t, 1H), 6.97 (d, 1H), 4.19 (m, 2H), 4.04 (m, 1H), 3.94 (m, 1H), 2.98 (d, 1H), 2.90 (d, 1H), 2.81 (m, 1H), 2.75 (dt, 1H), 2.49 (s, 3H), 2.15 (m, 1H), 2.02 (m, 1H), 1.27 (t, 3H), 0.83 (t, 3H); ESI (−) MS m/e=300 (MH⁻).

25.C. Synthesis of 2-(1-Ethyl-8-methyl-1,3,4,9-tetrahydro-pyrano[3,4-b]indol-1-yl)-ethanol Following the procedure of example 22.C. except using (1-ethyl-8-methyl-1,3,4,9-tetrahydro-pyrano[3,4-b]indol-1-yl)-acetic acid ethyl ester as the carboxylic acid component afforded the title compound as a solid. mp. 68° C. ¹H NMR (500 MHz, CDCl₃) δ 7.68 (br, 1H), 7.37 (d, 1H), 7.05 (t, 1H), 6.98 (d, 1H), 4.06 (m, 1H), 3.98 (m, 1H), 3.70 (m, 1H), 3.65 (m, 1H), 2.88 (m, 1H), 2.76 (t, 1H), 2.72 (m, 1H), 2.47 (s, 3H), 2.21 (m, 1H), 2.07 (m, 1H), 2.00 (m, 1H), 1.91 (m, 1H), 0.94 (t, 3H); ESI (+) MS m/e=260 (MH⁺), ESI (−) MS m/e=258 (MH⁻).

COMPOUND 26: 2-(1-ETHYL-8-FLUORO-1,3,4,9-TETRAHYDRO-PYRANO[3,4-B]INDOL-1-YL)-ETHANOL

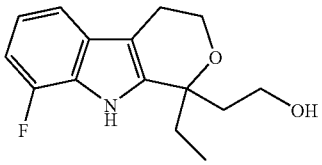

26.A. Synthesis of 2-(7-Fluoro-1H-indol-3-yl)-ethanol

Following the procedure of example 24.A. except using 2-fluorophenylhydrazine hydrochloride as the hydrazine component afforded the title compound as an oil.

26.B. Synthesis of (1-Ethyl-8-fluoro-1,3,4,9-tetrahydropyrano[3,4-b]indol-1-yl)-acetic acid ethyl ester Following the procedure of 24.B. except using 2-(7-fluoro-1H-indol-3-yl)-ethanol as the 3-indolethanol component afforded the title compound as an oil.

26.C. Synthesis of 2-(1-Ethyl-8-fluoro-1,3,4,9-tetrahydro-pyrano[3,4-b]indol-1-yl)-ethanol Following the procedure of example 22.C. except using (1-ethyl-8-fluoro-1,3,4,9-tetrahydro-pyrano[3,4-b]indol-1-yl)-acetic acid ethyl ester as the carboxylic acid component afforded the title compound as a solid. $^1$H NMR (500 MHz, CDCl$_3$) δ 8.18 (br, 1H), 7.27 (d, 1H), 7.02 (m, 1H), 6.89 (dd, 1H), 4.07 (m, 1H), 3.99 (m, 1H), 3.71 (m, 1H), 3.65 (m, 1H), 2.88 (m, 1H), 2.78 (dt, 1H), 2.76 (br, 1H), 2.22 (m, 1H), 2.07 (m, 1H), 1.99 (m, 1H), 1.91 (m, 1H), 0.94 (t, 3H); ESI (+) MS m/e=264 (MH$^+$), ESI (−) MS m/e=262 (MH$^-$).

COMPOUND 27: 2-(8-CHLORO-1-ETHYL-1,3,4,9-TETRAHYDRO-PYRANO[3,4-B]INDOL-1-YL)-ETHANOL

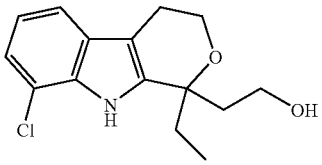

27.A. Synthesis of 2-(7-Chloro-1H-indol-3-yl)-ethanol

Following the procedure of 24.A. except using 2-chlorophenylhydrazine hydrochloride as the hydrazine component afforded the title compound as an oil. $^1$H NMR (500 MHz, CDCl$_3$) δ 8.26 (br, 1H), 7.52 (d, 1H), 7.21 (d, 1H), 7.15 (d, 1H), 7.06 (t, 1H), 3.91 (t, 2H), 3.02 (t, 2H), 1.48 (br, 1H).

27.B. Synthesis of (8-Chloro-1-ethyl-1,3,4,9-tetrahydropyrano[3,4-b]indol-1-yl)-acetic acid ethyl ester Following the procedure of 24.B. except using 2-(7-chloro-1H-indol-3-yl)-ethanol as the 3-indolethanol component afforded the title compound as a solid. $^1$H NMR (500 MHz, CDCl$_3$) δ 9.28 (br, 1H), 7.39 (d, 1H), 7.16 (d, 1H), 7.02 (t, 1H), 4.18 (m, 2H), 4.05 (m, 1H), 3.94 (m, 1H), 2.98 (d, 1H), 2.88 (d, 1H), 2.82 (m, 1H), 2.75 (dt, 1H), 2.15 (m, 1H), 2.03 (m, 1H), 1.27 (t, 3H), 0.84 (t, 3H); ESI (−) MS m/e=230 (MH$^-$).

27.C. Synthesis of (8-Chloro-1-ethyl-1,3,4,9-tetrahydropyrano[3,4-b]indol-1-yl)-acetic acid Following the procedure of example 22.B. except using (8-chloro-1-ethyl-1,3,4,9-tetrahydro-pyrano[3,4-b]indol-1-yl)-acetic acid ethyl ester as the ester component afforded the title compound as a solid. $^1$H NMR (500 MHz, CDCl$_3$) δ 8.81 (br, 1H), 7.40 (d, 1H), 7.17 (d, 1H), 7.04 (t, 1H), 4.09 (m, 1H), 4.03 (m, 1H), 3.05 (d, 1H), 3.02 (d, 1H), 2.82 (m, 2H), 2.13 (m, 1H), 2.06 (m, 1H), 0.88 (t, 3H); ESI (+) MS m/e=294 (MH$^+$), ESI (−) MS m/e=292 (MH$^-$).

27.D. Synthesis of 2-(8-Chloro-1-ethyl-1,3,4,9-tetrahydro-pyrano[3,4-b]indol-1-yl)-ethanol Following the procedure of example 22.C. except using (8-chloro-1-ethyl-1,3,4,9-tetrahydro-pyrano[3,4-b]indol-1-yl)-acetic acid as the carboxylic acid component afforded the title compound as a solid. $^1$H NMR (500 MHz, CDCl$_3$) δ 8.05 (br, 1H), 7.41 (d, 1H), 7.17 (d, 1H), 7.05 (t, 1H), 4.07 (m, 1H), 4.00 (m, 1H), 3.72 (m, 1H), 3.67 (m, 1H), 2.87 (m, 1H), 2.76 (dt, 1H), 2.70 (br, 1H), 2.23 (m, 1H), 2.03 (m, 1H), 1.91 (m, 1H), 0.94 (t, 3H); ESI (+) MS m/e=280 (MH$^+$), ESI (−) MS m/e=278 (MH$^-$).

COMPOUND 28: 2-(8-BROMO-1-ETHYL-1,3,4,9-TETRAHYDRO-PYRANO[3,4-B]INDOL-1-YL)-ETHANOL

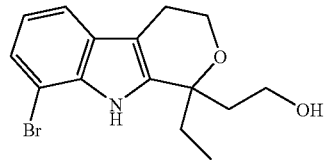

28.A. Synthesis of 2-(7-Bromo-1H-indol-3-yl)-ethanol

Following the procedure of example 24.A. except using 2-bromophenylhydrazine hydrochloride as the hydrazine component afforded the title compound as an oil.

28.B. Synthesis of (8-Bromo-1-ethyl-1,3,4,9-tetrahydropyrano[3,4-b]indol-J-yl)-acetic acid ethyl ester Following the procedure of 24.B. except using 2-(7-bromo-1H-indol-3-yl)-ethanol as the 3-indolethanol component afforded the title compound as an oil.

28.C. Synthesis of 2-(8-Bromo-1-ethyl-l, 3,4,9-tetrahydro-pyrano[3,4-b]indol-1-yl)-ethanol To a solution of (8-bromo-1-ethyl-1,3,4,9-tetrahydropyrano[3,4-b]indol-1-yl)-acetic acid ethyl ester (1.03 g, 2.8 mmol) in tetrahydrofuran at room temperature was added 2.0 M solution of lithium borohydride in tetrahydrofuran. The mixture was heated to reflux for 5 hours. It was quenched with 5% HCl solution, followed by saturated sodium bicarbonate. It was extracted with ethyl acetate, extracts were dried over magnesium sulfate, and it was evaporated to dryness. Crystallization with diethyl ether afforded 0.682 g (75%) of the title compound as a solid. $^1$H NMR (500 MHz, CDCl$_3$) δ 8.01 (br, 1H), 7.45 (d, 1H), 7.32 (d, 1H), 7.00 (t, 1H), 4.07 (m, 1H), 3.99 (m, 1H), 3.72 (m, 1H), 3.67 (m, 1H), 2.87 (m, 1H), 2.75 (dt, 1H), 2.68 (dd, 1H), 2.24 (m, 1H), 2.08 (m, 1H), 2.02 (m, 1H), 1.93 (m, IH), 0.94 (t, 3H); ESI (+) MS m/e=324 (MH$^+$), ESI (−) MS m/e=322 (MH$^-$).

COMPOUND 29: 2-(8-ETHYL-1-METHYL-1,3,4,9-TETRAHYDRO-PYRANO[3,4-B]INDOL-1-YL)-ETHANOL

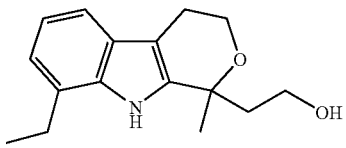

29.A. Synthesis of 2-(7-Ethyl-1H-indol-3-yl)-ethanol

Following the procedure of example 24.A. except using 2-ethylphenylhydrazine hydrochloride as the hydrazine component afforded the title compound as a solid. $^1$H NMR (500 MHz, CDCl$_3$) δ 8.05 (br, 1H), 7.50 (d, 1H), 7.08 (m, 3H), 3.92 (m, 2H), 3.04 (m, 2H), 2.86 (m, 2H), 2.06 (br, 1H), 1.35 (t, 3H); ESI (+) MS m/e=190 (MH$^+$), ESI (−) MS m/e=188 (MH$^−$).

29.B. Synthesis of (8-Ethyl-1-methyl-1,3,4,9-tetrahydro-pyrano[3,4-b]indol-1-yl)-acetic acid ethyl ester Following the procedure of example 22.A. except using 2-(7-ethyl-1H-indol-3-yl)-ethanol as the 3-indolethanol component and the ethyl acetoacetate as ketone component afforded the title compound as an oil. $^1$H NMR (500 MHz, CDCl$_3$) δ 9.16 (br, 1H), 7.35 (d, 1H), 7.01 (m, 2H), 4.17 (m, 2H), 4.02 (m, 2H), 2.85 (m, 6H), 1.57 (t, 3H), 1.36 (t, 3H), 1.29 (t, 3H); ESI (+) MS m/e=302 (MH$^+$), ESI (−) MS m/e=300 (MH$^−$).

29.C. Synthesis of (8-Ethyl-1-methyl-1,3,4,9-tetrahydro-pyrano[3,4-b]indol-1-yl)-acetic acid Following the procedure of example 1, step (b) except using (8-ethyl-1-methyl-1,3,4,9-tetrahydro-pyrano[3,4-b]indol-1-yl)-acetic acid ethyl ester as the ester component afforded the title compound as a solid. ESI (−) MS m/e=272 (MH$^−$).

29.D. Synthesis of 2-(8-Ethyl-1-methyl-1,3,4,9-tetrahydro-pyrano[3,4-b]indol-1-yl)-ethanol Following the procedure of example 22.C. except using (8-ethyl-1-methyl-1,3,4,9-tetrahydro-pyrano[3,4-b]indol-1-yl)-acetic acid as the carboxylic acid component afforded the title compound as a solid. $^1$H NMR (500 MHz, CDCl$_3$) δ 7.74 (br, 1H), 7.37 (d, 1H), 7.09 (m, 1H), 7.03 (d, 1H), 4.12 (m, 1H), 3.98 (m, 1H), 3.70 (m, 2H), 2.92 (m, 1H), 2.85 (m, 2H), 2.74 (m, 2H), 2.15 (m, 2H), 1.56 (s, 3H), 1.36 (t, 3H); ESI (+) MS m/e=282 (MNa$^+$), ESI (−) MS m/e=258 (MH$^−$).

COMPOUND 30: 2-(8-ETHYL-1-PROPYL-1,3,4,9-TETRAHYDRO-PYRANO[3,4-B]INDOL-1-YL)-ETHANOL

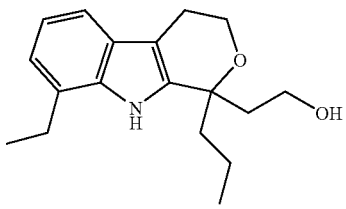

30.A. Synthesis of (8-Ethyl-1-propyl-1,3,4,9-tetrahydro-pyrano[3,4-b]indol-1-yl)-acetic acid ethyl ester Following the procedure of example 1, step (a) except using 2-(7-ethyl-1H-indol-3-yl)-ethanol as the 3-indolethanol component and the ethyl butyrylacetate as ketone component afforded the title compound as a solid. $^1$H NMR (500 MHz, CDCl$_3$) δ 9.10 (br, 1H), 7.34 (d, 1H), 7.03 (m, 2H), 4.17 (m, 2H), 4.02 (m, 1H), 3.92 (m, 1H), 2.99 (d, 1H), 2.84 (m, 3H), 2.73 (dt, 1H), 2.09 (m, 1H), 1.96 (m, 1H), 1.35 (t, 3H), 1.26 (t, 3H), 1.19 (m, 2H), 0.85 (t, 3H); ESI (+) MS m/e=330 (MH$^+$), ESI (−) MS m/e=328 (MH$^−$).

30.B. Synthesis of (8-Ethyl-1-propyl-1,3,4,9-tetrahydro-pyrano[3,4-b]indol-1-yl)-acetic acid Following the procedure of example 22.B. except using (8-ethyl-1-propyl-1,3,4,9-tetrahydro-pyrano[3,4-b]indol-1-yl)-acetic acid ethyl ester as the ester component afforded the title compound as a solid.

30.C. Synthesis of 2-(8-Ethyl-1-propyl-1,3,4,9-tetrahydro-pyrano[3,4-b]indol-1-yl)-ethanol Following the procedure of example 22.C. except using (8-ethyl-1-propyl-1,3,4,9-tetrahydro-pyrano[3,4-b]indol-1-yl)-acetic acid as the carboxylic acid component afforded the title compound as a solid. $^1$H NMR (500 MHz, CDCl$_3$) δ 7.73 (br, 1H), 7.36 (d, 1H), 7.09 (t, 1H), 7.02 (m, 1H), 4.05 (m, 1H), 4.01 (m, 1H), 3.72 (m, 1H), 3.67 (m, 1H), 2.85 (m, 2H), 2.76 (dt, 1H), 2.68 (br, 1H), 2.20 (m, 1H), 2.09 (m, 1H), 1.90 (m, 2H), 1.48 (m, 1H), 1.36 (t, 3H), 1.32 (m, 1H), 0.91 (t, 3H); ESI (+) MS m/e=288 (MH$^+$), ESI (−) MS m/e=286 (MH$^−$).

COMPOUND 31: 2-(8-ETHYL-1-ISOPROPYL-1,3,4,9-TETRAHYDRO-PYRANO[3,4-B]INDOL-1-YL)-ETHANOL

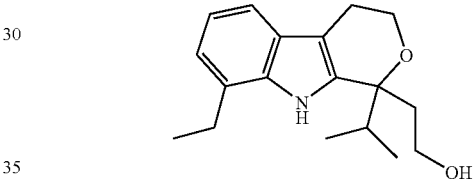

31.A. Synthesis of (8-Ethyl-1-isopropyl-1,3,4,9-tetrahydro-pyrano[3,4-b]indol-1-yl)-acetic acid ethyl ester Following the procedure of example 22.A. except using 2-(7-ethyl-1H-indol-3-yl)-ethanol as the 3-indolethanol component and ethyl iso-butyrylacetate as ketone component afforded the title compound as a solid. $^1$H NMR (500 MHz, CDCl$_3$) δ 9.12 (br, 1H), 7.36 (d, 1H), 7.07 (m, 2H), 4.13 (m, 3H), 3.81 (m, 1H), 3.04 (q, 2H), 2.87 (m, 3H), 2.66 (m, 1H), 2.56 (m, 1H), 1.37 (t, 3H), 1.25 (t, 3H), 1.05 (d, 3H), 0.69 (d, 3H).

31.B. Synthesis of (8-Ethyl-1-isopropyl-1,3,4,9-tetrahydro-pyrano[3,4-b]indol-1-yl)-acetic acid Following the procedure of example 24.B. except using (8-ethyl-1-isopropyl-1,3,4,9-tetrahydro-pyrano[3,4-b]indol-1-yl)-acetic acid ethyl ester as the ester component afforded the title compound as a solid. $^1$H NMR (500 MHz, CDCl$_3$) δ 9.70 (br, 1H), 8.55 (br, 1H), 7.36 (d, 1H), 7.07 (dd, 1H), 7.01 (d, 1H), 4.18 (m, 1H), 3.94 (m, 1H), 3.10 (q, 2H), 2.82 (m, 4H), 2.52 (m, 1H), 1.32 (t, 3H), 1.06 (d, 3H), 0.82 (d, 3H); ESI (+) MS m/e=302 (MH$^+$), ESI (−) MS m/e=300 (MH$^−$).

31.C. Synthesis of 2-(8-Ethyl-1-isopropyl-1,3,4,9-tetrahydro-pyrano[3,4-b]indol-1-yl)-ethanol Following the procedure of example 22.C. except using (8-ethyl-1-isopropyl-1,3,4,9-tetrahydro-pyrano[3,4-b]indol-1-yl)-acetic acid as the carboxylic acid component afforded the title compound as a solid. $^1$H NMR (500 MHz, CDCl$_3$) δ 7.68 (br, 1H), 7.38 (d, 1H), 7.09 (dd, 1H), 7.03 (m, 1H), 4.06 (m, 2H), 3.65 (m, 2H), 2.87 (m, 3H), 2.77 (dt, 1H), 2.68 (br, 1H), 2.32 (m, 1H), 2.23 (m, 1H), 2.05 (m, 1H), 1.35 (t, 3H), 1.05 (d, 3H), 1.00 (d, 3H); ESI (+) MS m/e=288 (MH+), ESI (−) MS m/e=286 (MH−).

COMPOUND 32: 2-(8-Ethyl-1-phenyl-1,3,4,9-tetrahydro-pyrano[3,4-b]indol-1-yl)-ethanol

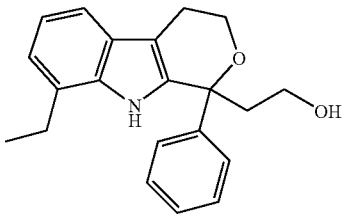

32.A. Synthesis of (8-Ethyl-1-phenyl-1,3,4,9-tetrahydro-pyrano[3,4-b]indol-1-yl)-acetic acid ethyl ester Following the procedure of example 22.A. except using 2-(7-ethyl-1H-indol-3-yl)-ethanol as the 3-indolethanol component and ethyl benzoylacetate as ketone component afforded the title compound as a solid. $^1$H NMR (500 MHz, CDCl$_3$) δ 10.05 (br, 1H), 7.42 (d, 1H), 7.28 (m, 5H), 7.12 (m, 2H), 3.96 (m, 3H), 3.60 (m, 1H), 3.43 (d, 1H), 3.22 (d, 1H), 3.05 (m, 3H), 2.65 (dd, 1H), 1.42 (d, 3H), 1.03 (t, 3H); ESI (−) MS m/e=362 (MH−).

32.B. Synthesis of (8-Ethyl-1-phenyl-1,3,4,9-tetrahydro-pyrano[3,4-b]indol-1-yl)-acetic acid Following the procedure of example 22.B. except using (8-ethyl-1-phenyl-1,3,4,9-tetrahydro-pyrano[3,4-b]indol-1-yl)-acetic acid ethyl ester as the ester component afforded the title compound as a solid. $^1$H NMR (500 MHz, CDCl$_3$) δ 9.25 (br, 1H), 7.41 (d, 1H), 7.31 (m, 5H), 7.10 (t, 1H), 7.06 (d, 1H), 4.08 (m, 1H), 3.70 (m, 1H), 3.42 (d; 1H), 3.22 (d, 1H), 3.03 (m, 1H), 2.83 (m, 2H), 2.68(m, 1H), 1.33 (t, 3H); ESI (+) MS m/e=358 (MNa+). ESI (−) MS m/e=334 (MH−).

32.C. Synthesis of 2-(8-Ethyl-1-phenyl-1,3,4,9-tetrahydro-pyrano[3,4-b]indol-1-yl)-ethanol Following the procedure of example 22.C. except using (8-ethyl-1-phenyl-1,3,4,9-tetrahydro-pyrano[3,4-b]indol-1-yl)-acetic acid as the carboxylic acid component afforded the title compound as a solid. $^1$H NMR (500 MHz, CDCl$_3$) δ 8.27 (br, 1H), 7.38 (m, 3H), 7.32 (m, 3H), 7.12 (t, 1H), 7.08 (d, 1H), 4.12 (m, 2H), 3.99 (dd, 1H), 3.61 (ddd, 1H), 3.01 (m, 1H), 2.94 (q, 2H), 2.61 (m, 2H), 2.47(m, 1H), 1.39 (t, 3H).

COMPOUND 34: [8'-ETHYL-4',9'-DIHYDRO-3'H-SPIRO(CYCLOHEXANE-1,1'-PYRANO[3,4-B]INDOL)-4-YL]-METHANOL

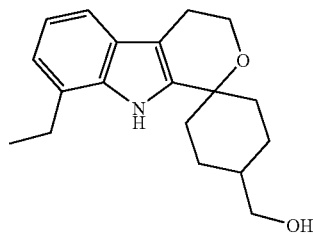

34.A. Synthesis of 8'-Ethyl-4',9'-dihydro-3'H-spiro(cyclohexane-1,1'-pyrano[3,4-b]indole)-4-carboxylic acid ethyl ester Following the procedure of example 24.A. except using 2-(7-ethyl-1H-indol-3-yl)-ethanol as the 3-indolethanol component and 4-oxo-cyclohexane carboxylic acid ethyl ester as ketone component afforded the title compound as an oil. ESI (+) MS m/e=342 (MH+), ESI (−) MS m/e=340 (MH−).

34.B. Synthesis of 8'-Ethyl-4',9'-dihydro-3'H-spiro(cyclohexane-1,1'-pyrano[3,4-b]indole)-4-carboxylic acid Following the procedure of example 22.B. except using 8'-ethyl-4',9'-dihydro-3'H-spiro(cyclohexane-1,1'-pyrano[3,4-b]indole)-4-carboxylic acid ethyl ester as the ester component afforded the title compound as a solid. ESI (+) MS m/e=314 (MH+), ESI (−) MS m/e=312 (MH−).

34.C. Synthesis of [8'-Ethyl-4',9'-dihydro-3'H-spiro(cyclohexane-1,1'-pyrano[3,4-b]indol)-4-yl]-methanol Following the procedure of example 22.C. except using 8'-ethyl-4',9'-dihydro-3'H-spiro(cyclohexane-1,1'-pyrano[3,4-b]indole)-4-carboxylic acid as the carboxylic acid component afforded the title compound as a solid. $^1$H NMR (500 MHz, CDCl$_3$) δ 7.51 (br, 1H), 7.33 (d, 1H), 7.06 (t, 1H), 7.00 (d, 1H), 3.97 (t, 2H), 3.54 (t, 2H), 2.84 (q, 2H), 2.78 (t, 2H), 2.12 (br, 1H), 2.09 (m, t, 1H), 1.69 (m, 4H), 1.60 (m, 1H), 1.52 (m, 3H), 1.35 (t, 3H); ESI (+) MS m/e=300 (MH+), ESI (−) MS m/e=298 (MH−).

COMPOUND 35: R-2-(1,8-DIETHYL-1,3,4,9-TETRAHYDRO-PYRANO[3,4-B]INDOL-1-YL)-ETHANOL

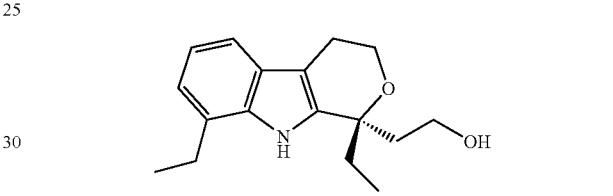

35.A. Synthesis of R-2-(1,8-Diethyl-1,3,4,9-tetrahydro-pyrano[3,4-b]indol-1-yl)-ethanol Following the procedure of example 22, except using R-(1,8-Diethyl-1,3,4,9-tetrahydro-pyrano[3,4-b]indol-1-yl)-acetic acid as the carboxylic acid component in step 22.C. afforded the title compound as a solid. $^1$H NMR (500 MHz, CDCl$_3$) δ 7.74 (br, 1H), 7.37 (d, 1H), 7.09 (t, 1H), 7.03 (d, 1H), 4.07 (m, 1H), 3.98 (m, 1H), 3.68 (m, 2H), 2.86 (m, 3H), 2.76 (dt, 1H), 2.69 (br, t, 1H), 2.21 (m, 1H), 2.07 (m, 1H), 2.00 (m, 1H), 1.91 (m, 1H), 1.35 (t, 3H), 0.94 (t, 3H); ESI (+) MS m/e=274 (MH+), ESI (−) MS m/e=272 (MH−).

COMPOUND 36: 2-(1-ETHYL-8-ISOPROPYL-1,3,4,9-TETRAHYDRO-PYRANO[3,4-B]INDoL-1-YL)-ETHANOL

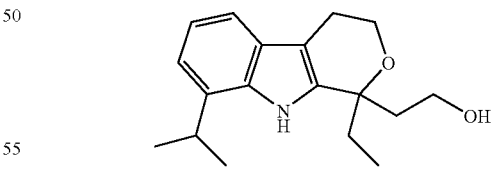

36.A. Synthesis of 2-Hydroxyimino-N-(2-isopropyl-phenyl)-acetamide

A mixture of 2-isopropylaniline (4.7 g, 35 mmol), Na$_2$SO$_4$ (30.0 g), concentrated hydrochloride (3 mL), chloral hydrate (6.5 g), hydroxylamine hydrochloride (8.00 g) in water (150 mL) was heated at 85° C. for 40 minutes. After cooling to room temperature, it was extracted with ethyl acetate. The extracts were dried over magnesium sulfate and evaporated to dryness. Flash chromatography on silica gel provided 4.357 g (54%) of the title compound as solid.

36.B. Synthesis of 7-Isopropyl-1H-indole-2,3-dione

To concentrated sulfuric acid at 80° C. was added 2-hydroxyimino-N-(2-isopropyl-phenyl)-acetamide in several small portions over 10 minutes. After addition it was heated at 80° C. for 30 minutes., then poured into ice. Filtration, washing with water, and drying under vacuum over $P_2O_5$ provided 2.974 g (84%) of the title compound as a solid. ESI (−) MS m/e=188 (MH−).

36.C. Synthesis of (7-Isopropyl-1H-indol-3-yl)-oxo-acetic acid ethyl ester

To a solution of 7-isopropyl-1H-indole-2,3-dione (2.97 g, 15.7 mmol) in tetrahydrofuran (20 mL) was dropped 2.0 M solution of lithium borohydride in tetrahydrofuran (15 mL, 30 mmol). The mixture was heated at 90° C. for 4 hours. It was quenched with 5% HCl, followed by saturated sodium bicarbonate. It was extracted with ethyl acetate. The extracts were dried over magnesium sulfate and evaporated to dryness to provide a crude 7-isopropyl-1H-indole. To a solution of the crude 7-isopropyl-1H-indole in diethyl ether (40 mL) was dropped 2.0 M solution of oxalyl chloride in dichloromethane (15 mL, 30 mmol). After stirring at room temperature for 5 hours, it was evaporated to dryness. Ethanol was added to the residue and it was stirred at room temperature overnight. After the ethanol was evaporated, flash chromatography on silica gel provided 0.972 g (24%) of the title compound as solid. ESI (−) MS m/e=258 (MH−).

36.D. Synthesis of (1-Ethyl-8-isopropyl-1,3,4,9-tetrahydro-pyrano[3,4-b]indol-1-yl)-acetic acid ethyl ester To a solution of (7-isopropyl-1H-indol-3-yl)-oxo-acetic acid ethyl ester (0.97 g. 3.7 mmol) in tetrahydrofuran was added 2.0 M solution of lithium borohydride in tetrahydrofuran. The mixture was heated at 90° C. for 5 hours. It was quenched with 5% HCl, followed by saturated sodium bicarbonate. It was extracted with ethyl acetate. The extracts were dried over magnesium sulfate and evaporated to dryness to provide a crude 2-(7-isopropyl -1H-indol-3-yl)-ethanol. ESI (+) MS m/e=204 (MH+), ESI (−) MS m/e=202 (MH−).

Following the procedure of example 24.B. except using 2-(7-isopropyl-1H-indol-3-yl)-ethanol as the 3-indolethanol component afforded the title compound as an oil. ESI (+) MS m/e=330 (MH+), ESI (−) MS m/e=328 (MH−).

36.E. Synthesis of (1-Ethyl-8-isopropyl-1,3,4,9-tetrahydro-pyrano[3,4-b]indol-1-yl)-acetic acid Following the procedure of example 22.B. except using (1-ethyl-8-isopropyl-1,3,4,9-tetrahydro-pyrano[3,4-b]indol-1-yl)-acetic acid ethyl ester as the ester component afforded the title compound as a solid. mp. 158-159° C. $^1$H NMR (500 MHz, CDCl$_3$) δ 9.50 (br, 1H), 8.58 (br, 1H), 7.36 (d, 1H), 7.08 (m, 2H), 4.09 (m, 1H), 4.04 (m, 1H), 3.20 (m, 1H), 3.05 (d, 1H), 3.02 (d, 1H), 2.84 (m, 2H), 2.13 (m, 1H), 2.04 (m, 1H), 1.38 (d, 3H), 1.35 (d, 3H), 0.88 (t, 3H); ESI (+) MS m/e=302 (MH+), ESI (−) MS m/e=300 (MH−).

36.F. Synthesis of 2-(1-Ethyl-8-isopropyl-1,3,4,9-tetrahydro-pyrano[3,4-b]indol-1-yl)-ethanol Following the procedure of example 22.C. except using (1-ethyl-8-isopropyl-1,3,4,9-tetrahydro-pyrano[3,4-b]indol-1-yl)-acetic acid as the carboxylic acid component afforded the title compound as a oil. $^1$H NMR (500 MHz, CDCl$_3$) δ 7.78 (br, 1H), 7.36 (d, 1H), 7.11 (t, 1H), 7.07 (d, 1H), 4.07 (m, 1H), 3.99 (m, 1H), 3.71 (m, 2H), 3.20 (m, 2H), 2.90 (m, 1H), 2.76 (dt, 1H), 2.65 (br, 1H), 2.22 (m, 1H), 2.06 (m, 1H), 2.03 (m, 1H), 1.92 (m, 1H), 1.38 (d, 6H), 0.88 (t, 3H); ESI (+) MS m/e=288 (MH+), ESI (−) MS m/e=286 (MH−).

COMPOUND 37: 2-(1-ETHYL-8-TRIFLUOROMETHYL-1,3,4,9-TETRAHYDRO-PYRANO[3,4-B]INDOL-1-YL)-ETHANOL

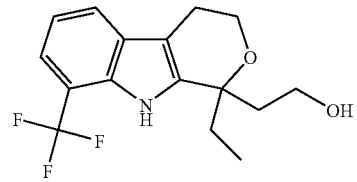

37.A. Synthesis of2-Hydroxyimino-N-(2-trifluoromethyl-phenyl)-acetamide

Following the procedure of example 36.A. except using 2-trifluoromethylaniline as the aniline component afforded the title compound as a solid.

37.B. Synthesis of 7-Trifluoromethyl-1H-indole-2,3-dione

Following the procedure of example 36.B. except using 2-hydroxyimino-N-(2-trifluoromethyl-phenyl)-acetamide as the acetamide component afforded the title compound as a solid. ESI (−) MS m/e=214 (MH−).

37.C Synthesis of (7-Trifluoromethyl-1H-indol-3-yl)-oxo-acetic acid ethyl ester

Following the procedure of example 36.C. except using 7-trifluoromethyl-1H-indole-2,3-dione as the dione component afforded the title compound as a solid.

37.D. Synthesis of 2-(1-Ethyl-8-trifluoromethyl-1,3,4,9-tetrahydro-pyrano[3,4-b]indol-1-yl)-ethanol Following the procedure of example 28.C. except using (1-ethyl-8-trifluoromethyl-1,3,4,9-tetrahydro-pyrano[3,4-b] indol-1-yl)-acetic acid ethyl ester as the ester component afforded the title compound as a solid. $^1$H NMR (500 MHz, CDCl$_3$) δ 8.42 (br, 1H), 7.67 (d, 1H), 7.41 (d, 1H), 7.18 (t, 1H), 4.07 (m, 1H), 4.00 (m, 1H), 3.71 (m, 2H), 2.89 (m, 1H), 2.78 (dt, 1H), 2.64 (br, 1H), 2.23 (m, 1H), 2.07 (m, 1H), 2.02 (m, 1H), 1.93 (m, 1H), 0.93 (t, 3H); ESI (+) MS m/e=314 (MH+), ESI (−) MS m/e=312 (MH−).

COMPOUND 38: 2-(5-CHLORO-1-ETHYL-1,3,4,9-TETRAHYDRO-PYRANO[3,4-B]INDOL-1-YL)-ETHANOL

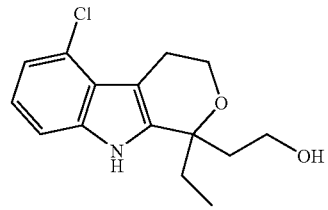

38.A. Synthesis of (4-Chloro-1H-indol-3-yl)-oxo-acetic acid ethyl ester

Following the procedure of example 36.C. except using 4-chloro-1H-indole as the indole component afforded the title compound as a solid.

38.B. Synthesis of 5-Chloro-1-ethyl-1,3,4,9-tetrahydro-pyrano[3,4-b]indol-1-yl)-acetic acid ethyl ester Following the procedure of example 36.D. except using (4-chloro-1H-indol-3-yl)-oxo-acetic acid ethyl ester as the ester component afforded the title compound as an oil. $^1$H NMR (008-08) MS. ESI (+) MS m/e=322 (MH+), ESI (−) MS m/e=320 (MH−).

38 C. Synthesis of (5-Chloro-1-ethyl-1,3,4,9-tetrahydro-pyrano[3,4-b]indol-1-yl)-acetic acid Following the procedure of example 22.B except using (5-chloro-1-ethyl-1,3,4,9-tetrahydro-pyrano[3,4-b]indol-1-yl)-acetic acid ethyl ester as the ester component afforded the title compound as a solid. ESI (+) MS m/e=294 (MH⁺), ESI (–) MS m/e=292 (MH⁻).

38.D. Synthesis of 2-(5-Chloro-1-ethyl-1,3,4,9-tetrahydro-pyrano[3,4-b]indol-1-yl)-ethanol Following the procedure of example 22.C. except using (5-chloro-1-ethyl-1,3,4,9-tetrahydro-pyrano[3,4-b]indol-1-yl)-acetic acid as the carboxylic acid component afforded the title compound as a solid. $^1$H NMR (500 MHz, CDCl$_3$) δ 8.04 (br, 1H), 7.20 (dd, 1H), 7.04 (m, 2H), 4.05 (m, 1H), 3.97 (m, 1H), 3.68 (m, 2H), 3.16 (m, 2H), 2.19 (m, 1H), 2.04 (m, 1H), 1.98 (m, 1H), 1.89 (m, 1H), 0.92 (t, 3H); ESI (–) MS m/e=278 (MH⁻).

COMPOUND 39: 2-(1-ETHYL-5-FLUORO-1,3,4,9-TETRAHYDRO-PYRANO[3,4-B]INDOL-1-YL)-ETHANOL

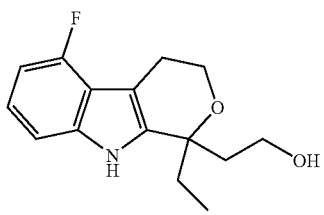

39.A. Synthesis of (4-Fluoro-1H-indol-3-yl)-oxo-acetic acid ethyl ester

Following the procedure of example 36.C. except using 4-fluoro-1H-indole as the indole component afforded the title compound as a solid.

39.B. Synthesis of (1-Ethyl-5-fluoro-1,3,4,9-tetrahydro-pyrano[3,4-b]indol-1-yl)-acetic acid ethyl ester Following the procedure of example 36.D. except using (4-fluoro-1H-indol-3-yl)-oxo-acetic acid ethyl ester as the ester component afforded the title compound as an oil. ESI (–) MS m/e=304 (MH⁻).

39.C. (1-Ethyl-5-fluoro-1,3,4,9-tetrahydro-pyrano[3,4-b]indol-1-yl)-acetic acid

Following the procedure of example 22.B. except using (1-ethyl-5-fluoro-1,3,4,9-tetrahydro-pyrano[3,4-b]indol-1-yl)-acetic acid ethyl ester as the ester component afforded the title compound as a solid. $^1$H NMR (500 MHz, CDCl$_3$) δ 9.70 (br, 1H), 8.75 (br, 1H), 7.06 (m, 2H), 6.73 (dd, 1H), 4.08 (m, 1H), 4.04 (m, 1H), 3.00 (m, 4H), 2.10 (m, 1H), 2.01 (m, 1H), 0.86 (t, 3H); ESI (+) MS m/e=278 (MH⁺), ESI (–) MS m/e=276 (MH⁻).

39.D. Synthesis of 2-(J1Ethyl-5-fluoro-1,3,4,9-tetrahydro-pyrano[3,4-b]indol-1-yl)-ethanol Following the procedure of example 22.C. except using (1-ethyl-5-fluoro-1,3,4,9-tetrahydro-pyrano[3,4-b]indol-1-yl)-acetic acid as the carboxylic acid component afforded the title compound as a solid. $^1$H NMR (500 MHz, CDCl$_3$) δ 7.97 (br, 1H), 7.08 (m, 1H), 7.04 (ddd, 1H), 6.75 (dd, 1H), 4.04 (m, 1H), 3.98 (m, 1H), 3.67 (m, 2H), 3.04 (m, 1H), 2.93 (m, 1H), 2.61 (br, 1H), 2.19 (m, 1H), 2.03 (m, 1H), 2.01 (m, 1H), 1.89 (m, 1H), 0.92 (t, 3H); ESI (+) MS m/e=264 (MH⁺), ESI (–) MS m/e=262 (MH⁻).

COMPOUND 40: 2-(1-ETHYL-6-FLUORO-1,3,4,9-TETRAHYDRO-PYRANO[3,4-B]INDOL-1-YL)-ETHANOL

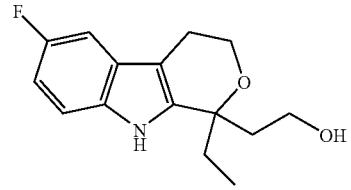

40.A. Synthesis of (5-Fluoro-1H-indol-3-yl)-oxo-acetic acid ethyl ester

Following the procedure of example 36.C. except using 5-fluoro-1H-indole as the indole component afforded the title compound as a solid.

40.B. Synthesis of (1-Ethyl-6-fluoro-1,3,4,9-tetrahydro-pyrano[3,4-b]indol-1-yl)-acetic acid ethyl ester Following the procedure of example 36.D. except using (5-fluoro-1H-indol-3-yl)-oxo-acetic acid ethyl ester as the ester component afforded the title compound as an oil.

40.C. Synthesis of 2-(1-Ethyl-6-fluoro-1,3,4,9-tetrahydro-pyrano[3,4-b]indol-1-yl)-ethanol Following the procedure of example 22.C. except using (1-ethyl-6-fluoro-1,3,4,9-tetrahydro-pyrano[3,4-b]indol-1-yl)-acetic acid ethyl ester as the carboxylic acid component afforded the title compound as a solid. $^1$H NMR (500 MHz, CDCl$_3$) δ 7.91 (br, 1H), 7.22 (dd, 1H), 7.14 (dd, 1H), 6.90 (ddd, 1H), 4.05 (m, 1H), 4.00 (m, 1H), 3.68 (m, 2H), 2.71 (dt, 1H), 2.69 (br, 1H), 2.18 (m, 1H), 2.04 (m, 1H), 1.97 (m, 1H), 1.89 (m, 1H), 0.92 (t, 3H; ESI (+) MS m/e=264 (MH⁺), ESI (–) MS m/e=262 (MH⁻).

COMPOUND 41: 2-(6-CHLORO-1-ETHYL-1,3,4,9-TETRAHYDRO-PYRANO[3,4-B]INDOL-1-YL)-ETHANOL

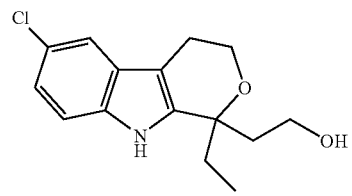

41.A. Synthesis of (5-Chloro-1H-indol-3-yl)-oxo-acetic acid ethyl ester

Following the procedure of example 36.C. except using 5-chloro-1H-indole as the indole component afforded the title compound as a solid. $^1$H NMR(500 MHz, DMSO-d$_6$) δ 12.54 (br, 1H), 8.50 (d, 1H), 8.12 (d, 1H), 7.56 (d, 1H), 7.30 (dd, 1H), 4.36 (q, 2H), 2.48 (t, br, 1H), 1.32 (t, 3H); APCI (–) MS m/e=250 (MH⁻).

41.B. Synthesis of (6-Chloro-1-ethyl-1,3,4,9-tetrahydro-pyrano[3,4-b]indol-1-yl)-acetic acid ethyl ester Following the procedure of example 36.D. except using (5-chloro-1H-indol-3-yl)-oxo-acetic acid ethyl ester as the ester component afforded the title compound as an oil. $^1$H NMR (500 MHz, CDCl$_3$) δ 9.18 (br, 1H), 7.46 (d, 1H), 7.26 (d, 1H), 7.11 (dd, 1H), 4.19 (m, 2H), 4.03 (m, 1H), 3.93 (m, 1H), 2.99 (d, 1H), 2.90 (d, 1H), 2.77 (m, 1H), 2.72 (m, 1H), 2.11 (m, 1H), 1.98 (m, 1H), 1.27 (t, 3H), 0.81 (t, 3H); APCI (+) MS m/e=322 (MH⁺), APCI (–) MS m/e=320(MH⁻).

41.C Synthesis of (6-Chloro-1-ethyl-1,3,4,9-tetrahydro-pyrano[3,4-b]indol-1-yl)-acetic acid Following the procedure of example 22.B. except using (6-chloro-1-ethyl-1,3,4,9-tetrahydro-pyrano[3,4-b]indol-1-yl)-acetic acid ethyl ester as the ester component afforded the title compound as a solid. $^1$H NMR (500 MHz, CDCl$_3$) δ 9.50 (br, 1H), 8.68 (br, 1H), 7.46 (s, 1H), 7.23 (d, 1H), 7.12 (d, 1H), 4.09 (m, 1H), 4.03 (m, 1H), 3.03 (d, 1H), 2.99 (d, 1H), 2.79 (m, 2H), 2.10 (m, 1H), 2.01 (m, 1H), 0.86 (t, 3H); ESI (+) MS m/e=294 (MH$^+$), ESI (−) MS m/e=292 (MH$^-$).

41.D. Synthesis of2-(6-Chloro-1-ethyl-1,3,4,9-tetrahydro-pyrano[3,4-b]indol-1-yl)-ethanol Following the procedure of example 22.C. except using (6-chloro-1-ethyl-1,3,4,9-tetrahydro-pyrano[3,4-b]indol-1-yl)-acetic acid as the carboxylic acid component afforded the title compound as a solid. $^1$H NMR (500 MHz, CDCl$_3$) δ 8.01 (br, 1H), 7.46 (s, 1H), 7.22 (d, 1H), 7.12 (d, 1H), 4.05 (m, 1H), 3.99 (m, 1H), 3.67 (m, 2H), 2.83 (m, 1H), 2.72 (m, 1H), 2.65 (br, 1H), 2.19 (m, 1H), 2.00 (m, 2H), 1.88 (m, 1H), 0.92 (t, 3H); APCI (+) MS m/e=280 (MH$^+$), APCI (−) MS m/e=278 (MH$^-$).

COMPOUND 42: 2-(6-BROMO-1-ETHYL-1,3,4,9-TETRAHYDRO-PYRANO[3,4-B]INDOL-1-YL)-ETHANOL

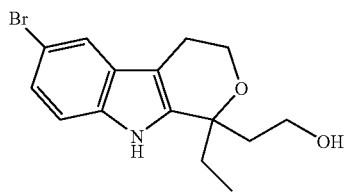

42.A. Synthesis of (5-Bromo-1H-indol-3-yl)-oxo-acetic acid ethyl ester

Following the procedure of example 36, step (c) except using 5-bromo-1H-indole as the indole component afforded the title compound as a solid.

42.B. Synthesis of (6-Bromo-1-ethyl-1,3,4,9-tetrahydro-pyrano[3,4-b]indol-1-yl)-acetic acid ethyl ester Following the procedure of example 36.B. except using (5-bromo-1H-indol-3-yl)-oxo-acetic acid ethyl ester as the ester component afforded the title compound as an oil.

42.C. Synthesis of 2-(6-Bromo-1-ethyl-1,3,4,9-tetrahydro-pyrano[3,4-b]indol-1-yl)-ethanol Following the procedure of example 28.C. except using (6-bromo-1-ethyl-1,3,4,9-tetrahydro-pyrano[3,4-b]indol-1-yl)-acetic acid ethyl ester as the ester component afforded the title compound as a solid. $^1$H NMR (500 MHz, CDCl$_3$) δ 7.95 (br, 1H), 7.62 (d, 1H), 7.24 (dd, 1H), 7.19 (d, 1H), 4.05 (m, 1H), 3.97 (m, 1H), 3.67 (m, 2H), 2.84 (m, 1H), 2.71 (m, 1H), 2.55 (br, 1H), 2.19 (m, 1H), 2.03 (m, 1H), 1.97 (m, 1H), 1.88 (m, 1H), 0.91 (t, 3H); ESI (+) MS m/e=324 (MH$^+$), ESI (−) MS m/e=322 (MH$^-$).

COMPOUND 43: 2-(1-ETHYL-7-FLUORO-1,3,4,9-TETRAHYDRO-PYRANO[3,4-B]INDOL-1-YL)-ETHANOL

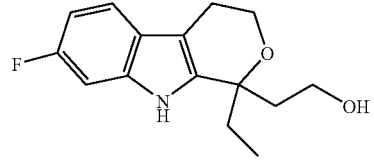

43.A. Synthesis of (6-Fluoro-1H-indol-3-yl)-oxo-acetic acid ethyl ester

Following the procedure of example 36.C. except using 6-fluoro-1H-indole as the indole component afforded the title compound as a solid. $^1$H NMR (500 MHz, CDCl$_3$) δ 8.75 (br, 1H), 8.48 (d, 1H), 8.39 (dd, 1H), 7.12 (m, 2H), 4.41 (q, 2H), 1.43 (t, 3H); ESI (−) MS m/e=234(MH$^-$).

43.B. Synthesis of (1-Ethyl-7-fluoro-1,3,4,9-tetrahydro-pyrano[3,4-b]indol-1-yl)-acetic acid ethyl ester Following the procedure of example 36.D. except using (6-fluoro-1H-indol-3-yl)-oxo-acetic acid ethyl ester as the ester component afforded the title compound as an oil.

43.C. Synthesis of (1-Ethyl-7-fluoro-1,3,4,9-tetrahydro-pyrano[3,4-b]indol-1-yl)-acetic acid Following the procedure of example 22.B. except using (1-ethyl-7-fluoro-1,3,4,9-tetrahydro-pyrano[3,4-b]indol-1-yl)-acetic acid ethyl ester as the ester component afforded the title compound as a solid. $^1$H NMR (500 MHz, CDCl$_3$) δ 11.8 (br, 1H), 9.53 (br, 1H), 7.29 (dd, 1H), 6.93 (dd, 1H), 6.74 (ddd, 1H), 3.94 (m, 1H), 3.89 (m, 1H), 2.86 (d, 1H), 2.82 (d, 1H), 2.69 (m, 1H), 2.66 (m, 1H), 2.03 (m, 1H), 1.95 (m, 1H), 0.74 (t, 3H); ESI (+) MS m/e=278 (MH$^+$), ESI (−) MS m/e=276 (MH$^-$).

43.D. Synthesis of2-(1-Ethyl-7-fluoro-1,3,4,9-tetrahydro-pyrano[3,4-b]indol-1-yl)-ethanol Following the procedure of example 22.C. except using (1-ethyl-7-fluoro-1,3,4,9-tetrahydro-pyrano[3,4-b]indol-1-yl)-acetic acid as the carboxylic acid component afforded the title compound as a solid. $^1$H NMR (500 MHz, CDCl$_3$) δ 7.95 (br, 1H), 7.40 (dd, 1H), 7.00 (dd, 1H), 6.88 (ddd, 1H), 4.06 (m, 1H), 3.99 (m, 1H), 3.65 (m, 2H), 2.85 (m, 1H), 2.71 (m, br, 2H), 2.18 (m, 1H), 2.02 (m, 1H), 1.98 (m, 1H), 1.88 (m, 1H), 0.92 (t, 3H); ESI (+) MS m/e=264 (MH$^+$), ESI (−) MS m/e=262 (MH$^-$).

COMPOUND 44: 2-(7-CHLORO-1-ETHYL-1,3,4,9-TETRAHYDRO-PYRANO[3,4-B]INDOL-1-YL)-ETHANOL

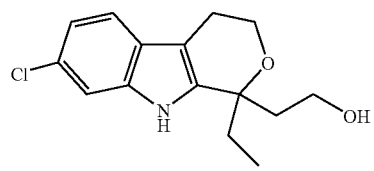

44.A. Synthesis of (6-Chloro-1H-indol-3-yl)-oxo-acetic acid ethyl ester

Following the procedure of example 36.c. except using 6-chloro-1H-indole as the indole component afforded the title compound as a solid. $^1$H NMR (500 MHz, CDCl$_3$) δ 11.50 (br, 1H), 8.30 (d, 1H), 8.21 (d, 1H), 7.37 (d, 1H), 7.15 (dd, 1H), 4.31 (q, 2H), 1.33 (t, 3H); ESI (+) MS m/e=252 (MH$^+$), ESI (−) MS m/e=250(MH$^-$).

44.B. Synthesis of (7-Chloro-1-ethyl-1,3,4,9-tetrahydro-pyrano[3,4-b]indol-1-yl)-acetic acid ethyl ester Following the procedure of example 22.D. except using (6-chloro-1H-indol-3-yl)-oxo-acetic acid ethyl ester as the ester component afforded the title compound as an oil.

44.C. Synthesis of (7-Chloro-1-ethyl-1,3,4,9-tetrahydro-pyrano[3,4-b]indol-1-yl)-acetic acid Following the procedure of example 22.B. except using (7-chloro-1-ethyl-1,3,4,9-tetrahydro-pyrano[3,4-b]indol-1-yl)-acetic acid ethyl ester as the ester component afforded the title compound as a solid. $^1$H NMR (500 MHz, CDCl$_3$) δ 11.80 (br, 1H), 9.57 (br, 1H), 7.30 (d, 1H), 7.24 (d, 1H), 6.95 (dd, 1H), 3.97 (m, 1H), 3.88 (m, 1H), 2.88 (d, 1H), 2.80 (d, 1H), 2.71 (m, 1H), 2.66 (dt, 1H), 2.04 (m, 1H), 1.96 (m, 1H), 0.74 (t, 3H); ESI (+) MS m/e=294 (MH$^+$), ESI (−) MS m/e=292 (MH$^-$).

44.D. Synthesis of 2-(7-Chloro-1-ethyl-1,3,4,9-tetrahydro-pyrano[3,4-b]indol-1-yl)-ethanol Following the procedure of example 22.C. except using (7-chloro-1-ethyl-1,3,4,9-tetrahydro-pyrano[3,4-b]indol-1-yl)-acetic acid as the carboxylic acid component afforded the title compound as a solid. $^1$H NMR (500 MHz, CDCl$_3$) δ 8.02 (br, 1H), 7.40 (d, 1H), 7.30 (d, 1H), 7.08 (dd, 1H), 4.05 (m, 1H), 3.99 (m, 1H), 3.66 (m, 2H), 2.73 (dt, 1H), 2.71 (br, 1H), 2.11 (m, 1H), 2.02 (m, 1H), 1.96 (m, 1H), 1.88 (m, 1H), 0.91 (t, 3H); ESI (+) MS m/e=280 (MH$^+$), ESI (−) MS m/e=278 (MH$^-$).

COMPOUND 45: 2-(1-ETHYL-6,8-DIMETHYL-1,3,4,9-TETRAHYDRO-PYRANO[3,4-B]INDOL-1-YL)-ETHANOL

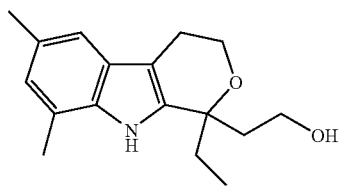

45.A. Synthesis of 5,7-Dimethyl-1H-indole

To solution of 5,7-dimethyl-1H-indole-2,3-dione in tetrahydrofuran at 0° C. was added 1.0 M solution of borane-tetrahydrofuran complex in tetrahydrofuran (40 mL). After stirred at room temperature overnight, a 5% HCl solution was added to the mixture and it was stirred 20 minutes. It was neutralized with saturated sodium bicarbonate solution and extracted with ethyl acetate. Extracts were dried over magnesium sulfate and evaporated to dryness to afford the title compound as oil.

45.B. Synthesis of (5,7-Dimethyl-1H-indol-3-yl)-oxo-acetic acid ethyl ester

Following the procedure of example 36.C. except using 5,7-dimethyl-1H-indole as the indole component afforded the title compound as a solid. ESI (+) MS m/e=246 (MH$^+$).

45.C. Synthesis of (1-Ethyl-6,8-dimethyl-1,3,4,9-tetrahydro-pyrano[3,4-b]indol-1-yl)-acetic acid ethyl ester Following the procedure of example 36.D. except using (5,7-dimethyl-1H-indol-3-yl)-oxo-acetic acid ethyl ester component afforded the title compound as an oil.

45.D. Synthesis of (1-Ethyl-6,8-dimethyl-1,3,4,9-tetrahydro-pyrano[3,4-b]indol-1-yl)-acetic acid Following the procedure of example 22.B. except using (1-ethyl-6,8-dimethyl-1,3,4,9-tetrahydro-pyrano[3,4-b]indol-1-yl)-acetic acid ethyl ester as the ester component afforded the title compound as a solid. $^1$H NMR (500 MHz, CDCl$_3$) δ 9.50 (br, 1H), 8.28 (br, 1H), 7.14 (s, 1H), 6.82 (s, 1H), 4.10 (m, 1H), 4.06 (m, 1H), 3.02 (d, 2H), 3.01 (d, 1H), 2.81 (m, 2H), 2.41 (s, 3H), 2.40 (s, 3H), 2.10 (m, 1H), 2.03 (m, 1H), 0.87 (t, 3H); ESI (+) MS m/e=288 (MH$^+$), ESI (−) MS m/e=286 (MH$^-$).

45.E. Synthesis of 2-(1-Ethyl-6,8-dimethyl-1,3,4,9-tetrahydro-pyrano[3,4-b]indol-1-yl)-ethanol Following the procedure of example 22.C. except using (1-ethyl-6,8-dimethyl-1,3,4,9-tetrahydro-pyrano[3,4-b]indol-1-yl)-acetic acid as the carboxylic acid component afforded the title compound as a solid. $^1$H NMR (500 MHz, CDCl$_3$) δ 7.51 (br, 1H), 7.15 (s, 1H), 6.83 (s, 1H), 4.06 (m, 1H), 3.98 (m, 1H), 3.67 (m, 2H), 2.85 (m, 1H), 2.72 (dt, 1H), 2.69 (br, 1H), 2.43 (s, 3H), 2.42 (s, 3H), 2.20 (m, 1H), 2.06 (m, 1H), 2.03 (m, 1H), 1.89 (m, 1H), 0.95 (t, 3H); 2.43 (+) MS m/e=274 (MH$^+$), ESI (−) MS m/e=272 (MH$^-$).

COMPOUND 46: 2-(6,8-DICHLORO-1-ETHYL-1,3,4,9-TETRAHYDRO-PYRANO[3,4-B]INDOL-1-YL)-ETHANOL

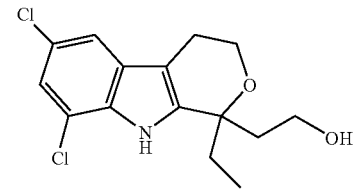

46.A. Synthesis of 5,7-Dichloro-1H-indole

Following the procedure of example 45.A. except using 5,7-dichloro-1H-indole-2,3-dione as the dione component afforded the title compound as a oil.

46.B. Syntehsis of (5,7-Dichloro-1H-indol-3-yl)-oxo-acetic acid ethyl ester

Following the procedure of example 36.C. except using 5,7-dichloro-1H-indole as the indole component afforded the title compound as a solid.

46.C. Synthesis of (6,8-Dichloro-1-ethyl-1,3,4,9-tetrahydro-pyrano[3,4-b]indol-1-yl)-acetic acid ethyl ester Following the procedure of example 36.D. except using (5,7-dichloro-1H-indol-3-yl)-oxo-acetic acid ethyl ester component afforded the title compound as an oil.

46.D. Synthesis of (6,8-Dichloro-1-ethyl-1,3,4,9-tetrahydro-pyrano[3,4-b]indol-1-yl)-acetic acid Following the procedure of example 22.B. except using (6,8-dichloro-1-ethyl-1,3,4,9-tetrahydro-pyrano[3,4-b]indol-1-yl)-acetic acid ethyl ester as the ester component afforded the title compound as a solid. $^1$H NMR (500 MHz, CDCl$_3$) δ 9.07 (br, 1H), 7.03 (d, 1H), 6.97 (d, 1H), 4.07 (m, 1H), 4.01 (m, 1H), 3.15 (t, 2H), 3.10 (d, 1H), 3.03 (d, 1H), 2.15 (m, 1H), 2.05 (m, 1H), 0.88 (t, 3H); ESI (+) MS m/e=328 (MH$^+$), ESI (−) MS m/e=326 (MH$^-$).

46.E. Synthesis of 2-(6,8-Dichloro-1-ethyl-1,3,4,9-tetrahydro-pyrano[3,4-b]indol-1-yl)-ethanol Following the procedure of example 22.C. except using (6,8-dichloro-1-ethyl-1,3,4,9-tetrahydro-pyrano[3,4-b]indol-1-yl)-acetic acid as the carboxylic acid component afforded the title compound as a solid. $^1$H NMR (500 MHz, CDCl$_3$) δ 8.25 (br, 1H), 7.03 (d, 1H), 6.98 (d, 1H), 4.03 (m, 1H), 3.99 (m, 1H), 3.71 (m, 2H), 3.13 (m, 2H), 2.57 (br, 1H), 2.23 (m, 1H), 2.07 (m, 1H), 2.04 (m, 1H), 1.92 (m, 1H), 0.93 (t, 3H); ESI (+) MS m/e=314 (MH$^+$), ESI (−) MS m/e=312 (MH$^-$).

COMPOUND 47: 2-(6-BROMO-1,8-DIETHYL-1,3,4,9-TETRAHYDRO-PYRANO[3,4-B]INDOL-1-YL)-ETHANOL

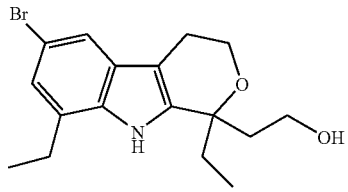

47.A. Synthesis of N-(4-Bromo-2-ethyl-phenyl)-2-hydroxyimino-acetamide

Following the procedure of example 36.A. except using 4-bromo-2-ethylaniline as the aniline component afforded the title compound as a solid. ESI (−) MS m/e=269 (MH−).

47.B. Synthesis of 5-Bromo-7-ethyl-1H-indole-2,3-dione

Following the procedure of example 36.B. except using N-(4-Bromo-2-ethyl-phenyl)-2-hydroxyimino-acetamide as the acetamide component afforded the title compound as a solid. ESI (−) MS m/e=252 (MH−).

47.C. Synthesis of (5-Bromo-7-ethyl-1H-indol-3-yl)-oxo-acetic acid ethyl ester

Following the procedure of example 36.C. except using 5-Bromo-7-ethyl-1H-indole-2,3-dione as the dione component afforded the title compound as a solid. ESI (+) MS m/e=324 (MH+), ESI (−) MS m/e=322 (MH−).

47.D. Synthesis of (6-Bromo-1,8-diethyl-1,3,4,9-tetrahydro-pyrano[3,4-b]indol-1-yl)-acetic acid ethyl ester Following the procedure of example 36.D. except using (5-bromo-7-ethyl-1H-indol-3-yl)-oxo-acetic acid ethyl ester as the ester component afforded the title compound as a solid.

47.E. Synthesis of 2-(6-Bromo-1,8-diethyl-1,3,4,9-tetrahydro-pyrano[3,4-b]indol-1-yl)-ethanol Following the procedure of example 28.C. except using (6-bromo-1,8-diethyl-1,3,4,9-tetrahydro-pyrano[3,4-b]indol-1-yl)-acetic acid ethyl ester as the ester component afforded the title compound as a solid. ¹H NMR (500 MHz, CDCl₃) δ 7.89 (br, 1H), 7.48 (d, 1H), 7.11 (d, 1H), 4.05 (m, 1H), 3.99 (m, 1H), 3.70 (m, 2H), 2.80 (m, 3H), 2.71 (dt, 1H), 2.55 (br, t, 1H), 2.19 (m, 1H), 2.05 (m, 1H), 2.01 (m, 1H), 1.90 (m, 1H), 1.33 (t, 3H), 0.92 (t, 3H); ESI (+) MS m/e=352 (MH+), ESI (−) MS m/e=350 (MH−).

COMPOUND 48: 2-(1,8-DIETHYL-1,3,4,9-TETRAHYDRO-PYRANO[3,4-7B]INDOL-1-YL)-N,N-DIMETHYL-ACETAMIDE

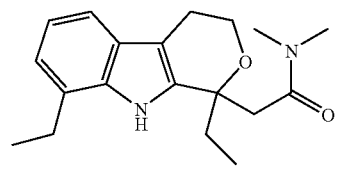

2-(1,8-Diethyl-1,3,4,9-tetrahydro-pyrano[3,4-b]indol-1-yl)-N,N-dimethyl-acetamide. Following the procedure of example 27 except using dimethylamine as the amine component afforded the title compound as a solid. ¹H NMR (500 MHz, CDCl₃) δ 9.39 (br, 1H), 7.35 (d, 1H), 7.05 (t, 1H), 6.99 (d, 1H), 6.19 (m, 1H), 4.06 (m, 1H), 3.98 (m, 1H), 2.84 (s, m, 9H), 2.11 (m, 1H), 2.01 (m, 1H), 1.36 (t, 3H), 0.85 (t, 3H); ESI (−) MS m/e=299 (MH−).

COMPOUND 49: 2-(9-BENZYL-1,8-DIETHYL-1,3,4,9-TETRAHYDRO-PYRANO[3,4-B]INDOL-1-YL)-ETHANOL

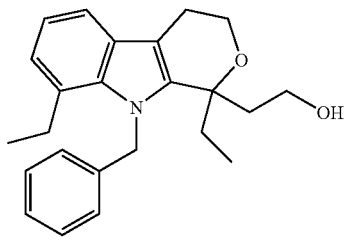

Compound 49 was synthesized according to the following scheme:

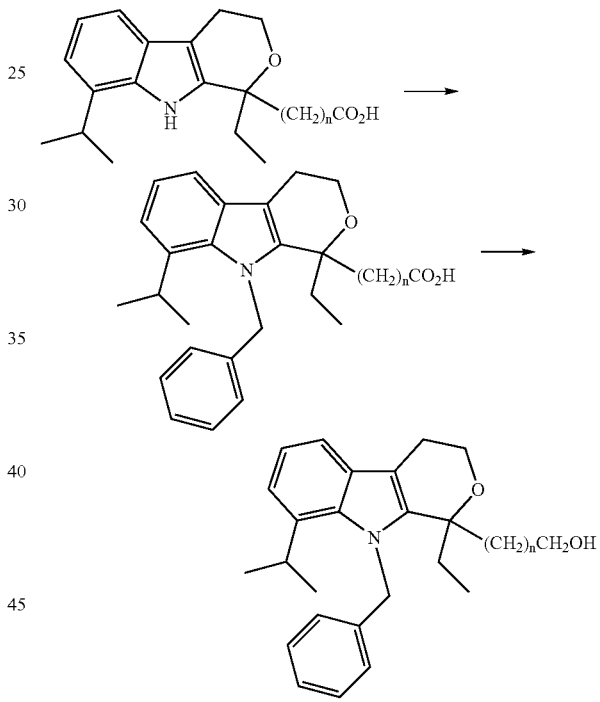

49.A. Synthesis of (9-Benzyl-1,8-diethyl-1,3,4,9-tetrahydro-pyrano[3,4-b]indol-1-yl)-acetic acid To a solution of (1,8-diethyl-1,3,4,9-tetrahydro-pyrano[3,4-b]indol-1-yl)-acetic acid (0.51 g, 1.8 mmol) in tetrahydrofuran at room temperature was added sodium hydride (60% dispersion in mineral oil, 0.4 g). After being heated at 50° C. for 2 hours, benzyl bromide (0.6 g, 3.5 mmol) was added and the solution was stirred for another 2 hours. It was quenched with ethyl acetate and washed with water. The ethyl acetate layer was dried over magnesium sulfate and evaporated to dryness. Flash chromatography on silica gel provided 0.486 g (73%) of the title compound as a solid. ¹H NMR (500 MHz, CDCl₃) δ 7.13 (m, 3H), 6.97 (d, 1H), 6.74 (d, 1H), 6.68 (t, 1H), 6.21 (d, 1H), 3.90 (s, 1H), 3.63 (m, 1H), 3.35 (td, 1H), 3.18 (d, 1H), 3.00 (d, 1H), 2.67 (q, 2H), 2.44 (q, 2H), 2.10 (m, 1H), 1.85 (d, 1H), 1.52 (m, 1H), 1.41 (m, 1H), 1.16 (t, 3H), 0.75 (t, 3H); ESI (+) MS m/e=278 (MH+).

49.B. Synthesis of 2-(9-Benzyl-1,8-diethyl-1,3,4,9-tetrahydro-pyrano[3,4-b]indol-1-yl)-ethanol To a solution of (9-benzyl-1,8-diethyl-1,3,4,9-tetrahydropyrano[3,4-b]indol-1-yl)-acetic acid (0.45 g, 1.2 mmol) in tetrahydrofuran at room temperature was added 1.0 M solution of borane-tetrahydrofuran complex in tetrahydrofuran and it was stirred at 90° C. for 4 hours. The mixture was quenched with 5% HCl solution and stirred at room temperature for 20 minutes. It was extracted with ethyl acetate and washed with saturated sodium bicarbonate. The extracts were dried over magnesium sulfate and evaporated to dryness. Flash chromatography on silica gel provided 0.321 g (74%) of the title compound as a solid. $^1$H NMR (500 MHz, CDCl$_3$) δ 7.17 (m, 3H), 6.94 (d, 1H), 6.84 (m, 2H), 6.70 (t, 1H), 6.56 (d, 1H), 3.87 (m, 1H), 3.79 (m, 1H), 3.68 (dt, 1H), 3.64 (br, 1H), 3.41 (td, 1H), 2.93 (q, 2H), 2.43 (q, 2H), 2.04 (m, 1H), 1.93 (dt, 1H), 1.86 (m, 1H), 1.77 (m, 1H), 1.49 (m, 1H), 1.38 (m, 1H), 1.17 (t, 3H), 0.70 (t, 3H)

COMPOUND 50: 2-(1,8-DIETHYL-9-METHYL-1,3,4,9-TETRAHYDRO-PYRANO[3,4-B]INDOL-1-YL)-ETHANOL

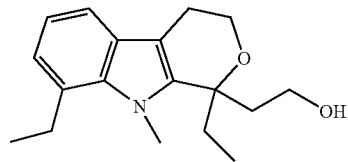

50.A. Synthesis of 2-(1,8-Diethyl-9-methyl-1,3,4,9-tetrahydro-pyrano[3,4-b]indol-1-yl)-acetic acid Following the procedure of example 49.A. except using (1,8-Diethyl-1,3,4,9-tetrahydro-pyrano[3,4-b]indol-1-yl)-acetic acid as the indole component afforded the title compound as an oil.

50.B. Synthesis of 2-(1,8-Diethyl-9-methyl-1,3,4,9-tetrahydro-pyrano[3,4-b]indol-1-yl)-ethanol Following the procedure of example 49.B. except using 2-(1,8-diethyl-9-methyl-1,3,4,9-tetrahydro-pyrano[3,4-b]indol-1-yl)-acetic acid as the carboxylic acid component afforded the title compound as a solid. $^1$H NMR (500 MHz, CDCl$_3$) δ 7.35 (dd, 1H), 7.03 (t, 1H), 6.98 (d, 1H), 4.04 (m, 1H), 3.93 (m, 1H), 3.91 (s, 3H), 3.75 (m, 1H), 3.63 (m, 1H), 3.11 (q, 2H), 2.87 (m, 1H), 2.76 (dt, 1H), 2.68 (br, 1H), 2.27 (m, 1H), 2.22 (m, 1H), 2.12 (m, 1H), 1.97 (m, 1H), 1.35 (t, 3H), 0.94 (t, 3H); ESI (+) MS m/e=288 (MH$^+$).

COMPOUND 51: 2-(7-BROMO-1,8-DIETHYL-1,3,4,9-TETRAHYDROPYRANO[3,4-B]INDOL-1-YL)ETHANOL

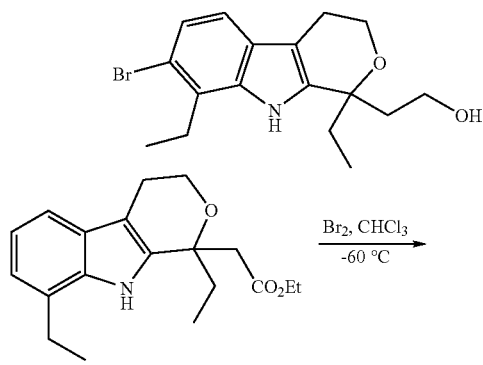

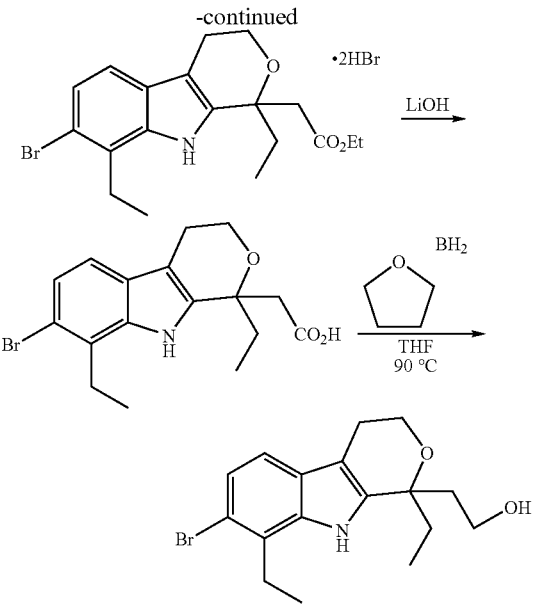

51.A. Synthesis of Ethyl 2-(7-bromo-1,8-diethyl-1,3,4,;9-tetrahydropyrano[3,4-b]indol-1-yl)acetate (R,S)-Etodolac ethyl ester (5 g, 15.8 mmol) was dissolved in chloroform (50 ml) and cooled to -60° C. with a dry ice/acetone bath. To this solution was added dropwise a solution of bromine (2.53 g, 15.8 mmol) in chloroform (50 ml) during 2 hr. After the addition, the reaction mixture was allowed to warm to -20° C. and triethylamine (5 ml) was added dropwise followed by silica gel (~20 g). The mixture was stirred for 10 min, filtered through silica gel (~10 g), and the filtrate evaporated to dryness. The crude product was recrystallized in hexane/dichloromethane (60 ml/20 ml) to give (4.5 g g, 72%) of product. $^1$H NMR (300 MHz, CDCl$_3$) δ 9.23 (b, NH), 7.45 (d, 1H), 7.15 (d, 1H), 4.21 (qrt, 2H), 4.15 (m, 1H), 3.95 (m, 1H), 3.25 (dd, 2H), 2.94 (m, 2H), 2.25 (m, 1H), 2.1 (m, 1H), 1.45 (t, 3H), 1.15 (t, 3H), 0.85 (t, 3H).

51.B. Synthesis of 2-(7-Bromo-1,8-diethyl-1,3,4,9-tetrahydropyrano[3,4-b]indol-1-yl)acetic acid To a stirred solution of ethyl 2-(7-bromo-1,8-diethyl-1,3,4,9-tetrahydropyrano[3,4-b]indol-1-yl)acetate (2.8 g, 5 mmol) in dioxane (40 ml) was added lithium hydroxide monohydrate (2.8 g, 67 mmol) and water (30 ml). The mixture was stirred at room temperature overnight. It was concentrated under reduced pressure, neutralized with 5% HCl, extracted with CH$_2$Cl$_2$, dried over MgSO$_4$, and concentrated. The crude product was recrystallized in dichloromethane/hexane (60 ml/20 ml) to give a white solid (980 mg, 53%). $^1$H NMR (300 MHz, CDCl$_3$) δ 8.68 (br, NH)), 7.27 (d, 1H), 7.19 (d, 1H), 4.06 (m, 2H), 3.04 (qrt, 2H), 2.95 (qrt, 2H), 2.80 (m, 2H), 2.09 (m, 2H), 1.24 (t, 3H), 0.874 (t, 3H).

51.C. Synthesis of 2-(7-Bromo-1,8-diethyl-1,3,4,9-tetrahydropyrano[3,4-b]indol-1-yl)ethanol To a stirred solution of 2-(7-Bromo-1,8-diethyl-1,3,4,9-tetrahydropyrano[3,4-b]indol-1-yl)acetic acid (0.87 g, 2.4 mmol) in THF (5 ml), was added dropwise via syringe borane-tetrahydrofuran complex, 1.0 M solution in tetrahydrofuran (3.6 ml, 3.6 mmol) during 30 min. The mixture was stirred at 90° C. for 8 hr, cooled, quenched with distilled water and 5% HCl, extracted with EtOAc. The organic phases collected, washed with brine, dried over MgSO$_4$, and evaporated to give a residue which was chromatographed on silica gel. Elution with hexane-EtOAc (1:1) gave the product which was further recrystallized in hexane/dichloromethane to give the product (0.64 g, 76%). $^1$H NMR (300 MHz, CDCl$_3$) δ 7.91 (b, NH), 7.28 (d, 1H), 7.20 (d, 1H), 4.02 (m, 2H), 3.71 (m, 2H), 2.95 (qrt, 1H), 2.81 (m, 1H), 2.75 (t, 1H), 2.69 (t, 1H), 2.58 (t, 1H), 2.19 (m, 1H), 2.04 (m, 2H), 1.26(t, 3H), 0.93 (t, 3H).

COMPOUND 54: 2-(6-BROMO-1-ETHYL-1,3,4,9-TETRAHYDRO-8-ISOPROPYLPYRANO[3,4-B]INDOL-1-YL)ETHANOL

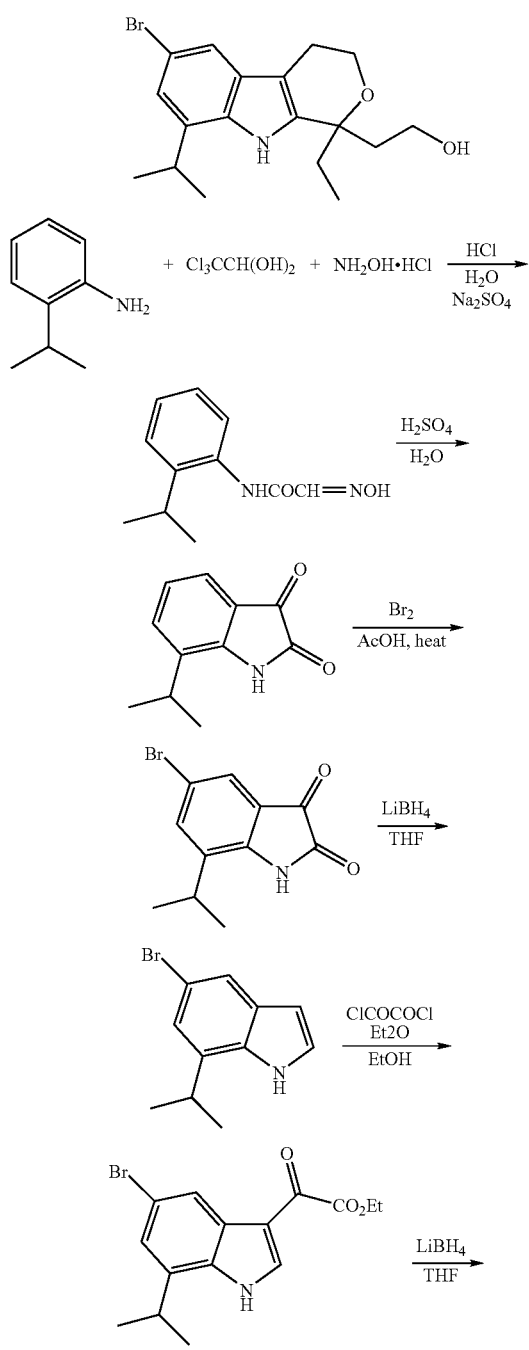

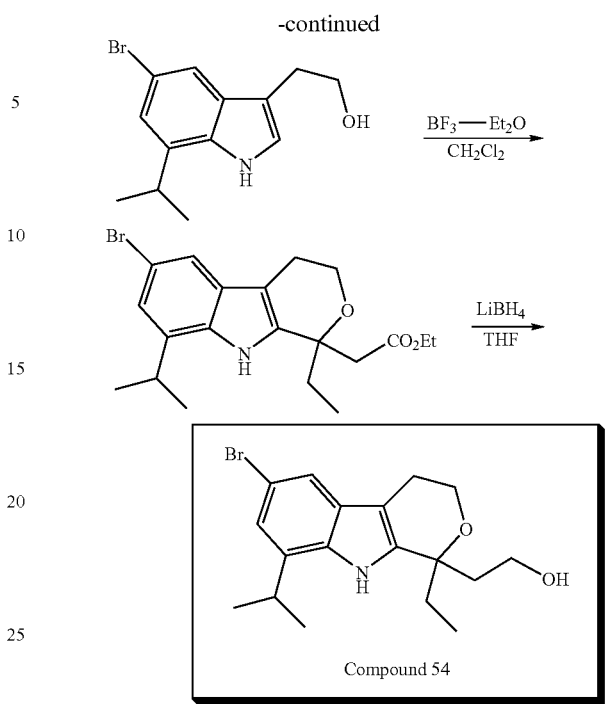

Compound 54

54.A. Synthesis of 2-(Hydroxyimino)-N-(2-isopropylphenyl)acetamide

In a 2-1 round-bottomed flask are placed water (1000 ml), followed by chloral hydrate (49 g, 0.30 mol), anhydrous sodium sulfate (225 g), 2-isopropylaniline (50 g, 0.37 mol), concentrated hydrochloric acid (22 ml, 0.26 mol), hydroxylamine hydrochloride (57 g, 0.81 mol). The solution was boiled for 3 hr, cooled, quenched with water, and extracted with ethyl acetate. The extracts were dried over MgSO$_4$, and evaporated. The residue was purified by elution from a silica gel column with hexane/EtOAc (7:3) to afford the product (26.7 g, 35%). $^1$H NMR (300 MHz, CDCl$_3$) δ 8.28 (br, NH), 7.88 (dd, 1H), 7.82 (b, NOH), 7.63 (s, N=CH), 7.24 (m, 3H), 3.04 (m, 1H), 1.27 (d, 6H); ESI (+) MS m/e=207 (MH$^+$), ESI (−) MS m/e=205 (MH$^-$).

54.B. Synthesis of 7-Isopropylindoline-2,3-dione

To a stirred solution of concentrated H$_2$SO4 (210 ml) and H2O (50 ml), was added over 20 min (26.7 g, 0.13 mol) of 2-(hydroxyimino)-N-(2-isopropylphenyl)acetamide. The mixture was stirred at 75° C. for 2 hr, cooled and poured onto cracked ice. After standing for 15 min, it was extracted with EtOAc, washed with water, dried over MgSO4, and concentrated. Air drying afforded (23.8 g, 97%) of crude product). $^1$H NMR (300 MHz, CDCl$_3$) δ 8.15 (b, NH), 7.49 (d, 2H), 7.11 (t, 1H), 2.87(m, 1H), 1.30 (d, 6H); ESI (+) MS m/e=190 (MH+), ESI (−) MS m/e=188 (MH−).

54.C. Synthesis of 5-Bromo-7-isopropylindoline-2,3-dione 7-isopropylindoline-2,3-dione (23.8 g, 0.12 mol) was added to a stirred solution of glacial acetic acid (700 ml). To this solution was added, via additional funnel bromine (7.8 ml, 0.15 mol) in glacial acetic acid (300 ml) during 30 min. After the addition, the combined mixture was stirred at 75° C. for 3 hr, cooled, and extracted with EtOAc. The organic extracts were washed with brine, dried over MgSO$_4$, and evaporated in vacuo; air dried to give (31.8 g, 94%) of crude product. $^1$H NMR (300 MHz, CDCl$_3$) δ 8.04 (b, NH), 7.59

(dd 2H), 2.84 (m, 1H), 1.31 (d, 6H); ESI (+) MS m/e=269 (MH+), ESI (−) MS m/e=267(MH−).

54.D. Synthesis of 5-Bromo-7-isopropyl-1H-indole

To a stirred solution of 5-bromo-7-isopropylindoline-2,3-dione (45.1 g, 0.17 mol) in THF (275 ml) at room temperature under a nitrogen atmosphere, was added, via syringe, 2.0 M solution of LiBH$_4$/THF (215 ml) over 30 min. The reaction mixture was stirred at 90° C. for 1 hr, cooled, quenched with distilled water and 5% HCl, and extracted with EtOAc. The extracts were washed with brine, dried over MgSO$_4$, and concentrated under reduced pressure. The crude product was purified by elution from a silica gel column with hexane/EtOAc (9:1) to give (14.5 g, 36%) of the product. $^1$H NMR (300 MHz, CDCl$_3$) δ 8.18 (b, NH), 7.62 (d, 1H), 7.21 (t, 1H), 7.16 (d, 1H), 6.51 (dd, 1H), 3.20 (m, 1H), 1.38 (d, 6H); ESI (+) MS m/e=239 (MH+), ESI (−) MS m/e=237 (MH−).

54.E. Synthesis of Ethyl 2-(5-Bromo-7-isopropyl-1H-indol-3-yl)-2-oxoacetate

A 2.0 M solution of oxalyl dichloride in dichloromethane (60 ml, 0.12mol) was added dropwise during 10 min to a solution of 5-Bromo-7-isopropyl-1H-indole (14.5 g, 0.061 mol) in Et$_2$O (220 ml) at room temperature under a nitrogen atmosphere. The mixture was stirred for 4.5 hr. The Et$_2$O was removed by evaporation and absolute EtOH (220 ml) was added. The resulting mixture was stirred at room temperature under a nitrogen atmosphere overnight. The EtOH was evaporated, and EtOAc was added to the residue and washed with sat. NaHCO$_3$ and brine. The organic layers were dried over MgSO$_4$, concentrated, and dried under vaccume to give a crude product (13.8 g, 67%). $^1$H NMR (300 MHz, CDCl$_3$) δ 8.85 (b, NH), 8.46 (dd, 2H), 7.33 (d, 1H), 4.42 (qrt, 2H), 3.21 (m, 1H), 1.44 (t, 3 H), 1.38 (d, 6H), ESI (+) MS m/e=339 (MH+), ESI (−) MS m/e=337 (MH−).

54.F. Synthesis of 2-(5-Bromo-7-isopropyl-1H-indol-3-yl)ethanol. Ethyl 2-(5 -bromo-7-isopropyl-1H-indol-3-yl)-2-oxoacetate(13.8 g, 0.04mol) in THF (300 ml) was reduced with 2.0 M solution of LiBH$_4$ in THF (50 ml, 0.1 mol) by refluxing under nitrogen atmosphere for 5 hr, cooled, quenched with distilled water and 5% HCl, and extracted with EtOAc. The extracts were washed with brine, dried over MgSO$_4$, and concentrated. The crude product was purified by eluting from silica gel with hexane/EtOAc to obtain (4.5 g, 39%) of product. $^1$H NMR (300 MHz, CDCl$_3$) δ 8.05 (b, NH), 7.59 (d, 1H), 7.17 (d, 1H), 7.10 (d, 1H), 3.89 (t, 2H), 3.18 (m, 1H), 2.98 (t, 2 H), 1.37 (d, 6H); ESI (+) MS m/e=283 (MH+), ESI (−) MS m/e=281 (MH−).

54.G. Synthesis of Ethyl 2-(6-Bromo-1-ethyl-1,3,4,9-tetrahydro-8-isopropylpyrano[3,4-b]indol-1-yl)acetate To a suspension of 2-(5-bromo-7-isopropyl-1H-indol-3-yl)ethanol (4.5 g, 0.016 mol) under nitrogen atmosphere was added boron trifluoride diethyl etherate (2.2 ml, 0.18 mol), followed by dropwise addition of ethyl propionyl acetate (3.4 ml, 0.024 mol) over ten minutes. The mixture was stirred at room temperature for 1.5 hr. Dichloromethane was added to the mixture and the organic layer was washed with sat. NaHCO$_3$ and water, and dried over MgSO$_4$. The solvent was concentrated and air dried to give a crude product (6 g, 92%). ESI (+) MS m/e=409 (MH+), ESI (−) MS m/e=407 (MH−).

54.F. Synthesis of 2-(6-Bromo-1-ethyl-1,3,4,9-tetrahydro-8-isopropylpyrano[3,4-b]indol-1-yl)ethanol To a stirred solution of ethyl 2-(6-bromo-1-ethyl-1,3,4,9-tetrahydro-8-isopropylpyrano[3,4-b]indol-1-yl)acetate (6.0 g, 0.015 mol) in THF (120 ml), was added 2.0 M solution of LiBH$_4$/THF (20 ml, 0.30 mol) via syringe during 30min under a nitrogen atmosphere at room temperature. The mixture was refluxed for 10 hr, cooled, quenched with water and 5% HCl, and extracted with EtOAc. The organic phases were combined and washed with brine, dried over MgSO$_4$, and evaporated to give a residue, which was chromatographed on silica gel. Elution with hexane-EtOAc (7:3) gave the product (4.3 g, 80%). $^1$H NMR (300 MHz, CDCl$_3$) δ 8.18 (b, NH), 0.92 (t, 3H), 1.35 (d, 6H), 1.98 (m, 3H), 2.19 (m, 1H), 2.54 (t, 1H), 2.75 (m, 2H), 3.17 (m, 1H), 3.71 (t, 1H), 4.03(m, 2H), 7.13 (dd, 1H), 7.45 (d, 1H), 7.96 (b, NH). ESI (+) MS m/e=367 (MH+), ESI (−) MS m/e=365 (MH−).

COMPOUND 55: ETHYL 3-(1-ETHYL-1,3,4,9-TETRAHYDRO-1-(2-HYDROXYETHYL)-8-ISOPROPYLPYRANO[3,4-B]INDOL-6-YL)PROPANOATE

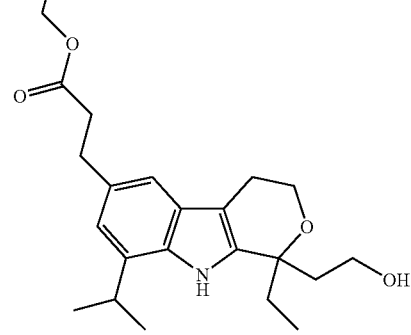

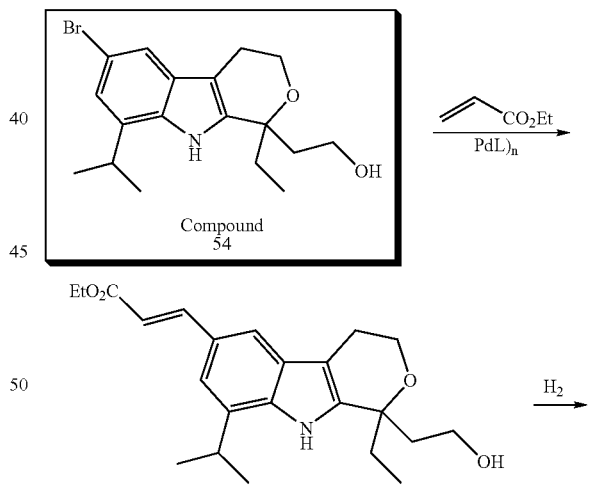

Compound 54

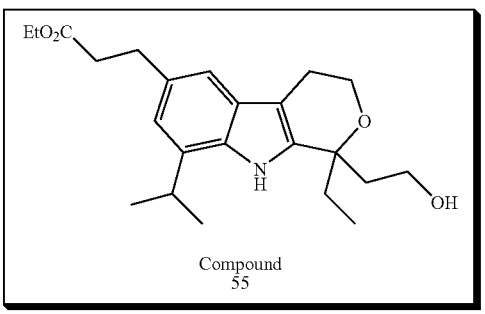

Compound 55

55.A. Synthesis of (E)-ethyl 3-(1-Ethyl-1,3,4,9-tetrahydro-1-(2-hydroxyethyl)-8-isopropylpyrano[3,4-b]indol-6-yl)acrylate A suspension of Pd(OAc)$_2$ (0.2 g, 0.8 Mmol), P(o-tolyl)$_3$ (0.25 g, 0.8 mmol), 2-(6-bromo-1-ethyl-1,3,4,9-tetrahydro-8-isopropylpyrano[3,4-b]indol-1-yl)ethanol (1.5 g, 4.1 mmol), triethylamine (1.5 ml, 11 mmol), and ethyl acrylate (1.8 ml, 16 mmol) in acetonitrile (45 ml) and stirred under a nitrogen atmosphere at 100° C. for 24 hr. The mixture was allowed to cool, quenched with water, worked-up with dichloromethane, and washed with brine. The organic layers were dried over MgSO$_4$ and concentrated under reduced pressure. The crude product was chromatographed on silica hexane/EtOAc (6:4) to give the product (0.9 g, 56%). %). $^1$H NMR (300 MHz, CDCl$_3$) δ 8.07 (br, NH), 7.83 (d, 1H), 7.53 (d, 1H), 7.28 (d, 1H), 6.43 (d, 1H), 4.27 (m, 2H), 4.04 (m, 2H), 3.73 (m, 2H), 3.19 (m, 1H), 2.84 (m, 1), 2.77 (d, 1H), 2.52 (br, 1H), 2.20 (m, 1H), 2.09 (m, 1H), 1.92 (m, 1H), 1.38 (d, 6H), 1.35 (t, 3H), 0.95 (t, 3H); ESI (+) MS m/e=386 (MH$^+$), ESI (−) MS m/e=384 (MH$^−$).

55.B. Synthesis of Ethyl 3-(1-Ethyl-1,3,4,9-tetrahydro-1-(2-hydroxyethyl)-8-isopropylpyrano[3,4-b]indol-6-yl)propanoate To a suspension of (E)-ethyl 3-(1-ethyl-1,3,4,9-tetrahydro-1-(2-hydroxyethyl)-8-isopropylpyrano[3,4-b]indol-6-yl)acrylate (0.8 g, 2.3 mmol) in 2% HCl in EtOH (80 ml) was added palladium on carbon (10%, 0.5 g). The mixture was stirred under an atmoshphere of hydrogen (1 am) at room temperature for 24 hr. The catalyst filtered through celite. The filtrate was evaporated at reduced pressure. The residue was neutralized with sat. NaHCO$_3$, extracted with EtOAc, and dried over MgSO$_4$. The solvent was concentrated under reduced pressure and purified by silica gel flash column chromatography hexane/EtOAc (6:4) to give the product (0.33 g, 38%). $^1$H NMR (300 MHz, CDCl$_3$) δ 7.72 (br, NH), 7.18 (d, 1H), 6.91 (d, 1H), 4.15 (qrt, 2H), 4.02 (m, 2H), 3.70 (m, 2H), 3.17 (m, 1H), 3.04 (t, 2H), 2.83 (m, 1H), 2.68 (m, 3H), 2.18 (m, 1H), 2.05 (m, 1H), 1.96 (m, 2H), 1.36 (d, 6H), 1.26 (t, 3H), 0.94 (t, 3H); ESI (+) MS m/e=388 (MH$^+$), ESI (−) MS m/e=386 (MH$^−$).

COMPOUND 56: 3-(1-ETHYL-1,3,4,9-TETRAHYDRO-1-(2-HYDROXYETHYL)-8-ISOPROPYLPYRANO[3,4-B]INDOL-6-YL)PROPANOIC ACID

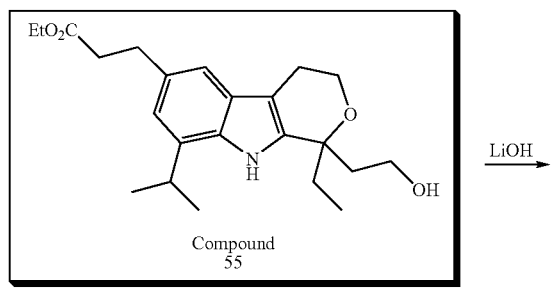

Compound 55

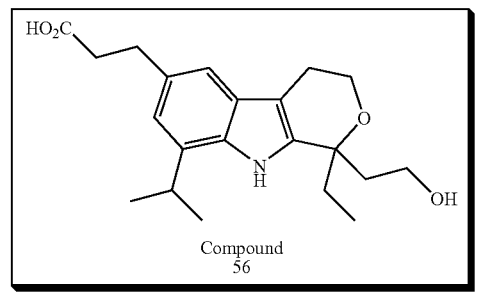

Compound 56

56.A. Synthesis of 3-(1-Ethyl-1,3,4,9-tetrahydro-1-(2-hydroxyethyl)-8-isopropylpyrano[3,4-b]indol-6-yl)propanoic Acid To a stirred solution of ethyl 3-(1-ethyl-1,3,4,9-tetrahydro-1-(2-hydroxyethyl)-8-isopropylpyrano[3,4-b]indol-6-yl)propanoate (0.28 g, 0.72 mmol) in dioxane (6 ml) was added lithium hydroxide monohydrate (0.18 g, 4.3 mmol) and water (3 ml). The mixture was stirred at room temperature for 8 hr. It was concentrated under reduced pressure, neutralized with 5% HCl, extracted with EtOAc, and dried over MgSO$_4$. The solvent concentrated and purified by silica gel flash column chromatography dichloromethane/methanol (8:2) to give the product (0.09 g, 35%). $^1$H NMR (300 MHz, CDCl$_3$) δ 7.77 (br, NH)), 7.19 (d, 1H), 6.91 (d, 1H), 4.04 (m, 2H), 3.68 (m, 2H), 3.16 (m, 1H), 3.06 (t, 2H), 2.85 (m, 1H), 2.74 (m, 3H), 2.18 (m, 1H), 1.98 (m, 3H), 1.35 (d, 6H), 0.94 (t, 3H); ESI (+) MS m/e=360 (MH$^+$), ESI (−) MS m/e=358 (MH$^−$).

COMPOUND 57: 3-(1-ETHYL-1,3,4,9-TETRAHYDRO-1-(2-HYDROXYETHYL)-8-ISOPROPYLPYRANO[3,4-B]INDOL-6-YL)PROPAN-1-OL

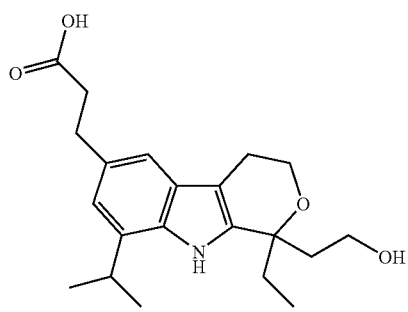

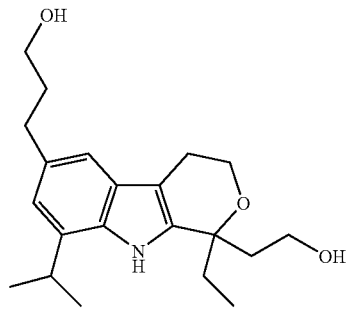

-continued

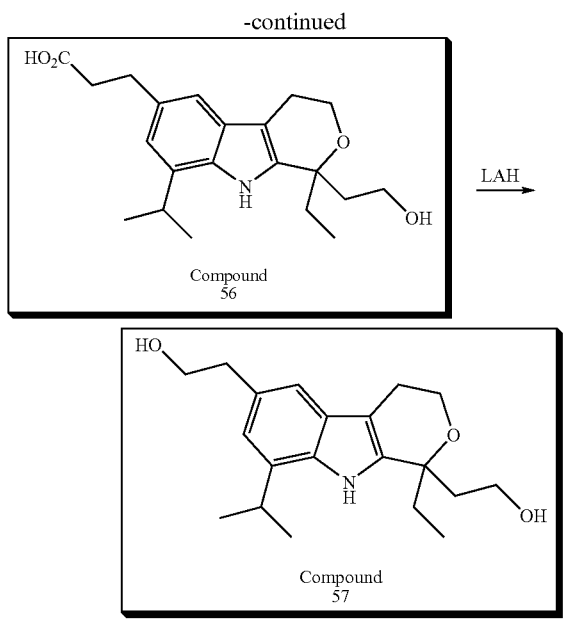

Compound 56

Compound 57

57.A. Synthesis of 3-(1-ethyl-1,3,4,9-tetrahydro-1-(2-hydroxyethyl)-8-isopropylpyrano[3,4-b]indol-6-yl)propan-1-ol A solution of ethyl 3-(1-ethyl-1,3,4,9-tetrahydro-1-(2-hydroxyethyl)-8-isopropylpyrano[3,4-b]indol-6-yl)propanoate (0.18 g, 0.46 mmol) in anhydrous diethyl ether (15 ml) was stirred at room temperature under a nitrogen atmosphere. LiAlH$_4$ (0.09 g, 2.4 mmol) was slowly added to the solution. The mixture was stirred for 18 hr, quenched with water and 5% HCl, extracted with EtOAc, dried over MgSO4, and concentrated under reduced pressure. The crude product was purified by silica gel flash column chromatography hexane/EtOAc (4:6) twice to give (31 mg) of the product (0.031 g, 20%). 1H NMR (300 MHz, CDCl3) δ 7.70 (br, NH), 7.18 (d, 1H), 6.91 (d, 1H), 4.03 (m, 2H), 3.73 (m, 4H), 3.17 (m, 1H), 2.80 (m, 6H), 2.18 (m, 1H), 1.98 (m, 3H), 1.37 (d, 6H), 1.26 (br, 1H), 0.94 (t, 3H); ESI (+) MS m/e=346 (MH$^+$), ESI (−) MS m/e=344 (MH$^−$).

Example 2

Biological Data

Cox-1

Test compound and/or vehicle is incubated with human platelets (10$^8$/ml) containing the phospholipase inhibitor MLnFP (100 μM) for 15 minutes at 37° C. Arachidonic acid (100 μM) is then added for a further 15 minute incubation period. The reaction is stopped by addition of 1 N HCl and neutralized with IN NaOH. PGE$_2$ levels in the supernatant are determined using the Amersham EIA kit. Compounds are screened at 10 μM. Cox assays are described in Chan et al. 1999 *J Pharmacol Exp Ther*. 290:551-560; and Swinney et al. 1997, *J Biol Chem*. 272:12393-12398; both incorporated herein by reference.

Cox-2

Cyclooxygenase-2 (human recombinant, expressed in Sf9 cell, Cayman 60122) is used. Test compound and/or vehicle is pre-incubated with 0.11 U cyclooxygenase-2, 1 mM reduced glutathione (GSH), 500 μM phenol and 1 μM hematin for 15 minutes at 37° C. The reaction is initiated by addition of 0.3 μM arachidonic acid as substrate in Tris-HCl pH 7.7 and terminated after a 5 minute incubation at 37° C. by addition of 1N HCl. Following centrifugation, substrate conversion to PGE$_2$ is measured by an Amersham EIA kit. Compounds are screened at 10 μM. COX-2 assays are described in Riendeau, D., et al., 1997 *Can. J Physiol. Pharmacol*. 75:1088-1095; and Warner, J. D., et al., 1999 *Proc. Natl. Acad. Sci.* U.S.A. 96: 7563-7568; both incorporated herein by reference.

Provided below in Table I are exemplary results for COX-1 and COX-2 inhibition by compounds described herein:

TABLE I

| Compound No. | COX-1 (IC50 μM) | COX-1 % Inhibition | COX-2 (IC50 μM) | COX-2 % Inhibition |
|---|---|---|---|---|
| Etodolac | >300 | −25 | >300 | −14 |
| 1 | <10 | 96 | <10 | 100 |
| 7 | | 94 | | 99 |
| 9 | | 88 | | 90 |
| 27 | >300 | 24 | >300 | 3 |
| 35 | >300 | −69 | >300 | −10 |
| 36 | >300 | −4 | >300 | 18 |
| 47 | 68.6 | 45 | >100 | 78 |
| 52 | | 78 | | 97 |
| 53 | | 90 | | 96 |

Inhibition of β-Catenin

Inhibition of β-catenin was measured using a reporter assay based on the assay described in Korinek et al. 1997 *Science* 275:1784-1787 and employing the reporter plasmid TOPFLASH.

On Day 1, HEK-293 cells (ATCC) were plated in 24-well plates (VWR) at 40,000 cells per well in 450 μL DMEM+ 10× FBS media and incubated overnight at 37° C., 5% CO$_2$.

On Day 2, TOPFLASH plasmid (Upstate Cell Signaling Solutions, VA), pGL3 control vector (Promega), and a plasmid encoding for constitutively expressed human β-catenin (Hans Clevers) were separately diluted to 0.1 μg/μL in TE Buffer. Transfections were done using FuGene 6 Transfection Reagent (Roche). Transfection mixtures included either 8 μl of 0.1 μg/μl pGL3 in 400 μl serum free media (DMEM, Gibco) and 9.6 μl FuGene, or 8 μl of 0.1 g/μl TOPFLASH and 16 μl of 0.1 β-catenin plasmid in 400 μl serum free media (DMEM, Gibco) and 9.6 μl FuGene. The transfection mixtures were gently mixed and incubated for 15-30 min at room temperature. Fifty μl of the appropriate transfection mixture was added dropwise to the 293 cells and the cells incubated overnight at 37° C., 5% CO$_2$.

On Day 3, the compounds to be tested were diluted to 0.25M in dimethylsulfoxide (DMSO). This solution was then used to make a 3X dilution of compound into DMEM+ 10% FBS, e.g., 100 μm to 300 μm. Two-hundred and fifty μl of the 3× diluted compound was added drop-wise to an appropriate well containing 500 μl of media. This was swirled gently. After mixing, 250 μl of the diluted 3× compound was added to another well and the procedure followed until the compound was diluted down three times. Plates were incubated for 24 hrs at 37° C., 5% CO$_2$. Experiments were performed in duplicate.

On Day 4, Luciferase activity was measured using a Promega Steady-Glo® luciferase assay system (Promega Cat. No. EC251) according to the manufactures instructions. The cells and Glo Lysis buffer were equilibrated to room temperature. Ten mls of Glo Lysis® Buffer was added to reconstitute the Steady-Glo® Assay Reagent. Five hundred μl of the Glo Lysis Buffer®/Assay Reagent were added to each well. The reaction was incubated for 5 min on a shaker at room temperature. 100 μl of lysate was transferred to a white 96-well plate and read on a Tecan (Research Triangle Park, N.C.) GENios microplate reader, using the luminescence setting.

Inhibition of β-catenin:TOP flash by some compounds of the invention is shown in FIG. 1.

Cell Cytotoxicity

Normal prostate cells (PREC, Cambrex East Rutherford N.J.), prostate cancer cell line (LNCaP, ATCC), PBL (peripheral blood leukocytes—buffy coat San Diego Blood Bank), and primary CLL cells were incubated for one to two days in RPMI-1640 and 10% FBS (fetal bovine serum). They were plated in 96-well plates at 100,000 cells/well. Titrated concentrations of the compound to be tested were added to the culture medium. The cells were incubated three days at 37° C., 5% $CO_2$. Viability of the cells was assayed by standard MTT assay. Each drug concentration was done in duplicate. MTT assay: 10 μl of 12 mM 3,[4,5-dimethylthiazol-2-yl]-2,5-diphenyltetrazolium bromide (MTT) (Sigma) was added to each well. The cells were incubated at 37° C., 5% $CO_2$ for 4 hours. 100 μl 20% SDS, 0.015M HCl was added to each well and the cells were incubated overnight. The plates were read at absorbance 595 nM.

Cytotoxicty results are shown in Table II and Table III.

TABLE II

| Compound No. | LNCap IC50 (nm) | PREC IC50 (nm) |
|---|---|---|
| Etodolac | 122 | 416 |
| 1 | 14 | 53 |
| 7 | 12 | |
| 9 | 10 | |
| 22 | 163 | |
| 23 | 70 | |
| 24 | 80 | |
| 25 | 60 | |
| 26 | 95 | |
| 27 | 52 | 140 |
| 28 | 25 | |
| 29 | 80 | |
| 30 | 100 | |
| 31 | 37 | |
| 32 | 15 | |
| 33 | 132 | |
| 34 | 20 | |
| 35 | 68 | 220 |
| 36 | 30 | 160 |
| 37 | 60 | |
| 38 | 23 | |
| 39 | 46 | |
| 40 | 80 | |
| 41 | 51 | |

TABLE II-continued

| Compound No. | LNCap IC50 (nm) | PREC IC50 (nm) |
|---|---|---|
| 42 | 12 | |
| 43 | 77 | |
| 44 | 60 | |
| 45 | 8 | |
| 46 | 18 | |
| 47 | 9 | 14 |
| 48 | 60 | |
| 51 | 10 | |
| 52 | 9 | |
| 53 | 11 | |
| 54 | 7 | |
| 55 | 18 | |
| 56 | 235 | |
| 57 | 110 | |

TABLE III

| Compound No. | CLL IC50 (nm) | PBL IC50 (nm) |
|---|---|---|
| Etodolac | 200 | 350 |
| 1 | 72 | 76 |
| 27 | 52 | 150 |
| 31 | 244 | |
| 32 | 250 | |
| 33 | 98 | |
| 36 | 50 | 160 |
| 38 | | 73 |
| 35 | 100 | 140 |
| 39 | | 120 |
| 40 | 185 | |
| 41 | 110 | |
| 45 | | 90 |
| 46 | | 20 |
| 47 | 21 | 60 |
| 48 | 240 | |

Selected analogs were tested and compared in several tumor cell lines and their multidrug-resistant (MDR) sub-lines. The MDR cell lines used in these experiments have been extensively characterized in the literature and are resistant to several widely used anti-cancer drugs, such as doxorubicin, paclitaxel, etoposide, and others. As shown in Table IV, Table V and Table VI, the selected analogs were found to be about 10-20-fold more potent when compared to Etodolac. In addition, no appreciable loss of activity was observed in the multidrug resistant sub-lines, when compared to the parental cells.

TABLE IV

| Compound No. | Ovarian MES-SA (parental) | Ovarian MES-SA/Dx5 (resistant) | Breast MCF-7 (parental) | Breast MCF-7 (parental) | Leukemia HL-60 (parental) | Leukemia HL-60/ADR resistant |
|---|---|---|---|---|---|---|
| Etodolac | 700 | 430 | 625 | >1000 | 300 | 550 |
| 1 | 26 | 18 | 14 | 21 | 13 | 16 |
| 36 | 100 | 63 | 54 | 80 | 38 | 50 |
| 47 | 24 | 15 | 19 | 20 | 13 | 23 |

TABLE V

| Compound No. | Kidney HEK-293 | Lung A549 | Colon SW480 | Colon HCT 116 | Colon HT-29 | Prostate DU145 | Prostate PC3 | Prostate LNCap |
|---|---|---|---|---|---|---|---|---|
| Etodolac | 900 | 800 | 355 | 195 | 750 | 266 | 240 | 93 |
| 1 | 23 | 10 | 23 | 17 | 30 | 48 | 40 | 11 |
| 36 | NT | NT | NT | NT | 105 | NT | NT | NT |
| 47 | 47 | 26 | 16 | 8 | 25 | <20 | <20 | <20 |

TABLE VI

| Compound No. | RMPI8226 micromolar |
|---|---|
| Etodolac | 140 |
| 36 | 75 |
| 47 | 16 |
| 54 | 20 |
| 55 | 37 |
| 56 | 238 |
| 57 | 320 |

Antiangiogenic Assay

To determine the effects of COX inhibitors on angiogenesis in vivo, selective compounds will be tested in the mouse and rat corneal micropocket assay. The mouse corneal neovascularization micropocket model is performed with materials, reagents and procedures essentially as described by Muthukkauppah et al., 1982 *J. Natl. Cancer Inst.*, 69, 699-708. In this assay, a pellet containing basic fibroblast growth factor (FGF) is implanted into the corneal stroma of the mouse and the newly formed vessels are measured using a slit lamp. In this model, COX-2 is expressed in the endothelial cells of the newly developed blood vessels. The ability of a compound of the invention to inhibit FGF-induced angiogenesis in the mouse will be tested using the above method. The inhibitory effects of the compounds of the invention in the mouse cornea model will be tested using another angiogenic stimulus, vascular endotherlial growth factor (VEGF).

Cyclin D1

Cyclin D1 Transcript Expression Levels as measured by quantitative PCR assay. LNCaP cells were cultured at 37° C., 5% $CO_2$ for 24 hours untreated or in the presence of R-etodolac (200 μM), compound 42 (50 μM), compound 36 (100 μM), or compound 1 (20 μM) (see Table II for structures). Cells were harvested by trypsinization, washed with PBS, and stored at −80° C. Total cellular RNA was prepared from cell pellets using the RNEasy® Mini kit (Qiagen, Inc., Valencia, Calif.). RNA was quantified by spectrophotometer. Approximately 2 μg of RNA was used to prepare cDNA using the ThermoScrip™ RT-PCR System (Invitrogen, Carlsbad, Calif.).

The levels of cyclin D1 transcripts in the cDNA samples were measured using a quantitative PCR (qPCR) assay specific for cyclin DI. The cyclin D1 transcript was amplified using the following primer pair:

```
                                         (SEQ ID NO:1)
    Cyclin D1 for: 5'- AATGACCCCGACCGATT-3'

(SEQ ID NO:2)
    Cyclin D1 rev: 5'- GCACAAGAGGCAACGAAG G-3'
```

The cyclin D1 primers are described in a manuscript from Takayasu et al. (2001 *Clin. Cancer Res.* 7:901-908). All assays were performed in duplicate. All qPCR assays were performed and analyzed using a Bio-Rad iCycler (Bio-Rad, Hercules, Calif.). The levels of cyclin D1 transcripts were normalized for total input cDNA by performing a separate assay to detect the levels of a housekeeping gene (18s).using the following primer pair:

```
18s for: 5'-CGCCGCTAGAGGTGAAATTC-3'   (SEQ ID NO:3)

18s rev: 5'-TTGGCAAATGCTTTCGCTC-3'    (SEQ ID NO:4)
```

Figure 2:
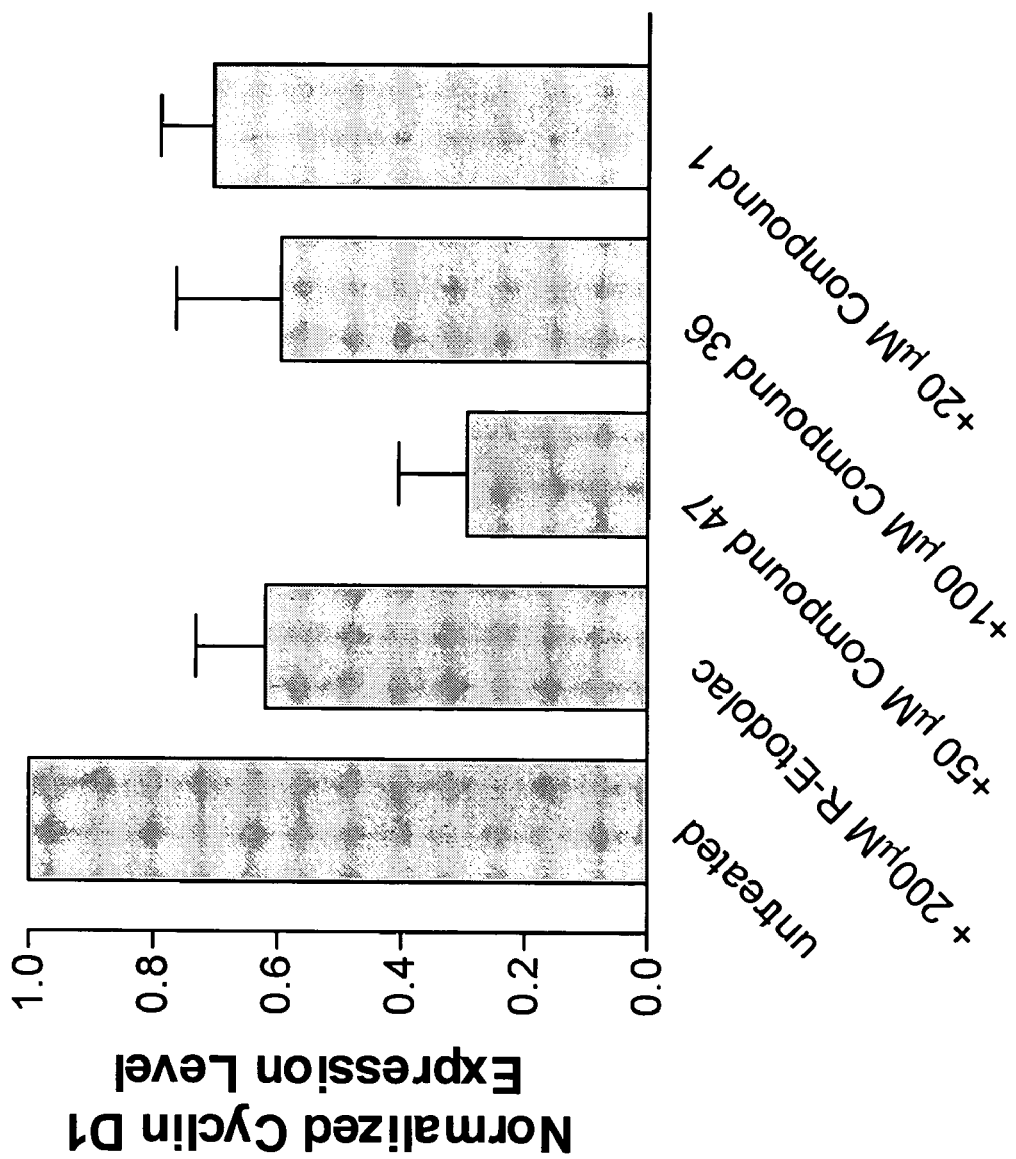
FIG. 2 shows inhibition of Cyclin D1 mRNA expression by R-etodolac and compounds of the invention.

The samples were normalized for 18s transcript levels using the method of Livak et al. (2001 *Methods* 25:402-408). The level of cyclin D1 transcripts in the control sample was set to 1. FIG. 2 represents the averaged normalized cyclin D1 transcripts ± standard deviation for three independent experiments (two independent experiments for compound 1). The data show that compound 42, compound 36, and compound 1 inhibit cyclin D1 mRNA expression.

Western blot analysis of LNCaP cell lysates from cells treated with R-etodolac, compound 42, compound 36, or compound 1 using a monoclonal antibody specific for Cyclin D1 (BD Pharmingen) confirmed that the compounds reduced Cyclin D1 protein expression.

Other Cyclin D proteins have been shown to be dependent on the Wnt/beta-catenin pathway (e.g., cyclin D2—Briata et al. 2003 *Mol. Cell* 12:1201-11) and would be expected to be affected by the compounds of the invention in a similar way as Cyclin D1. The inhibition of cyclin D expression by the compounds of the invention can also be used as a biomarker of the efficacy of these compounds.

Example 3

DAUDI LYMPHOMA MURINE XENOGRAFT MODEL MICE STUDIES

Materials

Male SCID mice, 6-8 weeks of age, obtained from Simonsen Laboratories, Inc. (Gilroy, Calif.) were housed in groups of five.

The Daudi human Burkitt Lymphoma cells were obtained from American Type Culture Collection and were inoculated subcutaneously (1.0×107 cells/mouse) on the flanks of SCID mice. After the tumors reached approximately 100 mm3 treatment was initiated.

Body weights and tumor volume of all mice were measured and recorded twice weekly. Tumors were measured in three dimensions and volume calculated using the formula: 4 3π3. Time for the tumors (days) to grow to 4× and 8× the initial volume at dosing were assessed. Study compounds were administered at 125 or 250 mg/kg/day (M-F) via oral gavage until the end of the study.

Efficacy

The efficacy of chlorambucil (2 and 3 mg/kg/d), (R-etodoalc) (400 mg/kg/d) and compound 47 (250 mg/kg/d), compound 26 (250 mg/kg/d), and compound 1 (125 mg/kg/d) against Daudi derived tumors in male SCID mice were studied. R-etodolac and compounds 1, 26 and 47 were prepared in sesame oil. Both chlorambucil (ip, 0.1 ml) and compounds of the invention (per os [p.o.], 0.31ml) were dosed daily (Monday to Friday) for two weeks. SDX-101 (0.31 ml) was dosed p.o. daily until the end of the study. Slight body weight loss (<3%) was observed at the beginning of the study in chlorambucil (2 mg/kg/d), compounds 47 and 36 treated groups. However, all treated mice recovered after Day 2 and maintained their weights. There was no body weight loss observed in other treatment groups. At termination of the study, the control group mean tumor volume was 1583 mm$^3$. The mean tumor volume of chlorambucil treated groups were 864 and 766 mm$^3$ with 2 and 3 mg/kg/d chlorambucil treatment, respectively. The mean tumor volume of R-etodolac and compounds 1, 36 and 47 were 802, 996, 1011, and 1157 mm$^3$ with compounds 47, 36, 1 and R-etodolac treatment, respectively. Analysis of variance (ANOVA) of tumor volume of control and chlorambucil groups on Day 20 showed a p-value of 0.001 and 0.0003 between the control group vs 2 and 3 mg/kg/d chlorambucil treated groups, respectively. ANOVA also showed a p-value of 0.007 and 0.03 between the control group vs compound 47 and compound groups, respectively. At termination of the study, tumor samples along with liver, kidney, and spleen samples from each group were collected and fixed in 10% buffered formalin for histopathology. Histological analysis of all liver, spleen and kidney tissues indicated that all tissues appeared normal.

Table VII shows the time for the tumors to grow to 4× and 8× the initial volume when mice were administered chlorambucil, R-etodolac and compounds 1, 36 and 47. These data indicate that the compounds of the invention inhibit tumor growth in the Daudi mouse model.

TABLE VII

| Group | 4X Growth (d) | 8X Growth (d) |
| --- | --- | --- |
| Control | 8.9 | 14.5 |
| Chlorambucil | 16 | 21 |
| R-etodolac | 11 | 17 |
| Compound 47 | 16 | 21.5 |
| Compound 1 | 15.8 | 21.1 |
| Compound 36 | 13.5 | 20.8 |

All patents and documents referenced herein are incorporated by reference.

The invention is not limited to those embodiments described herein, but may encompass modification and variations which do not depart from the spirit of the invention. While the invention has been described in connection with specific embodiments thereof, those of ordinary skill in the art will understand that further modifications are within the scope of the following claims. In addition, where features or aspects of the invention are described in terms of Markush groups or other grouping of alternatives, those skilled in the art will recognize that the invention is also thereby described in terms of any individual member or subgroup of members of the Markush group or genus, and exclusions of individual members as appropriate.

What is claimed is:

1. A compound of Formula (I):

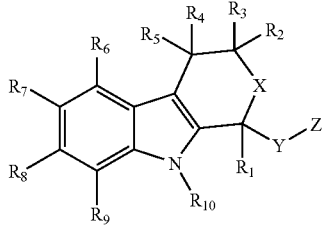

(I)

wherein:

(a) X is O;

(b) $R_1$ is halogen; —CN; —OH; —SH; —NO$_2$; or an unsubstituted or substituted moiety selected from alkyl, alkenyl, alkynyl, aryl, heteroaryl, heterocycloalkyl, and cycloalkyl, wherein the substituted groups are substituted with one, two or three suitable substituents each independently selected from the group consisting of: halogens, —CN, —NO$_2$, unsubstituted alkyl, unsubstituted alkenyl, unsubstituted heteroalkyl, unsubstituted haloalkyl, unsubstituted alkynyl, unsubstituted aryl, unsubstituted cycloalkyl, unsubstituted heterocycloalkyl, unsubstituted heteroaryl, and —(CH$_2$)$_z$CN where z is an integer from 0 to 6;

(c) $R_2$, $R_3$, $R_4$ and $R_5$ are each independently hydrogen; halogen; —CN; —OH; —SH; —NO$_2$; or an unsubstituted or substituted moiety selected from lower alkyl, lower alkynyl, lower alkenyl, alkoxy, haloalkyl, aryl, and heteroaryl;

(d) $R_6$, $R_8$ and $R_9$ are each independently hydrogen; halogen; —CN; —OH; —SH; —NO$_2$; or an unsubstituted or substituted moiety selected from alkyl, alkenyl, alkynyl, alkoxy, and allyloxy;

(e) $R_7$ is halogen; —CN; —OH; —SH; —NO$_2$; or an unsubstituted or substituted moiety selected from alkyl, alkenyl, and alkynyl (f) $R_{10}$ is hydrogen; or an unsubstituted or substituted moiety selected from lower alkyl, lower alkenyl, lower alkynyl, aryl; heteroaryl, heterocycloalkyl, and cycloalkyl;

(g) Y is an unsubstituted or substituted moiety selected from alkyl, alkenyl, and alkynyl; wherein the substituted moiety is substituted with one, two or three substitutents each independently selected from halogen; —CN; —OH; —SH; —NO$_2$; unsubstituted alkyls, unsubstituted alkenyls, unsubstituted alkynyls, unsubstituted heteroalkyls, unsubstituted haloalkyls, unsubstituted aryls, unsubstituted cycloalkyls, unsubstituted heterocycloalkyls, and unsubstituted heteroaryls; and (h) Z is —OH or —SH;

wherein $R_1$ and Y may cyclize to form an unsubstituted or substituted cycloalkyl group or an unsubstituted or substituted heterocycloalkyl group;

or pharmaceutically acceptable salt thereof.

2. A compound according to claim 1, wherein $R_1$ is an unsubstituted lower alkyl group or unsubstituted aryl group; and —Y-Z is —CH$_2$—CH$_2$—OH; or pharmaceutically acceptable salt thereof.

3. A compound according to claim 1, wherein $R_2$, $R_3$, $R_4$ and $R_5$ are each H.

4. A compound according to claim 3, wherein $R_1$ is an unsubstituted lower alkyl group or unsubstituted aryl group; and —Y-Z is —CH$_2$—CH$_2$—OH; or pharmaceutically acceptable salt thereof.

5. A compound according to claim 1, wherein $R_{10}$ is H or methyl.

6. A compound according to claim 1, wherein
$R_1$ is an unsubstituted lower alkyl group or unsubstituted aryl group;
$R_2$, $R_3$, $R_4$ and $R_5$ are each H;
$R_{10}$ is H or methyl; and
—Y-Z is —CH$_2$—CH$_2$—OH;
or pharmaceutically acceptable salt thereof.

7. A compound according to claim 6, wherein $R_7$ is halogen; —CN; —OH; —SH; —NO$_2$; unsubstituted lower alkyl, unsubstituted lower alkenyl, unsubstituted lower alkynyl, alkyl-C(O)$_2$H, alkyl-C(O)$_2$-alkyl, or alkyl-hydroxy; or pharmaceutically acceptable salt thereof.

8. A compound according to claim 7, wherein
$R_6$ is hydrogen or halogen;
$R_7$ is halogen, unsubstituted lower alkyl, alkyl-C(O)$_2$H, alkyl-C(O)$_2$-alkyl, or alkyl-hydroxy;
$R_8$ is hydrogen or halogen;
$R_9$ is hydrogen, halogen, or an unsubstituted or substituted moiety selected from alkyl, alkenyl, and alkynyl;
or pharmaceutically acceptable salt thereof.

9. A compound according to claim 7, wherein $R_7$ is halogen.

10. A compound according to claim 8, wherein $R_7$ is halogen.

11. A compound according to claim 10, wherein $R_7$ is Br.

12. A compound according to claim 1, wherein:

(a) X is O; (b) $R_1$ is an unsubstituted moiety selected from lower alkyl, lower alkyl-hydroxy, lower alkenyl, lower alkenyl-hydroxy, lower alkynyl, lower alkynyl-hydroxy, aryl, heteroaryl, heterocycloalkyl, and cycloalkyl;

(c) $R_2$, $R_3$, $R_4$ and $R_5$ are each independently hydrogen; or an unsubstituted moiety selected from lower alkyl, lower alkynyl, lower alkenyl, alkoxy, haloalkyl, aryl, and heteroaryl;

(d) $R_6$, $R_8$ and $R_9$ are each independently hydrogen; or an unsubstituted or substituted moiety selected from alkyl, alkenyl, alkynyl, alkoxy, and allyloxy, wherein the substituted moieties are each independently selected from the group consisting of halogen, —CN, alkyl, alkoxy, —NH$_2$, —O-haloalkyl, —CH(O), haloalkyl, alkenyl, alkynyl, —OH, —C(O)$_2$-alkyl, and —C(O)$_2$H;

(e) $R_7$ is halogen; —CN; —OH; —SH; —NO$_2$; unsubstituted lower alkyl, unsubstituted lower alkenyl, unsubstituted lower alkynyl, alkyl-C(O)$_2$H, alkyl-C(O)$_2$-alkyl, or alkyl-hydroxy; and (f) $R_{10}$ is hydrogen; or an unsubstituted moiety selected from lower alkyl, lower alkenyl, lower alicynyl, aryl, benzyl, heteroaryl, heterocycloalkyl, and cycloalkyl.

13. A compound according to claim 1, wherein
(a) X is O;
(b) $R_1$ is an unsubstituted alkyl group;
(c) $R_2$, $R_3$, $R_4$ and $R_5$ are each hydrogen;
(d) $R_7$ is halogen, unsubstituted lower alkyl, alkyl-C(O)$_2$H, alkyl-C(O)$_2$-alkyl, or alkyl-hydroxy; and
(e) $R_{10}$ is hydrogen.

14. A compound according to claim 1, wherein:
(a) $R_9$ is hydrogen, halogen or an unsubstituted alkyl group;
(b) Y is an unsubstituted alkyl group; and
(c) Z is —OH.

15. A compound according to claim 1, wherein:
(a) X is O;
(b) $R_1$ is an unsubstituted lower alkyl group or unsubstituted aryl group;
(c) $R_2$, $R_3$, $R_4$ and $R_5$ are each hydrogen;
(d) $R_6$ is hydrogen or halogen;
(e) $R_7$ is halogen, unsubstituted lower alkyl, alkyl-C(O)$_2$H, alkyl-C(O)$_2$-alkyl, or alkyl-hydroxy;
(f) $R_8$ is hydrogen or halogen;
(g) $R_9$ is hydrogen; or an unsubstituted or substituted moiety selected from alkenyl, and alkynyl; and
(h) $R_{10}$ is hydrogen.

16. A compound according to claim 1, wherein:
(a) X is O;
(b) $R_1$ is methyl, ethyl, propyl, -ethyl-OH, or phenyl;
(c) $R_2$, $R_3$, $R_4$ and $R_5$ are each independently hydrogen;
(d) $R_6$, $R_8$ and $R_9$ are each independently hydrogen; halogen; —CN; or an unsubstituted or substituted moiety selected from alkyl, alkenyl, alkynyl, alkoxy, and allyloxy;
(e) $R_7$ is F, Cl, Br, methyl, ethyl, or propyl;
(f) $R_{10}$ is hydrogen or methyl;
(g) Y is —CH$_2$—CH$_2$—; and
(h) Z is —OH;
or pharmaceutically acceptable salt thereof.

17. A compound having the following structure:

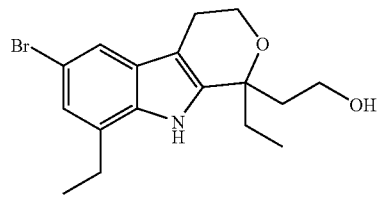

or a pharmaceutically acceptable salt thereof.

18. A compound having the following structure:

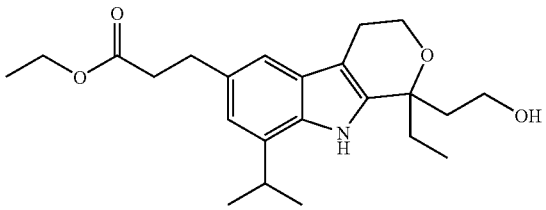

or a pharmaceutically acceptable salt thereof.

19. A compound having the following structure:

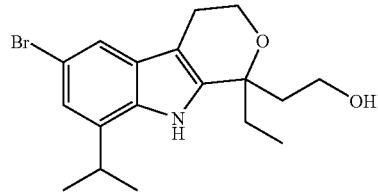

or a pharmaceutically acceptable salt thereof.

20. A pharmaceutical composition comprising a therapeutically effective amount of a compound of claim 1 and a pharmaceutically acceptable carrier.

21. A pharmaceutical composition comprising a therapeutically effective amount of a compound of claim 9 and a pharmaceutically acceptable carrier.

22. A pharmaceutical composition comprising a therapeutically effective amount of a compound of claim 10 and a pharmaceutically acceptable carrier.

23. A pharmaceutical composition comprising a therapeutically effective amount of a compound of claim 11 and a pharmaceutically acceptable carrier.

24. A pharmaceutical composition comprising a therapeutically effective amount of a compound of claim 16 and a pharmaceutically acceptable carrier.

25. A pharmaceutical composition comprising a therapeutically effective amount of a compound of claim 17 and a pharmaceutically acceptable carrier.

26. A pharmaceutical composition comprising a therapeutically effective amount of a compound of claim 18 and a pharmaceutically acceptable carrier.

27. A pharmaceutical composition comprising a therapeutically effective amount of a compound of claim 19 and a pharmaceutically acceptable carrier.

28. A compound selected from the group consisting of:
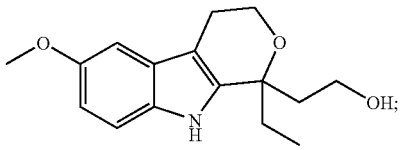
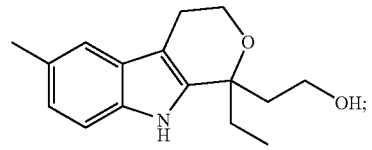
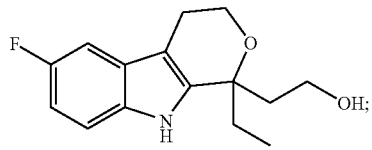
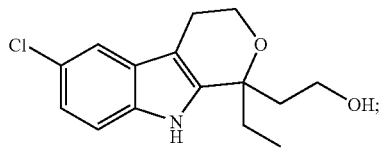
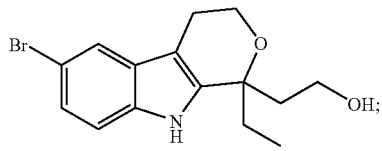
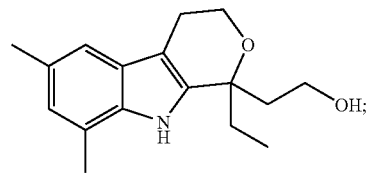
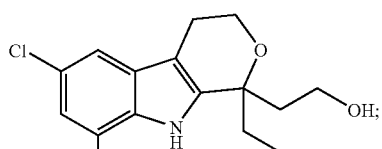
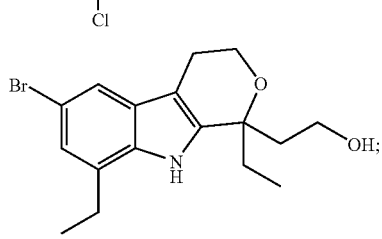
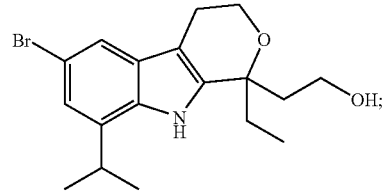
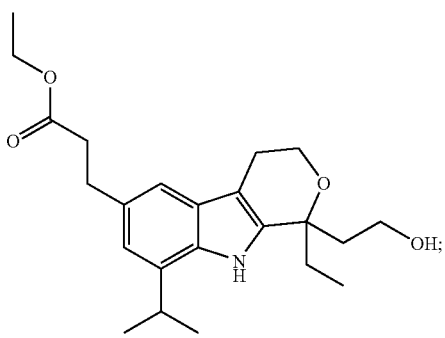
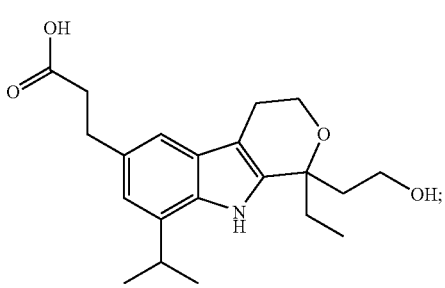
and
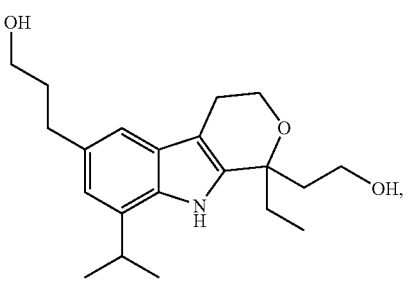
or a pharmaceutically acceptable salt thereof.
29. A pharmaceutical composition comprising a therapeutically effective amount of a compound of claim 28 and a pharmaceutically acceptable carrier.
* * * * *